(12) United States Patent
Shimamura et al.

(10) Patent No.: US 9,639,952 B2
(45) Date of Patent: May 2, 2017

(54) IMAGE-PROCESSING APPARATUS AND STORAGE MEDIUM

(71) Applicant: KONICA MINOLTA, INC., Tokyo (JP)

(72) Inventors: Kenta Shimamura, Takatsuki (JP); Hiroshi Yamato, Amagasaki (JP); Osamu Toyama, Kakogawa (JP); Shintaro Muraoka, Hachioji (JP); Sho Noji, Kokubunji (JP)

(73) Assignee: KONICA MINOLTA, INC., Tokyo (JP)

( * ) Notice: Subject to any disclaimer, the term of this patent is extended or adjusted under 35 U.S.C. 154(b) by 113 days.

(21) Appl. No.: 14/651,150

(22) PCT Filed: Dec. 4, 2013

(86) PCT No.: PCT/JP2013/082548
§ 371 (c)(1),
(2) Date: Jun. 10, 2015

(87) PCT Pub. No.: WO2014/091977
PCT Pub. Date: Jun. 19, 2014

(65) Prior Publication Data
US 2015/0310625 A1      Oct. 29, 2015

(30) Foreign Application Priority Data

Dec. 12, 2012 (JP) .................................. 2012-271547
Jan. 25, 2013 (JP) .................................. 2013-012096

(51) Int. Cl.
*G06K 9/00* (2006.01)
*G06T 7/20* (2017.01)
*A61B 6/00* (2006.01)

(52) U.S. Cl.
CPC .............. *G06T 7/20* (2013.01); *A61B 6/4233* (2013.01); *A61B 6/486* (2013.01); *A61B 6/507* (2013.01);
(Continued)

(58) Field of Classification Search
None
See application file for complete search history.

(56) References Cited

U.S. PATENT DOCUMENTS 9,171,367 B2 * 10/2015 Iwase .................... G06T 7/0026
9,301,710 B2 *  4/2016 Mestha ................ A61B 5/0064
(Continued)

FOREIGN PATENT DOCUMENTS

JP      2003-249398 A      9/2003
JP      2004-201730 A      7/2004
(Continued)

OTHER PUBLICATIONS

International Search Report in International Application No. PCT/JP2013/082548, dated Jan. 7, 2014, 2 pages.
(Continued)

*Primary Examiner* — Nancy Bitar
(74) *Attorney, Agent, or Firm* — Brinks Gilson & Lione

(57) ABSTRACT

An image processing apparatus includes a moving image acquiring unit that acquires a moving image including a plurality of frame images a respiratory information acquiring unit that performs a respiratory information acquiring processing of acquiring respiratory information synchronized at times at which the frame images are captured, a blood-flow-restricted time determining unit that performs a blood-flow-restricted time determining processing of determining, on the basis of the respiratory information, a blood-flow-restricted time indicating a time at which the blood flow of the target region is assumed to be restricted due to (Continued)

respiration, and a blood flow analysis correcting unit that performs a blood-flow-analysis content correcting processing of excluding the frame image captured at the blood-flow-restricted time from targets for blood flow analysis or decreasing the blood-flow-analysis importance of the frame image compared with another time period.

29 Claims, 50 Drawing Sheets

(52) U.S. Cl.
CPC .... *A61B 6/527* (2013.01); *G06T 2207/10116* (2013.01); *G06T 2207/20076* (2013.01); *G06T 2207/30061* (2013.01); *G06T 2207/30104* (2013.01)

(56) References Cited

U.S. PATENT DOCUMENTS

| | | | | |
|---|---|---|---|---|
| 2012/0130238 | A1* | 5/2012 | Muraoka | A61B 6/4233 600/436 |
| 2013/0058557 | A1* | 3/2013 | Nagatsuka | A61B 5/08 382/132 |
| 2013/0324875 | A1* | 12/2013 | Mestha | A61B 5/0064 600/534 |
| 2015/0073257 | A1* | 3/2015 | Muraoka | A61B 6/4233 600/407 |
| 2015/0254852 | A1* | 9/2015 | Yamato | A61B 6/5288 345/634 |

FOREIGN PATENT DOCUMENTS

| | | |
|---|---|---|
| JP | 2004-312434 A | 11/2004 |
| JP | 3793102 | 4/2006 |
| JP | 2009-291313 A | 12/2009 |
| JP | 2012-110399 A | 6/2014 |
| WO | WO 2007/078012 A1 | 12/2007 |
| WO | WO 2013/141067 A1 | 9/2013 |

OTHER PUBLICATIONS

Nakamori, Nobuyuki et al., "Image feature analysis and computer-aided diagnosis in digital radiography: Automated analysis of sizes of heart and lung in chest images," Medical Physics, vol. 17, Issue 3, dated May, 1990, pp. 342-350.

Xin-Wei Xu and Kunio Doi, "Image feature analysis and computer-aided diagnosis: Accurate determination of ribcage boundary in chest radiographs," Medical Physics, vol. 22(5), dated May 1995, pp. 617-626.

Aoki, Hirooki and Nakamima, Masato, "Unrestrained Respiration Monitoring for Sleeping Person Using Fiber Grating Vision Sensor," The Institute of Electronics, Information and Communication Engineers, Society Conference, Proceedings 2001, Information, System Society Conference Report, pp. 320,and 321, dated Aug. 29, 2001.

* cited by examiner

FIG. 5
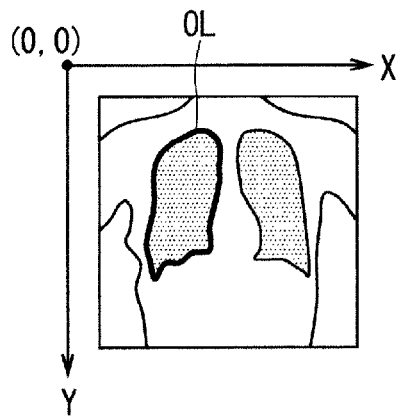
(a)
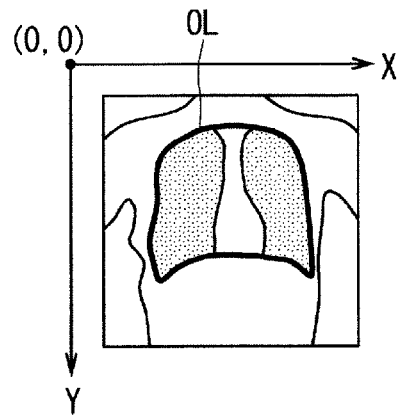
(b)
FIG. 6
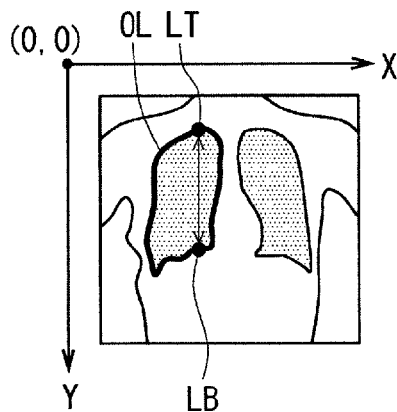
(a)
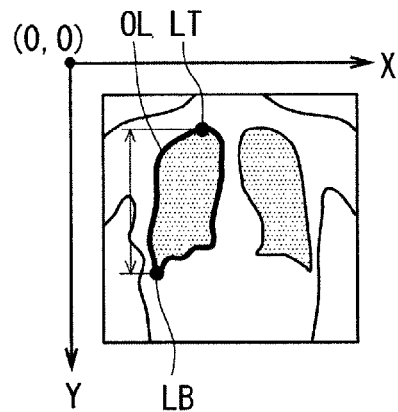
(b)
FIG. 7
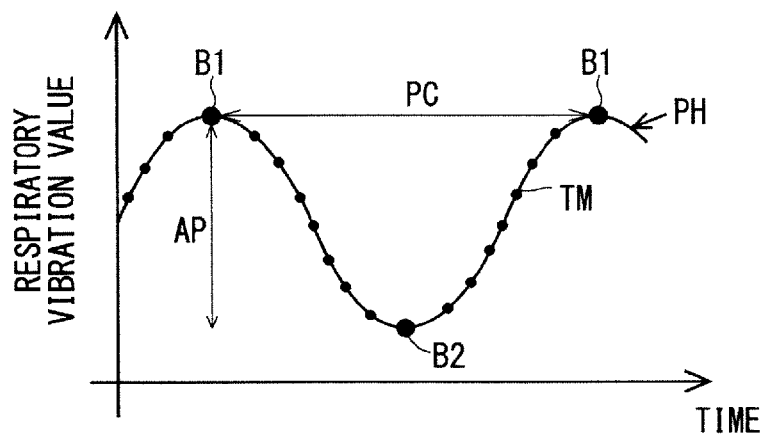

F I G. 1 8
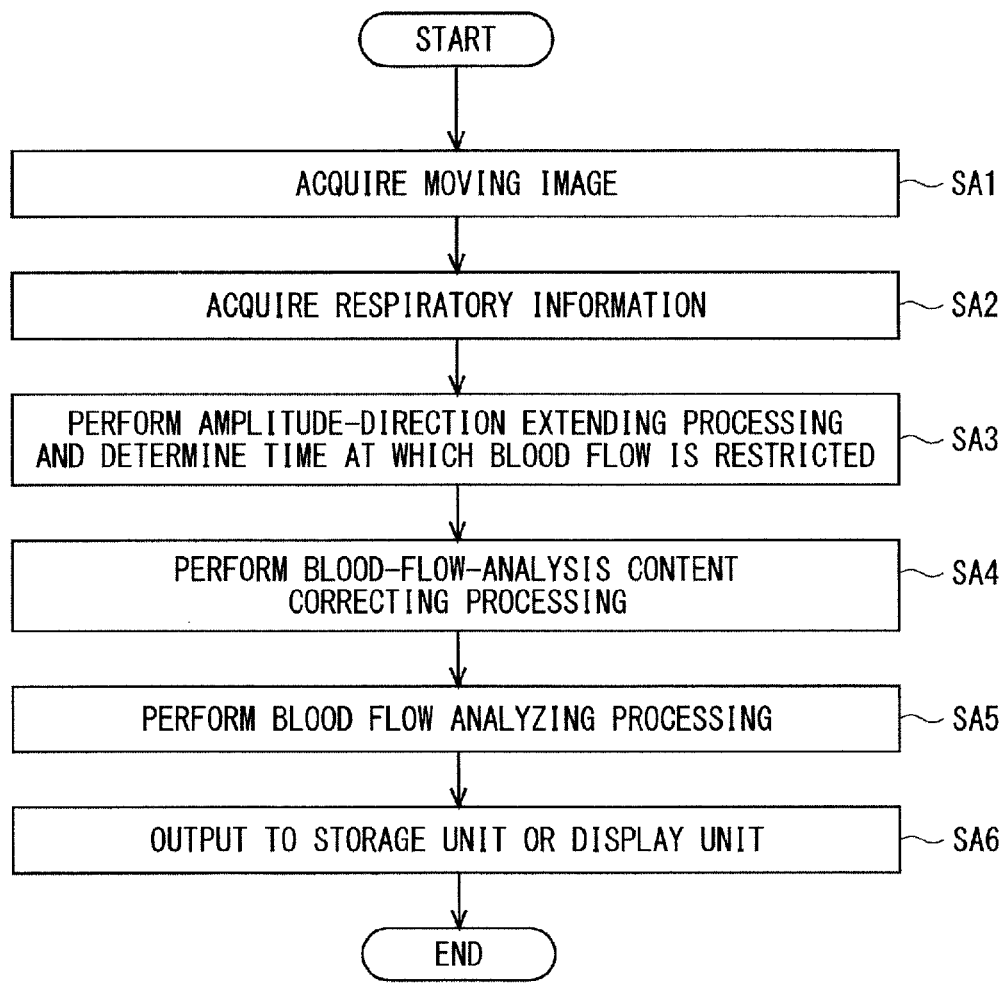

F I G. 2 3
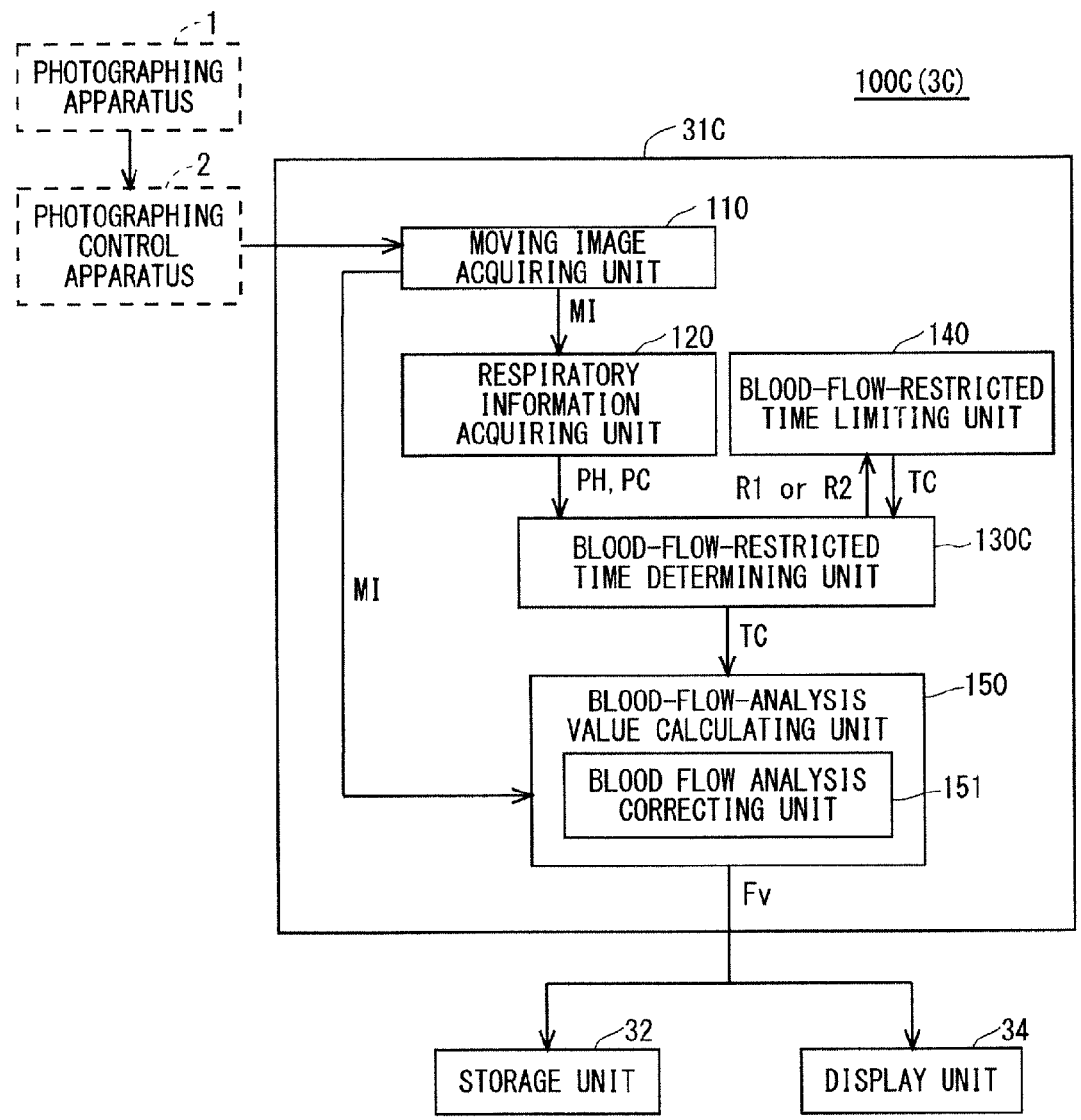

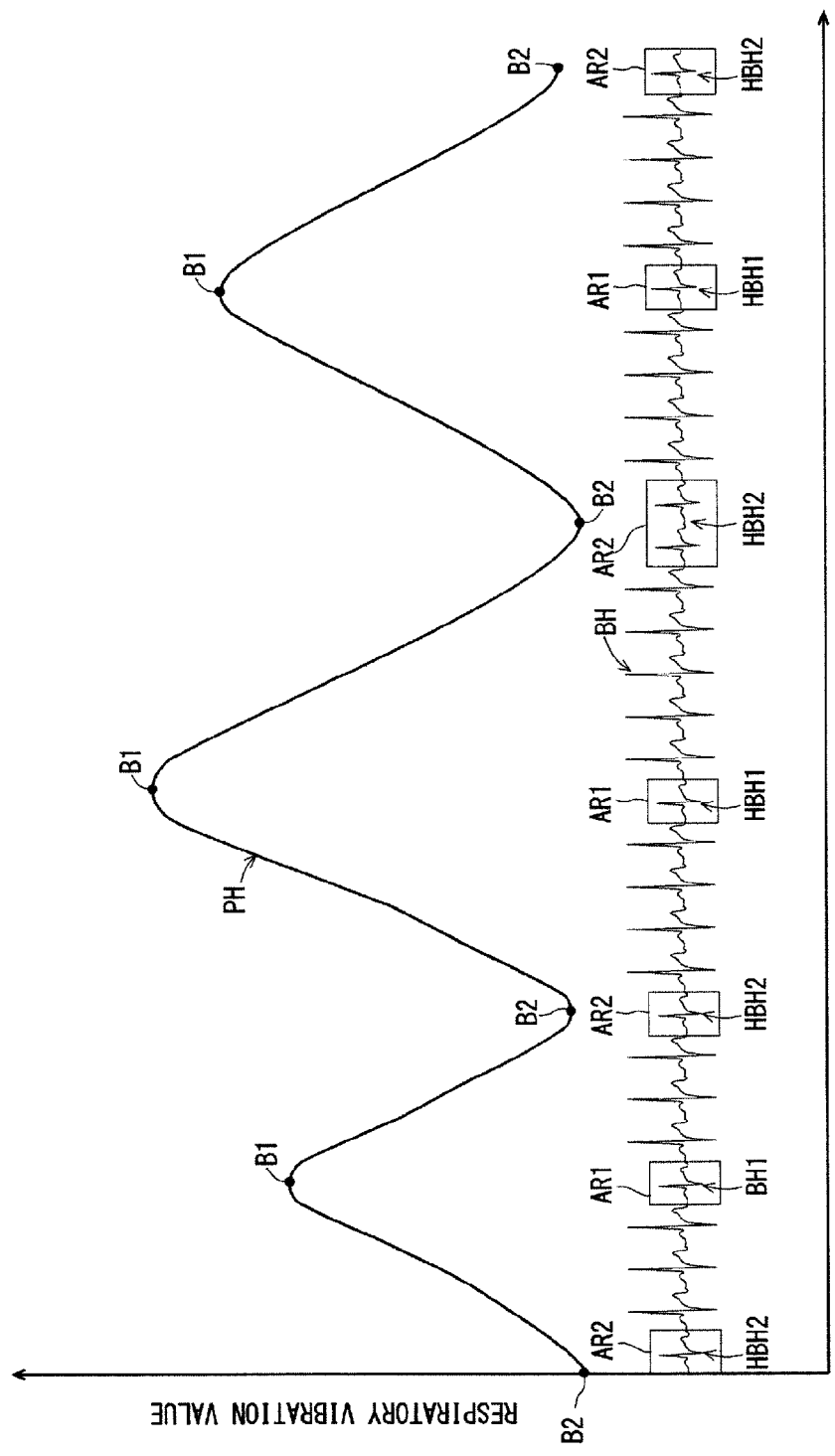

F I G. 3 8
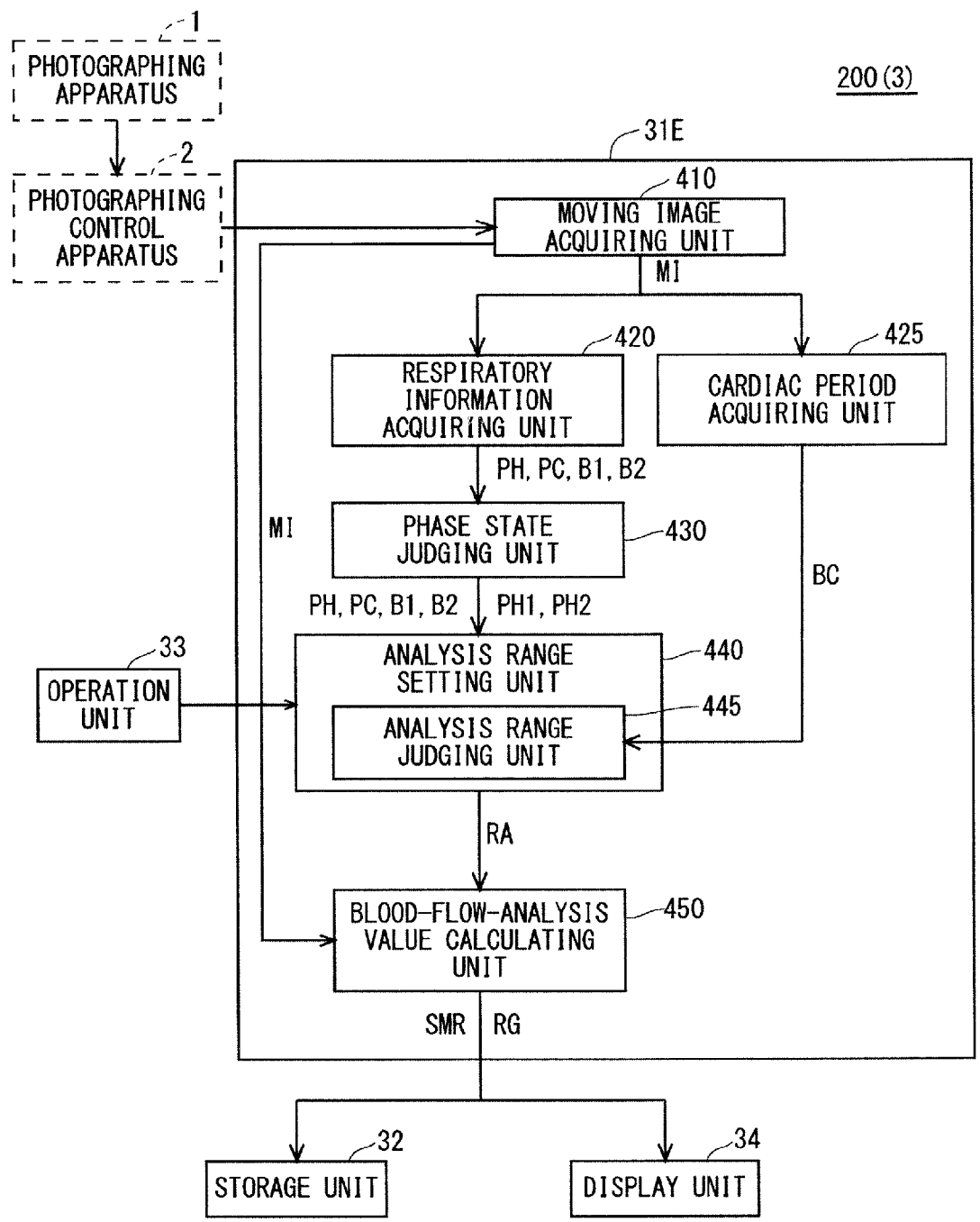

F I G . 4 0
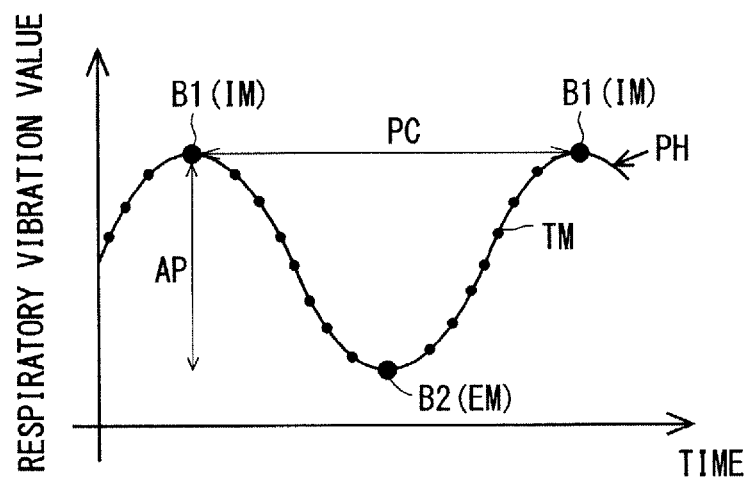
F I G . 4 1
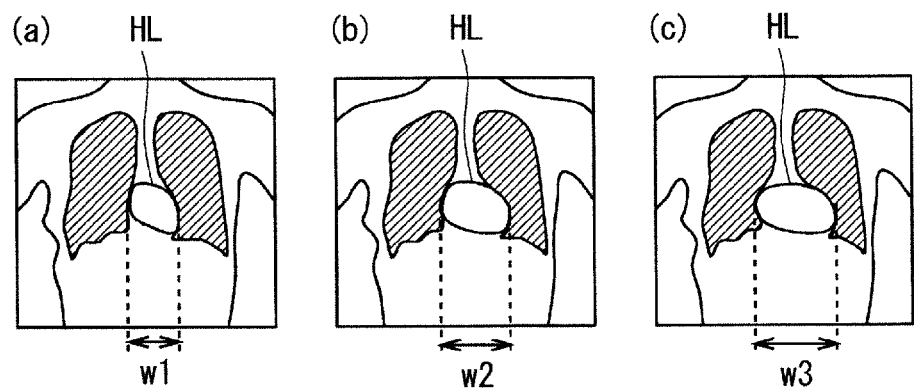

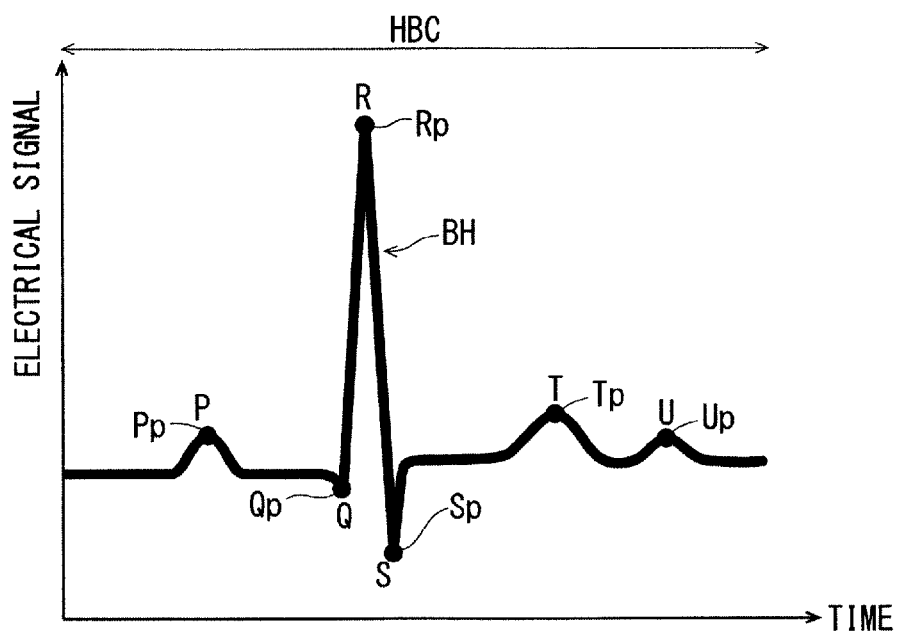
F I G . 4 3

F I G . 4 7
(a)
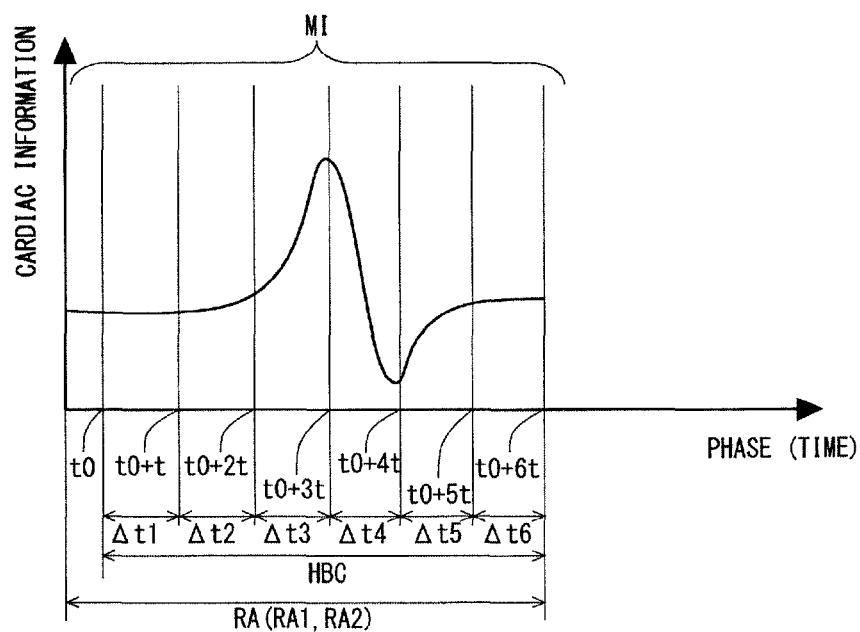
(b)
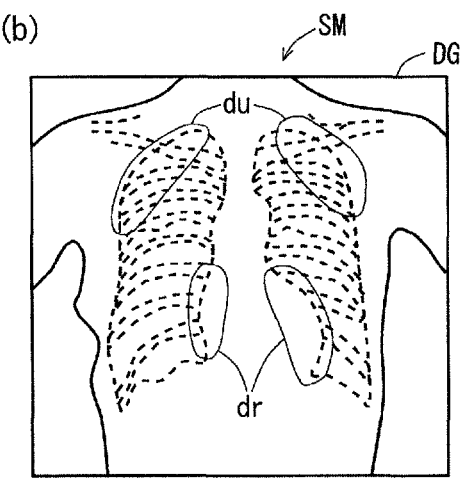

FIG. 48
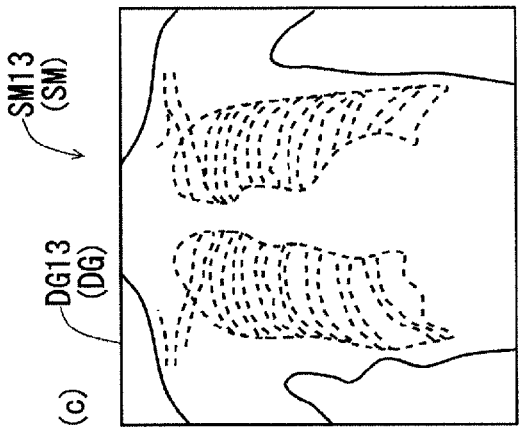
(c)
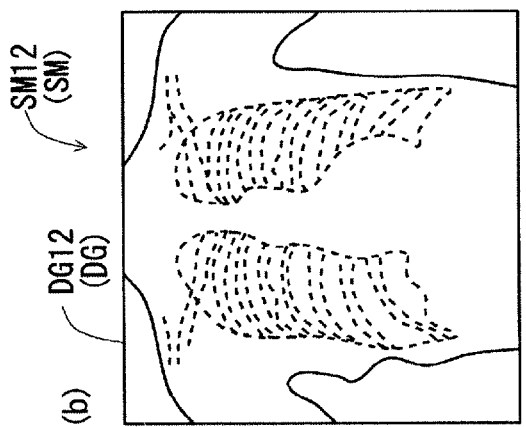
(b)
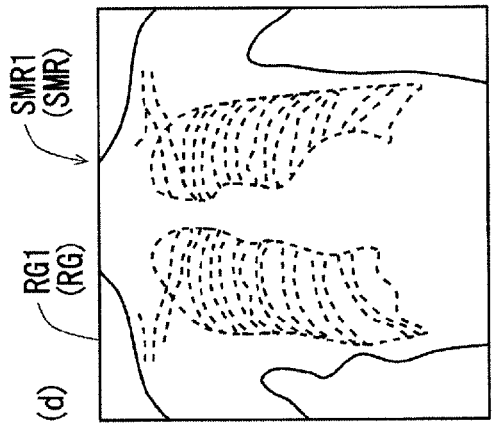
(d)
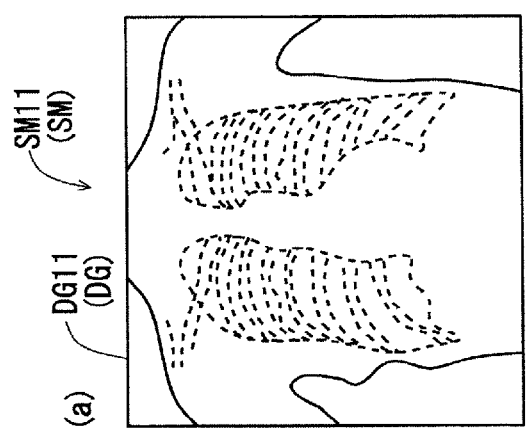
(a)

FIG. 49
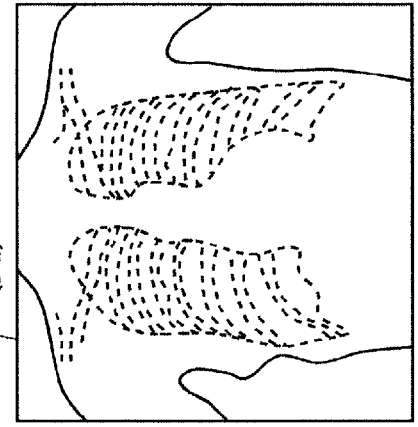
(c)
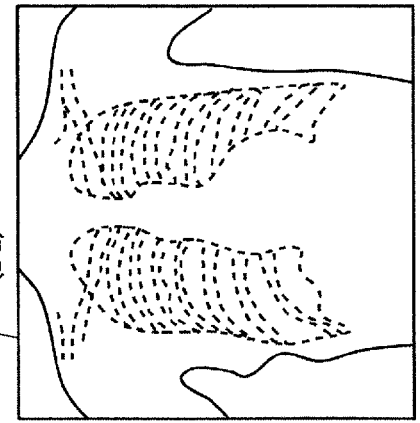
(b)
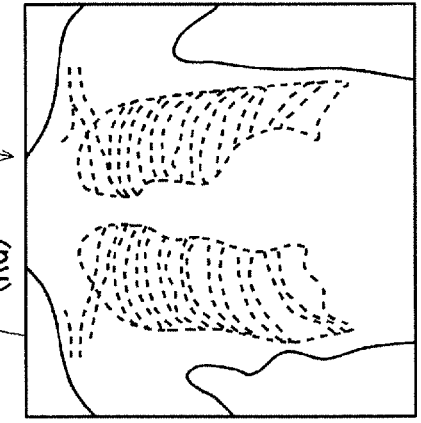
(d)
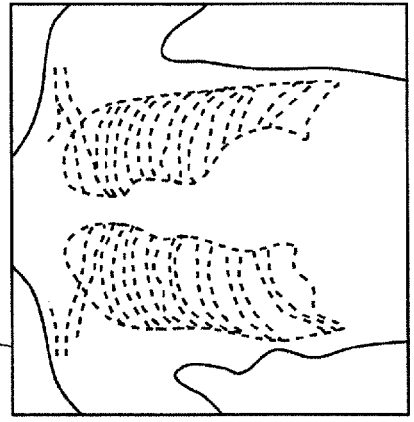
(a)

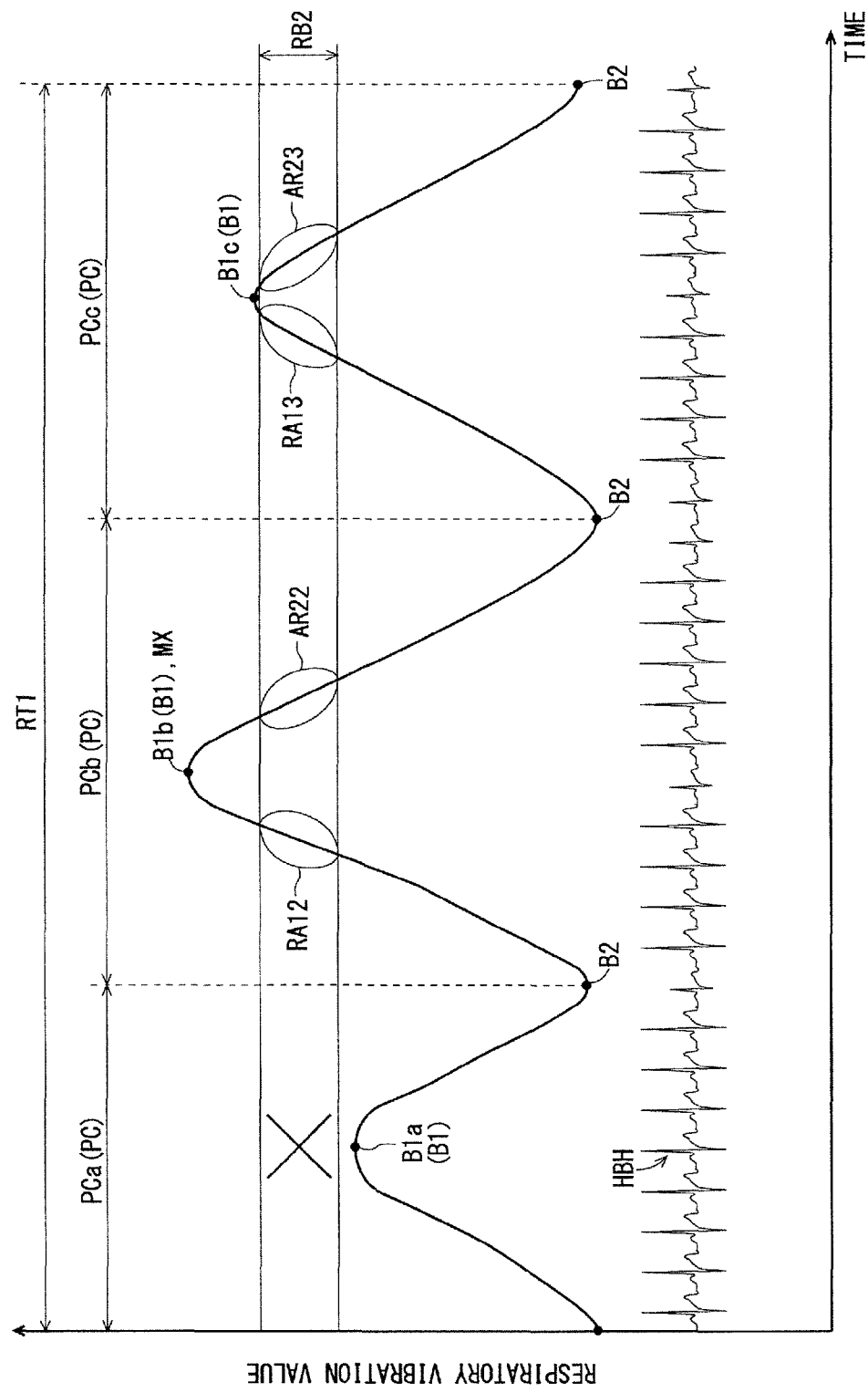

IMAGE-PROCESSING APPARATUS AND STORAGE MEDIUM

This application is a National Stage application of International Application No. PCT/JP2013/082548, filed Dec. 4, 2013.

TECHNICAL FIELD

The present invention relates to an image processing technology for a dynamic image in which a human body or an animal body is photographed.

BACKGROUND ART

In medical practice, an affected part in internal organs, skeletons, and the like is photographed with, for example, X-rays for various tests and diagnoses. Through application of recent digital technology, a moving image (an image group composed of a plurality of frame images) that captures the movement of an affected part with X-rays or the like can be acquired relatively readily.

In the recent digital technology, a dynamic image of a subject region including a diagnosis target region can be photographed using a semiconductor image sensor such as a flat panel detector (FPD), enabling diagnosis through motion analysis of the diagnosis target region, which cannot be made in still image photographing and diagnosis by conventional X-ray photography. Particularly in dynamic analysis of the chest with X-rays, the use of interframe differences of a moving image in the chest enables analysis of a ventilatory function and a blood flow function related to two major movements, namely, respiration and heart rate, for every position of the chest. Such analysis therefore receives attention as the method of readily diagnosing respiration and blood flow with a small amount of exposure.

In recent years, various image processing technologies have been proposed as dynamic analysis of the ventilatory function and the blood flow function. For example, Patent Document 1 discloses the following technology. Filters are separately used in such a manner that the processing using a highpass filter is performed in blood flow analysis and the processing using a lowpass filter is performed in ventilatory analysis to prevent the blood flow and respiration from affecting each other and prevent the density values thereof from affecting each other, thereby accurately extracting the respiration and blood flow using an inter-filter difference.

Patent Document 2 discloses a technology of detecting a current phase in a respiratory cycle of a test subject to control an X-ray source in accordance with the current phase.

Pathological analysis and diagnosis based on a motion analysis for a diagnosis target region, which cannot be performed through still image photographing and diagnosis based on the conventional X-ray photographing, are tried using a semiconductor image sensor such as an FPD described above. Particularly in dynamic analysis of the chest using X-rays, the following study is conducted; the respiratory information and blood flow information in the lung field are extracted, and the dynamic function as to changes in the density value of the lung field and the movement of blood flow at every position are quantitively analyzed, to thereby aid diagnosis and/or treatment (CAD for X-ray moving image).

As the method for the quantitative analysis as described above, the following methods for ventilatory analysis and blood flow analysis are proposed. Such a method analyzes temporal changes on the basis of the interframe difference information of a moving image of the chest to acquire detailed functional data for every position of the chest, that is, the information on the abnormal-ventilation-spot analysis values regarding the movement in respiration and on the abnormal-blood-flow-spot analysis values regarding the movement of a blood flow.

For example, Patent Document 3 discloses a technology of calculating differential images of temporally adjacent images using a plurality of X-ray moving images acquired continuously in time sequence, thereby generating one image composed of pixels each indicating a maximum pixel value for its corresponding pixel group in a plurality of differential images.

Patent Document 4 discloses a technology of using the property, in which the pixel value of the lung field in an X-ray image of the chest changes due to cardiac pulsation, and employing the information on changes in pixel value as the information on pulmonary blood flow, thereby effectively using the information for diagnosis of pulmonary embolism, cardiac disease, or the like. In a specific technique for the method, the dynamic state of the heart during ventricular dilation is acquired to generate the information on changes in the pixel value of the X-ray moving image of the chest associated with an increase in blood flow (an increase in pulmonary blood flow) from the heart to the lung during ventricular contraction.

Patent Document 1 described above further discloses a technology of separately using filters in such a manner that the processing using a highpass filter is performed in blood flow analysis and the processing using a lowpass filter is performed in ventilatory analysis to prevent the blood flow and respiration from affecting each other and prevent the density values thereof from affecting each other, thereby accurately extracting respiration and blood flow using an inter-filter difference.

PRIOR ART DOCUMENTS

Patent Documents

Patent Document 1: Japanese Patent Application Laid-Open No. 2012-110399
Patent Document 2: Japanese Patent Application Laid-Open No. 2003-249398
Patent Document 3: Japanese Patent Application Laid-Open No. 2004-312434
Patent document 4: WO2007/078012

SUMMARY OF THE INVENTION

Problems to be Solved by the Invention (First Circumstance)

In blood flow analysis using an X-ray dynamic image of the chest, the following is considered. In a maximum inspiration state, a phenomenon in which a blood flow through blood vessels is attenuated occurs because, for example, the blood vessel in the lung is pressed, resulting in a blood-flow-analysis value acquired by blood flow analysis that is smaller than an original value. In particular, a peripheral blood vessel apt to form a blood clot suffers from the above-mentioned phenomenon of an attenuated blood flow, and besides, originally has a small blood flow amount. For these reasons, the blood flow becomes difficult to be seen, and thus, is highly likely to be indistinguishable from a blood clot, which conceivably decreases the performance of finding a blood clot.

In the conventional technology of Patent Document 1 above, the effects of ventilation are eliminated as irrelevant information for a blood flow, and the effects of blood flow are eliminated as irrelevant information for ventilation. Consequently, blood flow analysis suitable for dynamic diagnosis may not be performed when the above-mentioned phenomenon occurs.

The conventional technology of Patent Document 2 can maximize an amount of information necessary for dynamic diagnosis by controlling an X-ray source in accordance with a respiratory period. This technology, however, is aimed to test the movement of the tissues of the lung and the diaphragm and is not aimed to analyze a blood flow. Besides, Patent Document 2 discloses nothing about blood flow analysis.

(Second Circumstance)

For in-depth blood flow analysis by the conventional technologies of Patent Documents 3 and 4 above, photographing is desirably performed while the test subject is holding breath, with effects of respiration being eliminated.

A dynamic image photographed during breath holding has no changes in the movement inside the king field and the shape of the lung field. Unfortunately, this prevents ventilatory analysis from being performed simultaneously with blood flow analysis. To perform a blood flow analysis and ventilatory analysis, thus, two patterns of photographing are necessary: photographing during breath holding for blood flow analysis and photographing of the states of natural respiration and forced respiration for ventilatory analysis. Photographing of the both patterns needs the periods and the number of seconds for photographing (the number of frame images) required for each analysis, leading to a longer time for photographing per se, which increases an amount of exposure.

In the conventional technology of Patent Document 1, the effects of ventilation are eliminated as irrelevant information for a blood flow, and the effects of blood flow are eliminated as irrelevant information for ventilation, and thus, photographing merely needs one pattern of photographing of a moving image in respiration. This photographing, however, does not reflect effects to be exerted on a blood-flow-analysis value depending on a phase state, namely, an inspiration phase state or the expiration phase state of respiration (described below in detail). This may decrease the accuracy of blood flow analysis.

The present invention has been made in view of the first circumstance above and has an object to provide an image processing technology capable of acquiring a highly accurate, appropriate blood-flow-analysis value and also preventing a decrease in the performance of finding a blood clot through dynamic diagnosis.

Further, the present invention has been made in view of the second circumstance above and has another object to provide an image processing technology capable of acquiring a highly accurate blood-flow-analysis value that reflects the phase states of respiration (an inspiration phase state and an expiration phase state).

Means to Solve the Problems

In consideration of the first circumstance, to solve at least one of the problems, a first aspect of the present invention relates to an image processing apparatus that performs a blood flow analysis, which includes moving image acquiring unit respiratory information acquiring unit, blood-flow-restricted time determining unit, and blood flow analysis correcting unit. The moving image acquiring unit acquires a moving image unit including a plurality of frame images sequentially capturing, in a time direction, a state in which a blood flow of a target region inside a body of a human or an animal changes. The respiratory information acquiring unit performs a respiratory information acquiring processing of acquiring respiratory information in the body synchronized at times at which the frame images are captured. The blood-flow-restricted time determining unit performs a blood-flow-restricted time determining processing of determining on the basis of the respiratory information, a blood-flow-restricted time indicating a time at which the blood flow of the target region is assumed to be restricted due to respiration. The blood flow analysis correcting unit performs a blood-flow-analysis content correcting processing of excluding the frame image captured at the blood-flow-restricted time from targets for blood flow analysis or decreasing the blood-flow-analysis importance of the frame image compared with another time period.

In consideration of the second circumstance, to solve at least one of the problems, a second aspect of the present invention relates to an image processing apparatus including moving image acquiring unit, respiratory information acquiring unit, phase state judging unit, analysis range setting unit, and blood-flow-analysis value calculating unit. The moving image acquiring unit acquires a moving image including a plurality of frame images sequentially capturing, in a time direction, a state in which a blood flow of a target region inside a body of a human or an animal changes. The respiratory information acquiring unit performs a respiratory information acquiring processing of acquiring respiratory information in the body synchronized at times at which the frame images are captured. The phase state judging unit judges to which of an inspiration phase state and an expiration phase state the respiratory information belongs and acquires a phase state judgment result. The analysis range setting unit performs an analysis range setting processing of setting a blood-flow-analysis range in at least one of the inspiration phase state and the expiration phase state on the basis of the respiratory information and the phase state judgment result. The blood-flow-analysis value calculating unit performs a blood-flow-analysis value calculating processing of performing a blood flow analysis on the frame images in the blood-flow-analysis range to acquire a blood-flow-analysis value.

Effects of the Invention

In the image processing apparatus of the first aspect, the blood-flow-restricted time determining unit sets a blood-flow-restricted time on the basis of respiratory information. The blood flow analysis correcting unit performs the blood-flow-analysis content correcting processing of eliminating a frame image captured at the blood-flow-restricted time from targets for blood flow analysis or decreasing the blood-flow-analysis importance of the frame image compared with another time period. Thus, blood flow analysis involving the blood-flow-analysis content correcting processing is enabled, preventing a blood-flow-analysis value from becoming an abnormal value due to respiration. A highly accurate, appropriate blood-flow-analysis value can thus be acquired. This prevents a decrease in the performance of finding a blood clot, enabling appropriate, efficient dynamic diagnosis of a blood flow.

The image processing apparatus of the second aspect sets a blood-flow-analysis range in at least one of the inspiration phase state and the expiration phase state on the basis of the respiratory information and the phase state judgment result, and performs a blood flow analysis on the frame images in the blood-flow-analysis range to acquire a blood-flow-analysis value in the at least one state. Thus, a blood-flow-analysis value that corresponds to at least one of the inspiration phase state and the expiration phase state desired by the user, that is, a blood-flow-analysis value that reflects the phase state of respiration, can be acquired. This enables appropriate, efficient image diagnosis of a blood flow.

BRIEF DESCRIPTION OF DRAWINGS

FIG. 5 is a schematic diagram illustrating contour extraction of a lung field region.

FIG. 6 is a schematic diagram illustrating positions of feature points of the lung field region.

FIG. 7 is a schematic diagram showing waveform data of respiratory information in time sequence.

FIG. 18 is a flowchart explaining the basic operation of the image processing apparatus 3A achieved in the second embodiment.

FIG. 23 is a block diagram showing the functional configuration of an image processing apparatus 3C according to a fourth embodiment.

FIG. 37 is a diagram explaining the relationship between a respiratory phase and a cardiac phase.

FIG. 38 is a block diagram showing the functional configuration of an image processing apparatus 3 according to the sixth embodiment.

FIG. 40 is a schematic diagram showing waveform data of respiratory information in time series.

FIG. 41 is a schematic diagram illustrating changes of the cardiac wall.

FIG. 43 is a schematic diagram illustrating a partial waveform measured with an electrocardiograph.

FIG. 47 is a diagram explaining a blood-flow-analysis value calculating processing.

FIG. 48 is another diagram explaining the blood-flow-analysis value calculating processing.

FIG. 49 is still another diagram explaining the blood-flow-analysis value calculating processing.

FIG. 53 is a diagram showing another example of the diagnostic purpose range.

DESCRIPTION OF EMBODIMENTS

1. First Embodiment

A radiographic dynamic image capturing system according to a first embodiment of the present invention will be described below.

<1-1. Overall Configuration of Radiographic Dynamic Image Photographing System>

The radiographic dynamic image capturing system according to the first embodiment captures a radiographic image of a target region of a subject that is a human body or an animal body in a situation in which a physical state of the subject in a target region changes periodically over time.

Figure 1:
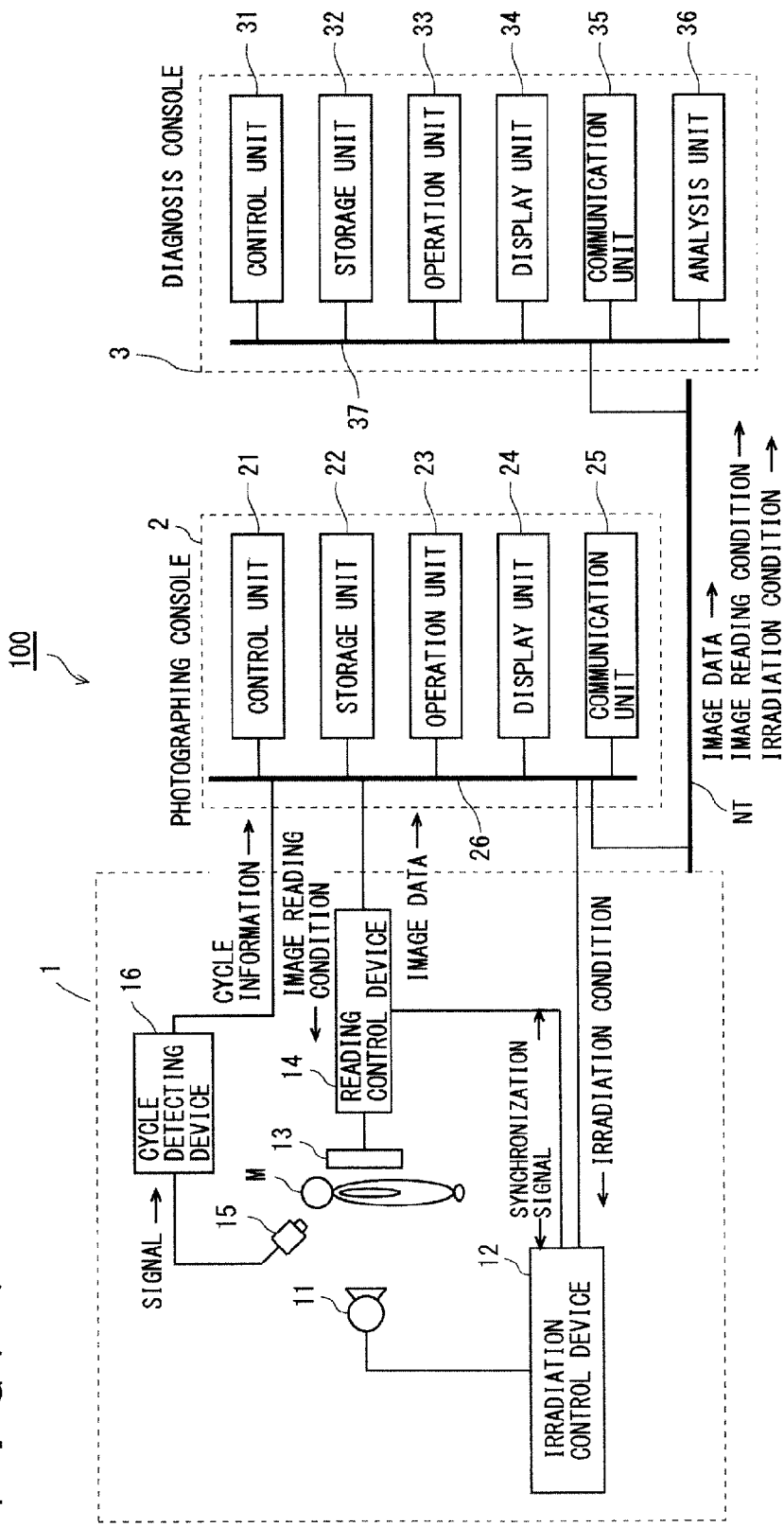
FIG. 1 is a diagram showing the overall configuration of a radiographic dynamic image capturing system 100 according to a first embodiment.

FIG. 1 is a diagram showing the overall configuration of the radiographic dynamic image capturing system according to the first embodiment. As shown in FIG. 1, a radiographic dynamic image capturing system 100 includes a photographing apparatus 1, a photographing control apparatus 2 (photographing console), and an image processing apparatus 3 (diagnosis console). The photographing apparatus 1 is connected with the photographing control apparatus 2 by a communication cable or the like, and the photographing control apparatus 2 is connected with the image processing apparatus 3 through a communication network NT such as a local area network (LAN). These apparatuses constituting the radiographic dynamic image capturing system 100 comply with the digital image and communications in medicine (DICOM) standard and communicate with each other in accordance with the DICOM standard.

<1-1-1. Configuration of Photographing Apparatus 1>

The photographing apparatus 1 is configured, for example, of an X-ray photographing apparatus or the like, and photographs dynamic states of the chest of a subject M involved in respiration. The dynamic state is photographed by acquiring a plurality of images in time sequence while repeatedly irradiating the chest of the subject M with radiation such as X-rays. A series of images acquired through the continuous photographing is referred to as a dynamic image (moving image). Each of the images constituting the dynamic image is referred to as a frame image. In this embodiment, a blood flow analysis is performed on the basis of these images, and a respiration waveform (respiratory phase) is obtained.

As shown in FIG. 1, the photographing apparatus 1 includes an irradiation unit (radiation source) 11, an irradiation control device 12, an imaging unit (radiation detecting unit) 13, a reading control device 14, a cycle detecting sensor 15, and a cycle detecting device 16.

The irradiation unit 11 irradiates the subject M with radiation (X-rays) under control of the irradiation control device 12. Illustrated as an example is a system for a human body, and test subject M corresponds to a test target. The test subject M is also referred to as a "test subject" below.

The irradiation control device 12 is connected to the photographing control apparatus 2 and controls the irradiation unit 11 on the basis of an irradiation condition input from the photographing control apparatus 2 for radiography.

The imaging unit 13 is configured of a semiconductor image sensor such as an FPD and converts radiation, which has been emitted from the irradiation unit 11 and has passed through the test subject M, into an electrical signal (image information).

The reading control device 14 is connected to the photographing control apparatus 2. The reading control device 14 controls switching units of pixels of the imaging unit 13 on the basis of an image reading condition input from the photographing control apparatus 2 to switch reading of the electrical signals stored in the pixels, and reads the electrical signals stored in the imaging unit 13 to acquire image data. The reading control device 14 then outputs the acquired image data (frame image) to the photographing control apparatus 2. Examples of the image reading condition include a frame rate, a frame interval, a pixel size, and an image size (matrix size). The frame rate is the number of frame images acquired per second and matches a pulse rate. The frame interval is a time from the start of an operation to acquire one frame image to the start of an operation to acquire the next frame image in continuous photographing, and matches a pulse interval.

The irradiation control device 12 and the reading control device 14 are herein connected to each other, and exchange synchronization signals with each other to synchronize an irradiation operation and an image reading operation with each other.

The cycle detecting device 16 detects a respiratory cycle of the test subject M and outputs the respiratory information to a control unit 21 of the photographing control apparatus 2. The cycle detecting device 16 includes, for example, a cycle detecting sensor 15 that detects the movement of the chest of the subject M (the respiratory cycle of the subject M) through laser irradiation, and a time measurement unit (not shown) that measures a time of the respiratory cycle detected by the cycle detecting sensor 15 and outputs the time to the control unit 21.

<1-1-2. Configuration of Photographing Control Apparatus 2>

The photographing control apparatus 2 outputs the irradiation condition and the image reading condition to the photographing apparatus 1 to control radiography and a radiographic image reading operation performed by the photographing apparatus 1, and also displays a dynamic image acquired by the photographing apparatus 1 so that a radiographer can check positioning and whether the dynamic image is an image suitable for diagnosis.

As shown in FIG. 1, the photographing control apparatus 2 includes the control unit 21, a storage unit 22, an operation unit 23, a display unit 24, and a communication unit 25, and these units are connected to one another by a bus 26.

The control unit 21 is configured of a central processing unit (CPU), a random access memory (RAM), and the like. The CPU of the control unit 21 reads a system program and various processing programs stored in the storage unit 22 in response to an operation of the operation unit 23 to develop them in the RAM, and performs various processings such as photographing control processing, which will be described below, in accordance with the developed program to perform centralized control of an operation of each unit of the photographing control apparatus 2 and an operation of the photographing apparatus 1.

The storage unit 22 is configured of a nonvolatile semiconductor memory, a hard disk, and the like. The storage unit 22 stores various programs to be executed by the control unit 21 and parameters required for the programs to perform processings, or data on the processing result, and the like.

The operation unit 23 includes a keyboard including cursor keys, numeric keys, and various function keys, and a pointing device such as a mouse, and outputs an instruction signal input through a key operation made on the keyboard, a mouse operation, or a touch panel to the control unit 21.

The display unit 24 is configured of a monitor such as a color liquid crystal display (LCD) and displays an input instruction, data, or the like from the operation unit 23, in accordance with an instruction of a display signal input from the control unit 21.

The communication unit 25 includes a LAN adapter, a modem, and a terminal adapter (TA) and controls data transmission/reception with each device connected to the communication network NT.

<1-1-3. Configuration of Image Processing Apparatus 3>

The image processing apparatus 3 acquires a dynamic image transmitted from the photographing apparatus 1 through the photographing control apparatus 2 and displays an image to be used for a doctor or the like to make diagnosis through reading.

As shown in FIG. 1, the image processing apparatus 3 includes a control unit 31, a storage unit 32, an operation unit 33, a display unit 34, a communication unit 35, and an analysis unit 36, and these units are connected to one another by a bus 37.

The control unit 31 is configured of a CPU, a RAM, and the like. The CPU of the control unit 31 reads a system program and various processing programs stored in the storage unit 32 in response to an operation of the operation unit 33 to develop them in the RAM, and performs various processings in accordance with the developed program to perform centralized control of an operation of each unit of the image processing apparatus 3 (described below in detail).

The storage unit 32 is configured of a nonvolatile semiconductor memory, a hard disk, and the like. The storage unit 32 stores various programs to be executed by the control unit 31 and parameters required for the programs to perform processing, or data on the processing result, and the like. For example, the storage unit 32 stores an image processing program for performing image processing, which will be described below. These various programs are stored in the form of readable program codes, and the control unit 31 sequentially performs operations according to the program codes.

The operation unit 33 includes a keyboard including cursor keys, numeric keys, and various function keys, and a pointing device such as a mouse, and outputs an instruction signal input through a key operation made on the keyboard, a mouse operation, or a touch panel to the control unit 31.

The display unit 34 is configured of a monitor such as a color LCD, and displays an input instruction and data from the operation unit 33, and a display image, which will be described below, in accordance with an instruction of a display signal input from the control unit 31.

The communication unit 35 includes a LAN adapter, a modem, and a TA, and controls data transmission/reception with each device connected to the communication network NT.

The analysis unit 36 analyzes a blood flow on the basis of a dynamic image transmitted from the photographing apparatus 1 under the control of the control unit 31.

<1-2. General Characteristics of Respiratory Phase and Problem with Blood-Flow-Analysis Value>

The general characteristics of a respiratory phase and the problem with a blood-flow-analysis value obtained through blood flow analysis will be described as the premise of the detailed description of the image processing apparatus 3 in this embodiment.

Figure 2:
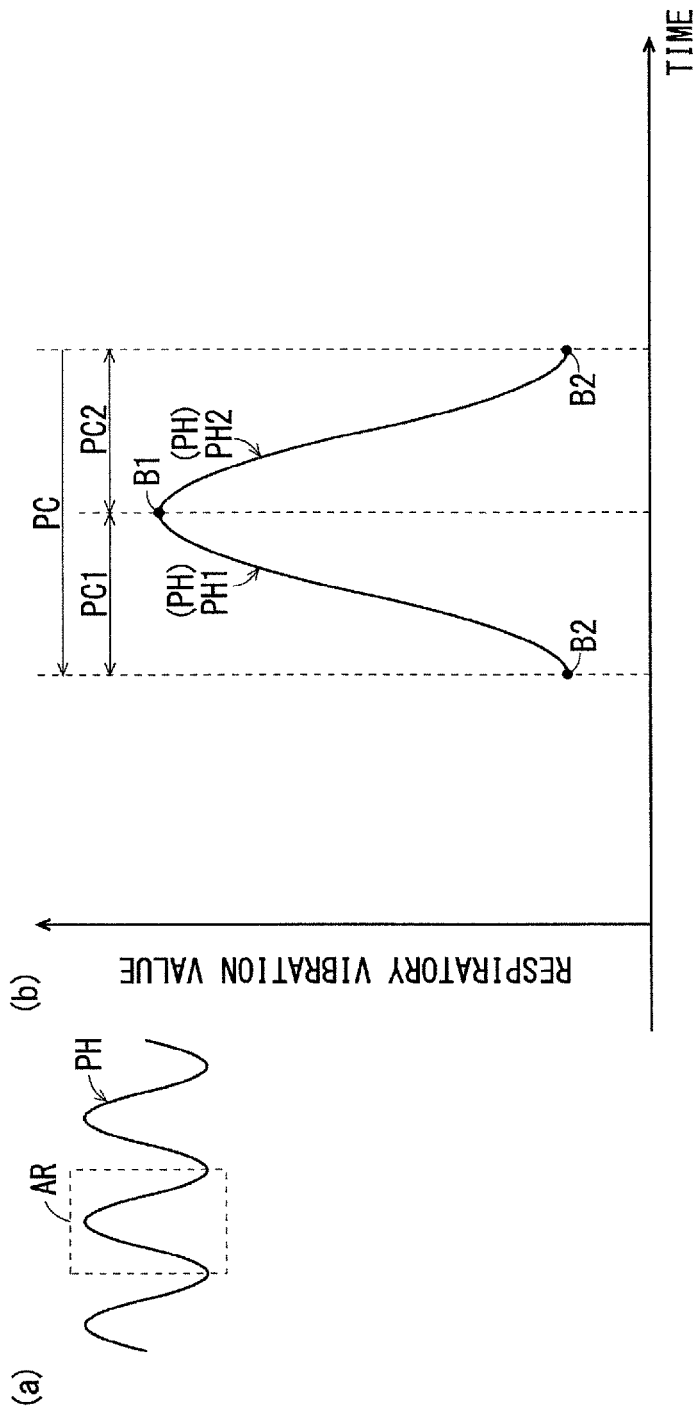
FIG. 2 is a diagram explaining respiratory phases.

FIG. 2 is a diagram illustrating the general characteristics of a respiratory phase, where part (a) of FIG. 2 shows a partial waveform of a respiratory phase, and part b) of FIG. 2 shows a respiratory phase in a region AR (for one period) of part (a) of FIG. 2. The horizontal axis represents a time (in a time direction) at which a moving image is captured, and the vertical axis represents a respiratory vibration value described below (described below in detail).

As shown in part (b) of FIG. 2, a respiratory phase PH for one period PC has a maximum inspiration phase B1 and a maximum expiration phase B2 (described below in detail). The phase from the maximum expiration phase B2 to the maximum inspiration phase B is referred to as an inspiration phase PH1, and the phase from the maximum inspiration phase B1 to the maximum expiration phase B2 is referred to as an expiration phase PH2. In other words, assuming that the first half period PC1 and the second half period PC2 of one period PC are the inspiration phase PH1 and the expiration phase PH2, respectively, the first half period PC1 is generally equal to the second half period PC2 in healthy people.

At the maximum inspiration phase B1, a phenomenon in which a blood flow through the blood vessels in the lung field region is attenuated occurs. The following two are conceivable factors that attenuate a blood flow.

(i) Blood vessel compression: In the maximum inspiration state, an increased external pressure on the blood vessel inside the lung makes a blood flow less likely to run through, whereby the blood flow becomes less conspicuous in a frame image.

(ii) Blood vessel expansion: In the maximum inspiration state, the lung is inflated, and a blood vessel is stretched more to become thinner than in the original state, whereby the blood flow becomes less conspicuous in a frame image.

Thus, if a blood flow analysis is performed in a single operation on data to be analyzed, at the time of the maximum inspiration phase B1, a blood-flow-analysis value obtained by blood flow analysis becomes smaller than an original value, and a normal value may not be obtained.

A peripheral blood vessel apt to form a blood clot suffers from a phenomenon in which a blood flow is attenuated, and besides, originally has a small blood flow amount. In the maximum inspiration state, therefore, the blood flow becomes difficult to be seen, and accordingly, is highly likely to be indistinguishable from a blood clot. This decreases the performance of finding a blood clot, and accordingly, dynamic diagnosis of a blood flow cannot be performed appropriately and efficiently.

Under such circumstances, dynamic diagnosis is desired, which prevents false diagnosis due to an abnormal blood-flow-analysis value associated with respiration and thus can find a blood clot appropriately.

Configurations described below can obtain an appropriate blood-flow-analysis value by reflecting a time (timing) at which a blood flow is attenuated as described above and can also prevent a decrease in the performance of finding a blood clot through dynamic diagnosis. In the description below, the above-mentioned attenuation of a blood flow is expressed as that "a blood flow is restricted" or as "a restriction of a blood flow." In the descriptions of the present invention and this embodiment, the term "time" does not necessarily mean a specific period of time. The term "time" is used for convenience' sake to represent a predetermined timing, a moment, or the like. For example, the term "time"

is used as an expression including a specific moment during a period of time elapsed from a start of measurement or a specific timing during an elapsed period of time measured from the start being a predetermined timing on a time axis.

Details of the image processing apparatus 3 in the first embodiment will be described below.

<1-3. Specific Configuration of Image Processing Apparatus 3>

The image processing apparatus 3 of the radiographic dynamic image capturing system 100 in the first embodiment of the present invention acquires a blood-flow-analysis value in consideration of a time (timing) at which a blood flow is restricted, and thus, can perform dynamic diagnosis of a blood flow appropriately and efficiently.

The functional configuration achieved by the image processing apparatus 3 will now be described.

<1-3-1. Functional Configuration of Image Processing Apparatus 3>

Figure 3:
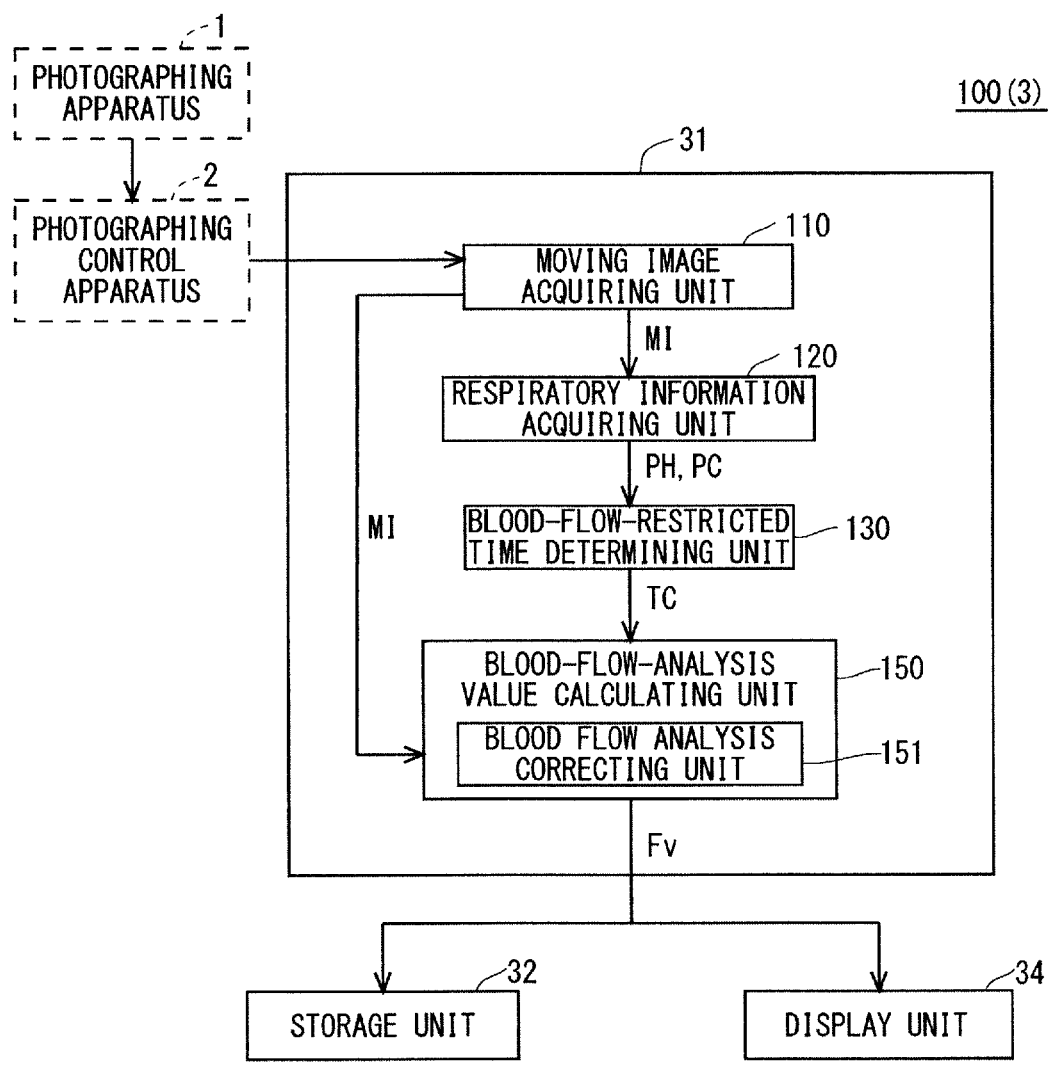
FIG. 3 is a block diagram showing the functional configuration of an image processing apparatus 3 according to the first embodiment.

FIG. 3 is a diagram showing the functional configuration achieved by the control unit 31 through an operation of the CPU or the like in accordance with various programs in the image processing apparatus 3 of the radiographic dynamic image capturing system 100, as well as other configurations. The image processing apparatus 3 in this embodiment uses a dynamic image in which the chest mainly including the heart and both lungs is photographed.

The control unit 31 is mainly composed of a moving image acquiring unit 110, a respiratory information acquiring unit 120, a blood-flow-restricted time determining unit 130, a blood-flow-analysis value calculating unit 150, and a blood flow analysis correcting unit 151.

Although the following description is given on the assumption that the functional configuration of the control unit 31 as shown in FIG. 3 is achieved through execution of a preinstalled program, the functional configuration may be achieved by a dedicated hardware configuration.

Details of the processings performed by the moving image acquiring unit 110, the respiratory information acquiring unit 120, the blood-flow-restricted time determining unit 130, the blood-flow-analysis value calculating unit 150, and the blood flow analysis correcting unit 151 are sequentially described with reference to FIG. 3.

<1-3-1-1. Moving Image Acquiring Unit 110>

The moving image acquiring unit 110 acquires a moving image composed of a plurality of frame images that have been photographed by the reading control device 14 of the photographing apparatus 1 and in which how a blood flow of a target region in the test subject M changes has been sequentially photographed in the time direction. The target region in this embodiment is a region targeted for blood flow analysis, and a blood vessel region in a lung field region is assumed here. In other words, as shown in FIG. 3, the photographing control apparatus 2 is located between the photographing apparatus 1 and the image processing apparatus 3, and detected data (a plurality of frame images) stored in the storage unit 22 of the photographing control apparatus 2 is output to the communication unit 35 of the image processing apparatus 3 through the communication unit 25.

Figure 4:
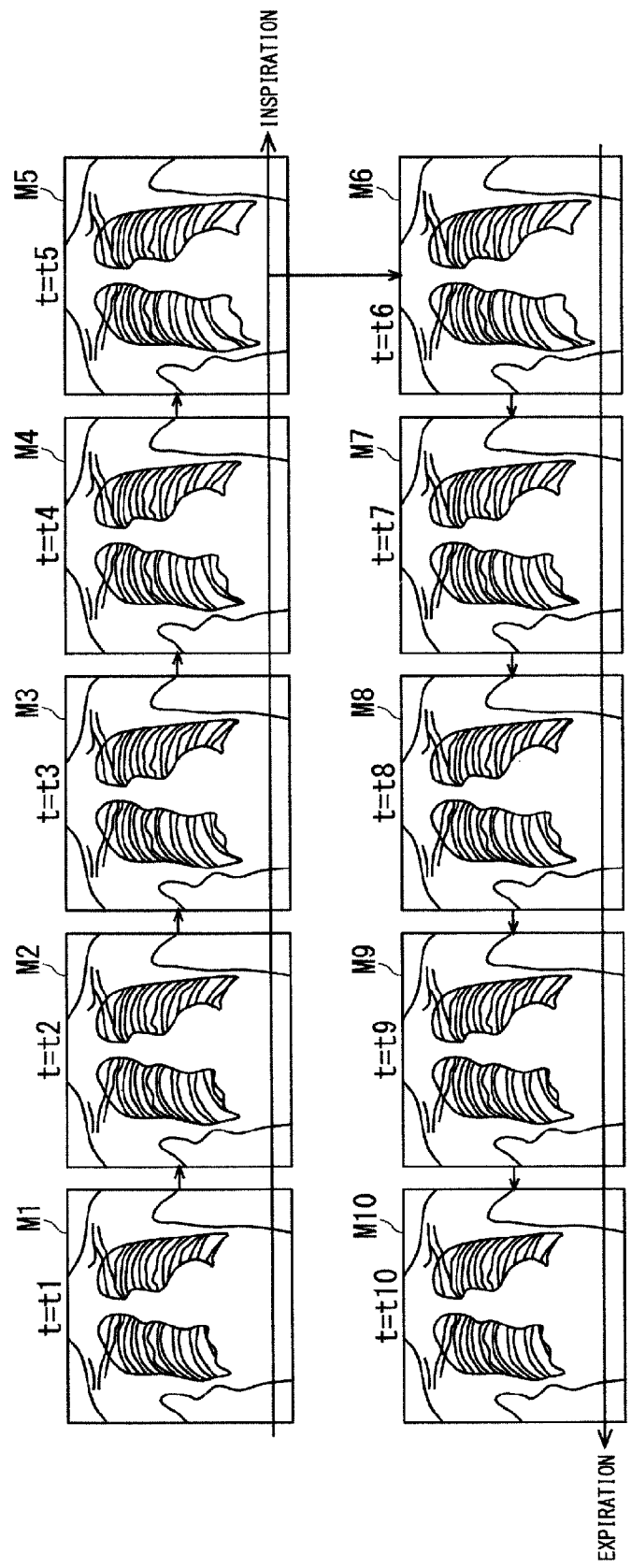
FIG. 4 is a diagram illustrating dynamic images captured by radiographic dynamic image photography.

FIG. 4 is a diagram illustrating a moving image captured, for a dynamic state of the chest of the test subject M involved in respiration, through radiographic dynamic image photographing. As shown in FIG. 4, frame images M1 to M10 acquired by the moving image acquiring unit 110 are obtained by continuously photographing one period of the respiratory cycle at constant photographing timings. Specifically, images captured at photographing timings, a time t=t1, t2, t3, . . . , and t10 correspond to the frame images M1, M2, M3, . . . , and M10, respectively. As described below, a blood flow of the chest of the test subject M is analyzed using the frame images M1 to M10 (MI) shown in FIG. 4, and the information on respiration of the test subject M can be obtained on the basis of the frame image MI.

<1-3-1-2. Respiratory Information Acquiring Unit 120>

The respiratory information acquiring unit 120 performs a respiratory information acquiring processing of acquiring respiratory information in the test subject M that has synchronized at a time at which the frame image MI is captured.

The respiratory information acquiring processing is broadly divided into two types of processings, which will now be described separately.

<1-3-1-2-1. First Respiratory Information Acquiring Processing: Respiratory Vibration Value>

The first respiratory information acquiring processing is a processing of acquiring respiratory vibration values indicated as physical change values of the lung field region of the subject M as respiratory information. The respiratory vibration values herein can be obtained on the basis of, for example, a plurality of frame images MI constituting a moving image acquired by the moving image acquiring unit 110.

As shown in FIG. 3, in the first respiratory information acquiring processing, the respiratory information acquiring unit 120 calculates respiratory vibration values using a plurality of frame images MI acquired by the moving image acquiring unit 110. Specifically, the respiratory vibration value is an indicator corresponding to a change in the size of the lung field region associated with respiration. Examples of such a value include "a distance between feature points of the lung field region (such as a distance from the apical portion of the lung to the diaphragm," "an area value of the lung field portion (the size of the lung field region)," "an absolute position of the diaphragm," and "a pixel density value of the lung field region." Description will be given of an example in which the respiratory vibration value is "an area value of a lung field portion" and "a distance between feature points of the lung field region."

In the case where the respiratory vibration value is the "area value of the lung field portion," contour extraction of the lung field portion can be performed to define the number of pixels in the region surrounded by the contour as an area of the lung field portion.

FIG. 5 is a schematic diagram illustrating contour extraction of the lung field portion. As shown in FIG. 5, the lung field portion may be extracted for each of the left and the right (see part (a) of FIG. 5) or may be extracted as a contour including the regions of the heart and the spine (see part (b) of FIG. 5). Conventional technologies (for example, see "Image feature analysis and computer-aided diagnosis: Accurate determination of ribcage boundary in chest radiographs," Xin-Wei Xu and Kunio Doi, Medical Physics, Volume 22(5), May 1995, pp. 617-626) may be employed as an extraction method.

As described above, the respiratory information acquiring unit 120 extracts a contour OL of the lung field region with the use of the plurality of frame images MI acquired and detects the number of pixels in the extracted region as an area value of the lung field portion, thereby acquiring respiratory vibration values. Then, changes in the respiratory vibration value are taken as a respiratory phase PH, and a respiratory period PC is detected (see FIG. 7 described below).

In the case where a respiratory vibration value is "the distance between feature points of the lung field region," the distance between feature points of the lung field region is calculated with the use of a plurality of frame images MI. In other words, the lung field portion is extracted as in the manner described above, and two feature points are obtained from the extracted region. Then, the distance between the two points is obtained, which is detected as a respiratory vibration value. A change in the distance between the feature points (respiratory vibration value) is taken as a respiratory phase PH.

FIG. 6 is a diagram illustrating positions of the feature points of the lung field region in the case where the contour OL of the lung field portion of part (a) of FIG. 5 is used. In calculation of a change in the length (lung field length) from an upper end LT to a lower end LB in the lung region, part (a) of FIG. 6 shows an example in which extraction is performed with the apical portion of the lung being the upper end LT of the lung region and with an intersection of a straight line drawn from the apical portion of the lung in a body axis direction and the diaphragm being the lower end LB of the lung region, and part (b) of FIG. 6 shows an example in which extraction is performed with the apical portion of the lung being the upper end LT of the lung region and with the costophrenic angle being the lower end LB of the lung region.

As described above, the respiratory information acquiring unit 120 extracts the contour OL of the lung field region with the use of a plurality of frame images M1 acquired and detects the distance between the feature points from the lung field region, thereby acquiring respiratory vibration values. Then, with changes in the respiratory vibration value as a respiratory phase PH, the respiratory period PC is detected (see FIG. 7 described below).

FIG. 7 is a schematic diagram of a respiratory phase PH, which indicates the waveform data on the respiratory vibration values detected by the respiratory information acquiring unit 120 in time sequence. FIG. 7 shows the results obtained by calculating respiratory vibration values such as an area value of the lung field region and a distance between feature points and monitoring the calculated values in the time direction per photographing timing TM. The vertical arrow shown in FIG. 7 indicates an amplitude direction AP of the respiratory phase PH.

As shown in FIG. 7, one respiratory period (respiratory cycle) PC is composed of inspiration and expiration, one expiration and one inspiration. In inspiration, the region of the lung field in the rib cage becomes larger as the diaphragm descends for inhaling. The time of inhaling to the maximum extent (a switching point from inspiration to expiration) is a maximum inspiration time B1. In exhalation, the region of the lung field becomes smaller as the diaphragm ascends for exhaling. The time of exhaling to the maximum extent (a switching point from expiration to inhalation) is a maximum expiration time B2.

There may be employed a method of measuring respiratory vibration values by separate equipment. For example, the apparatus described in Japanese Patent No. 3793102 may be used. Alternatively, for example, the monitoring technique using the laser light and the sensor composed of a CCD camera is adoptable (see, for example, "A study on respiration monitoring of a sleeping person with FG vision sensor", Hirooki Aoki, Masato Nakajima, The Institute of Electronics, Information and Communication Engineers, Society Conference, Proceedings 2001, Information, System Society Conference Report, pp. 320 and 321, 2001/08/29).

In this embodiment, as shown in FIG. 1, the cycle detecting sensor 15 of the cycle detecting device 16 can be used. Other examples of the method of detecting a respiratory vibration value include the method of detecting the movement of the chest of a subject with a respiration monitoring belt, and the method of detecting an air flow of respiration with an air flow meter. Those methods are also applicable.

<1-3-1-2-2. Second Respiratory Information Acquiring Processing: Relative Respiration Value>

The second respiratory information acquiring processing is the processing of acquiring, as respiratory information, relative respiration values indicating relative values for enabling judgment about to which of the inspiration phase PH1 and the expiration phase PH2 of the test subject M the phase belongs, independently of a moving image.

Figure 33:
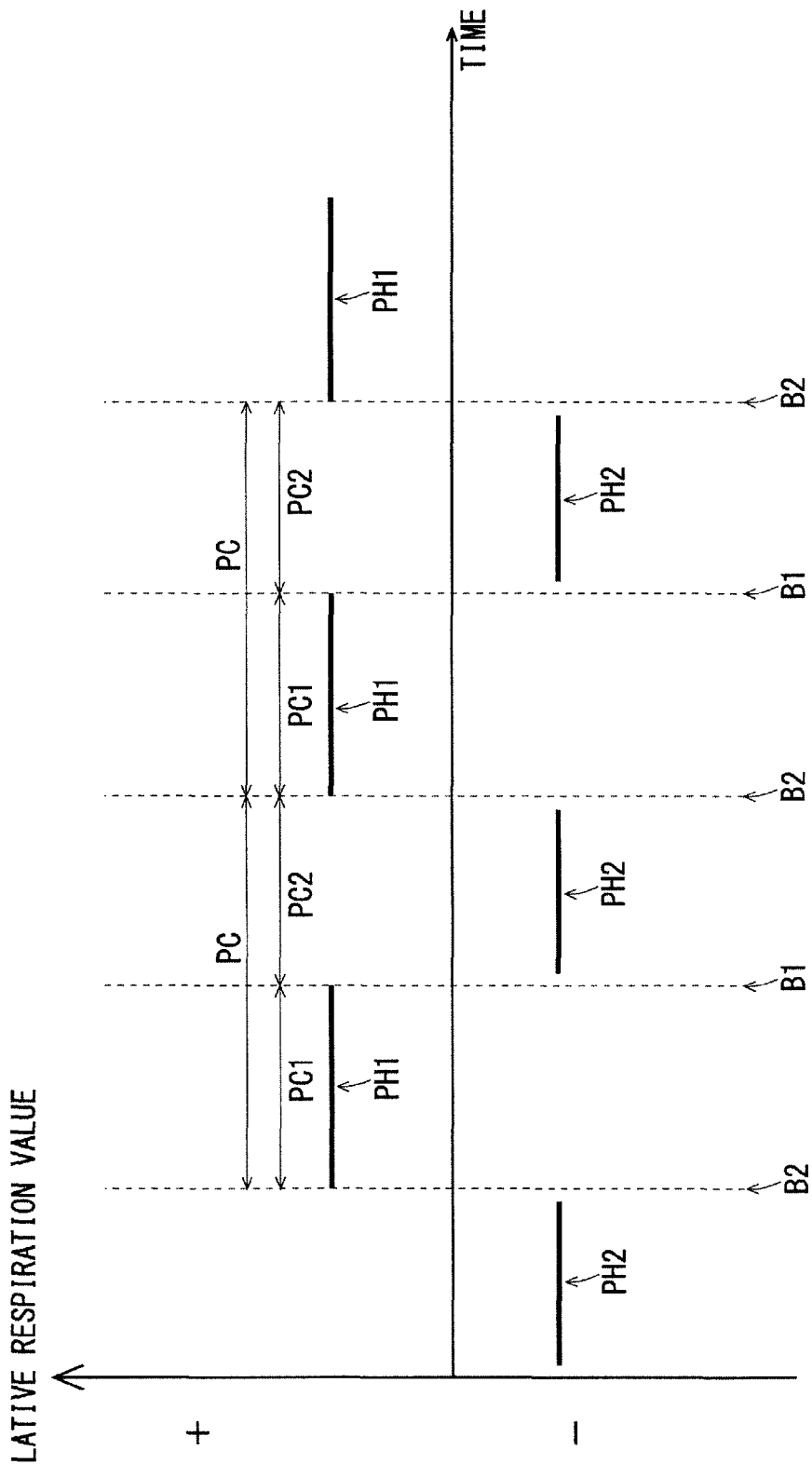
FIG. 33 is a diagram explaining relative respiration values.

FIG. 33 is a diagram illustrating relative respiration values, where the horizontal axis represents a time at which a moving image is captured and the vertical axis represents a relative respiration value. As shown in FIG. 33, a positive relative respiration value corresponds to the inspiration phase PH1, and a negative relative respiration value corresponds to the expiration phase PH2. A boundary at which a relative respiration value changes from the inspiration phase PH1 to the expiration phase PH2 corresponds to a maximum inspiration phase B1, and a boundary at which a relative respiration value changes from the expiration phase PH2 to the inspiration phase PH1 corresponds to a maximum expiration phase B2. Herein, description has been given of an example of relative respiration values with reference to FIG. 33. Alternatively, in practice, the relative respiration values may not necessarily be positive and negative values but may be values for enabling judgment about to which of the inspiration phase PH1 and the expiration phase PH2 the phase belongs.

Relative respiration values can be acquired from the measurement result from separate equipment. For example, the separate equipment, whose configuration is changed to output a positive value for a measured value not less than a predetermined threshold and output a negative value for a measured value less than the threshold, can acquire relative respiration values. In other words, assumed here is the case where respiratory information is acquired externally in synchronization with capturing of a moving image of a plurality of frame images MI, and a respiratory period PC is recognizable from the relative respiration values.

As described above, the respiratory information acquiring unit 120 acquires a plurality of frame images MI through the moving image acquiring unit 110 and also acquires relative respiration values synchronized with the plurality of frame images MI, thereby detecting a respiratory period PC on the basis of the relative respiration values (see FIG. 3).

<1-3-1-3. Blood-Flow-Restricted Time Determining Unit 130>

The blood-flow-restricted time determining unit 130 performs blood-flow-restricted time determining processing of determining a blood-flow-restricted time indicating, for example, a time or timing at which a blood flow of a target region is restricted along with respiration, on the basis of respiratory information (see FIG. 3).

The blood-flow-restricted time determining processing is broadly divided into three types of processings, which will now be described separately.

<1-3-1-3-1. First Blood-Flow-Restricted Time Determining Processing: Maximum Value>

A first blood-flow-restricted time determining processing is a processing of setting a time at which a respiratory vibration value reaches a maximum value as a blood-flow-restricted time.

Figure 8:
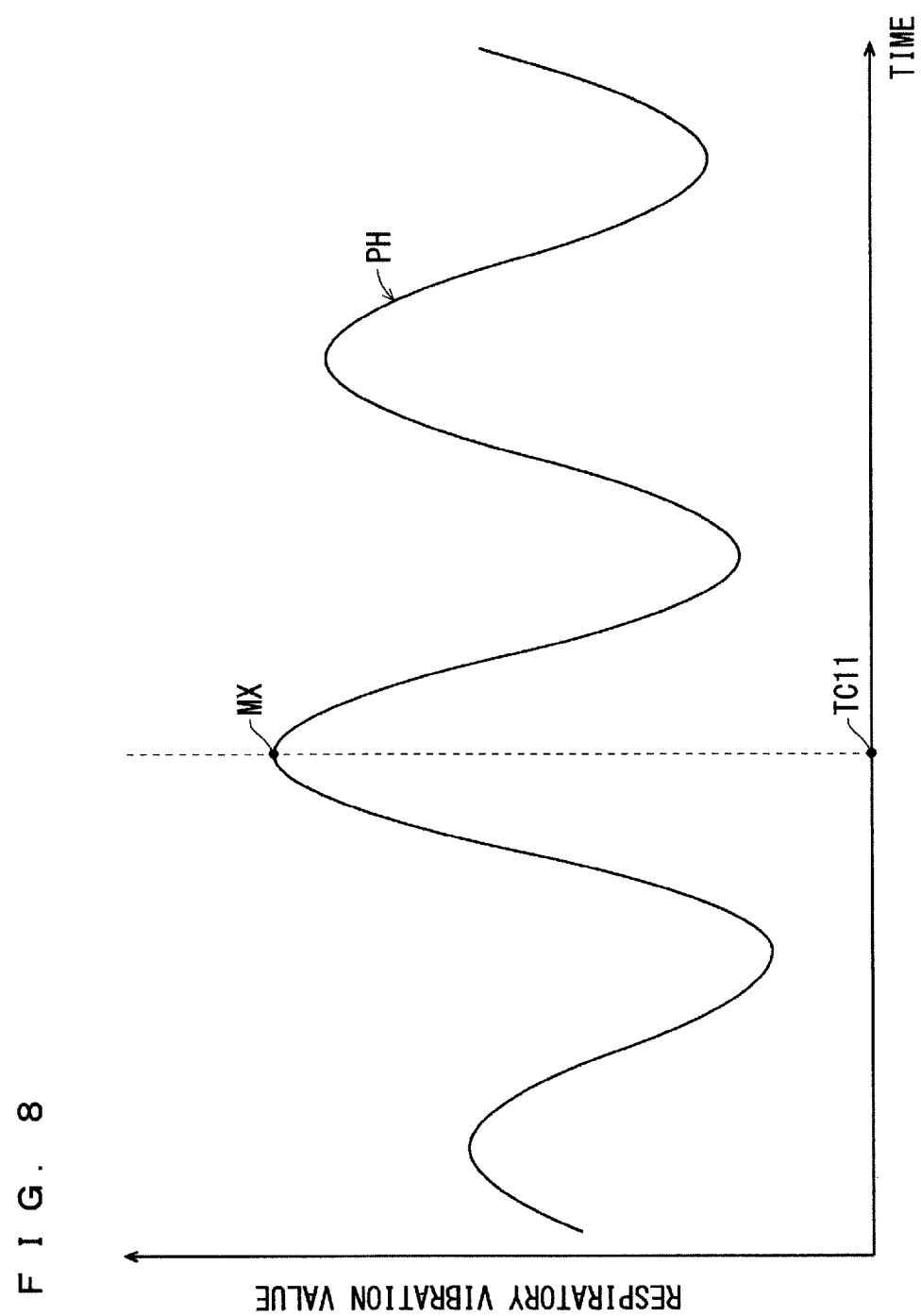
FIG. 8 is a diagram explaining a blood-flow-restricted time determining processing.

FIG. 8 is a diagram explaining the first blood-flow-restricted time determining processing, where the vertical axis represents a respiratory vibration value, and the horizontal axis represents a time at which a moving image is captured. As shown in FIG. 8, the blood-flow-restricted time determining unit 130 sets, as a blood-flow-restricted time TC11 (TC), a time corresponding to a maximum value MX among the respiratory vibration values acquired from a plurality of frame images MI being targets for dynamic diagnosis.

<1-3-1-3-2. Second Blood-Flow-Restricted Time Determining Processing: Maximum Inspiration Phase>

A second blood-flow-restricted time determining processing, which enables (i) recognition of a respiratory period PC from respiratory vibration values (see FIG. 2), is the processing of setting a time at which a respiratory vibration value reaches a maximum value as a blood-flow-restricted time TC per respiratory period PC. Or, the second blood-flow-restricted time determining processing, which enables (ii) recognition of a respiratory period PC from relative respiration values (see FIG. 33), is the processing of setting a time at which a relative respiration value changes from the inspiration phase PH1 to the expiration phase PH2 as a blood-flow-restricted time TC per respiratory period PC.

The processing (i) is broadly divided into the following two methods.

A first method sets times at which a respiratory vibration value reaches a local maximum value as a blood-flow-restricted time TC in order during an overall time. Specifically, the first method smooths respiratory vibration values in the overall time to reduce high-frequency noise components, thereby extracting a local maximum value (maximum inspiration phase B1) of the respiratory vibration values. This prevents false detection in which noise components of respiratory vibration values are detected as a local maximum value.

A second method sets a time at which a respiratory vibration value reaches a maximum value as a blood-flow-restricted time IC per respiratory period PC. The second method differs from the first method in that not an overall time but a maximum value (namely, maximum inspiration phase B1) of the respiratory vibration values is extracted per respiratory period PC. As in the first method, the second method may smooth respiratory vibration values to reduce high-frequency noise components, thereby extracting a maximum value.

Figure 9:
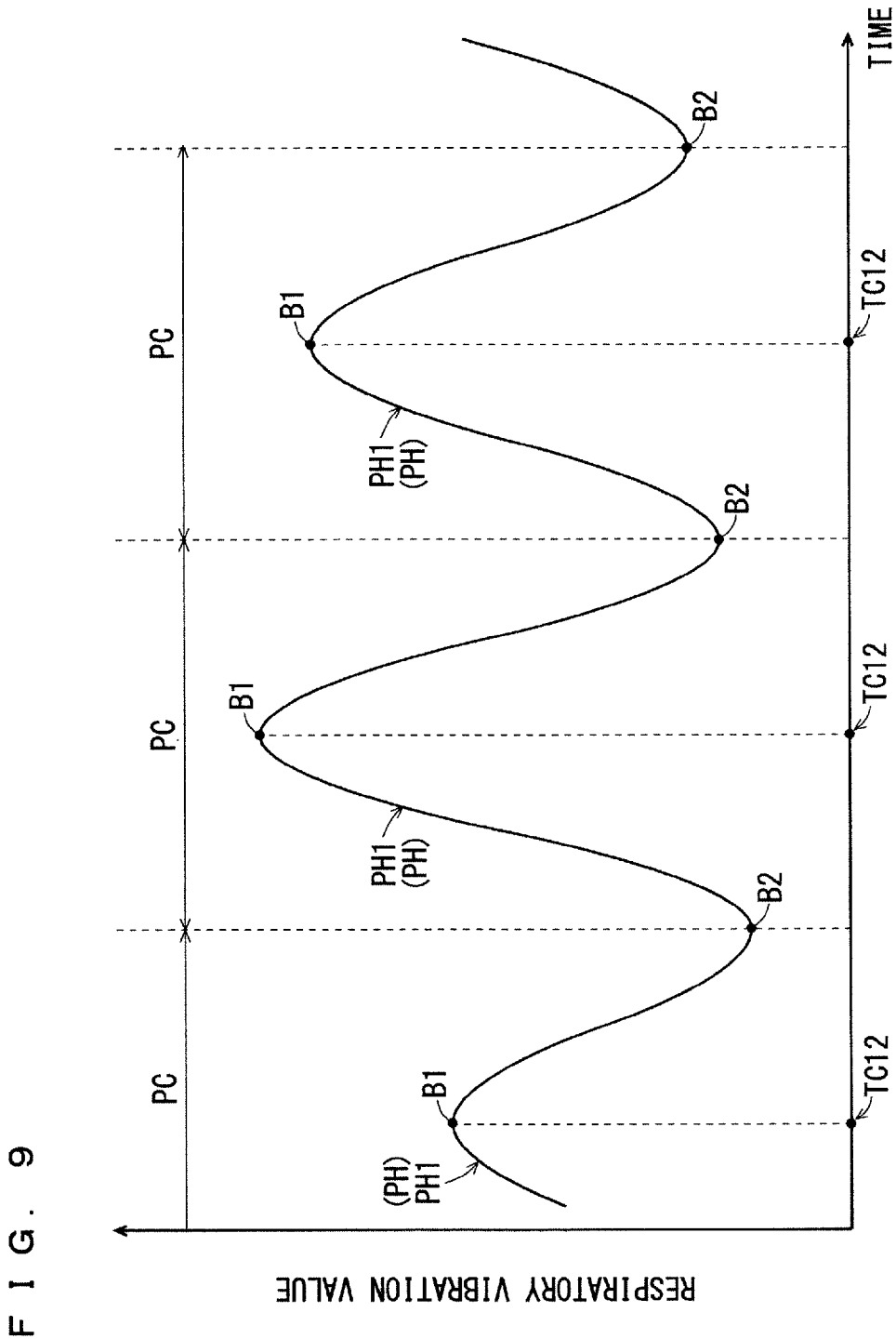
FIG. 9 is another diagram explaining a blood-flow-restricted time determining processing.

FIG. 9 is a diagram explaining the processing (i) of the second blood-flow-restricted time determining processing, where the vertical axis represents a respiratory vibration value and the horizontal axis represents a time at which a moving image is captured. As shown in FIG. 9, in the application of the first method, the blood-flow-restricted time determining unit 130 sets, in order, times at which a local maximum value is reached as a blood-flow-restricted time TC12 (TC) for the respiratory vibration values acquired from all the frame images MI being targets for dynamic diagnosis. In the application of the second method, the blood-flow-restricted time determining unit 130 extracts a maximum value (namely, maximum inspiration phase B1) of the respiratory vibration values per respiratory period PC from among the respiratory vibration values acquired from a plurality of frame images MI being targets for dynamic diagnosis and sets the time at which a maximum inspiration phase B1 is reached as a blood-flow-restricted time TC12 (TC) per respiratory period PC.

Description has been given of the processing (i) with reference to FIG. 9. In the processing (ii), contrastingly, as shown in FIG. 33, the blood-flow-restricted time determining unit 130 sets, in order, times at which a relative respiration value changes from the inspiration phase PH1 to the expiration phase PH2 (namely, a maximum inspiration phase B1 in each respiratory period PC) as a blood-flow-restricted time TC12 (TC) per respiratory period PC.

The processing (ii) detects a maximum inspiration phase B1 on the basis of changes in respiratory phase, allowing a maximum inspiration phase B1 to be detected relatively easily.

<1-3-1-3-3. Third Blood-Flow-Restricted Time Determining Processing: Not Smaller than Reference Value>

A third blood-flow-restricted time determining processing determines, as a blood-flow-restricted time TC, a time included in a time period in which a respiratory vibration value is not less than a predetermined reference value.

Figure 10:
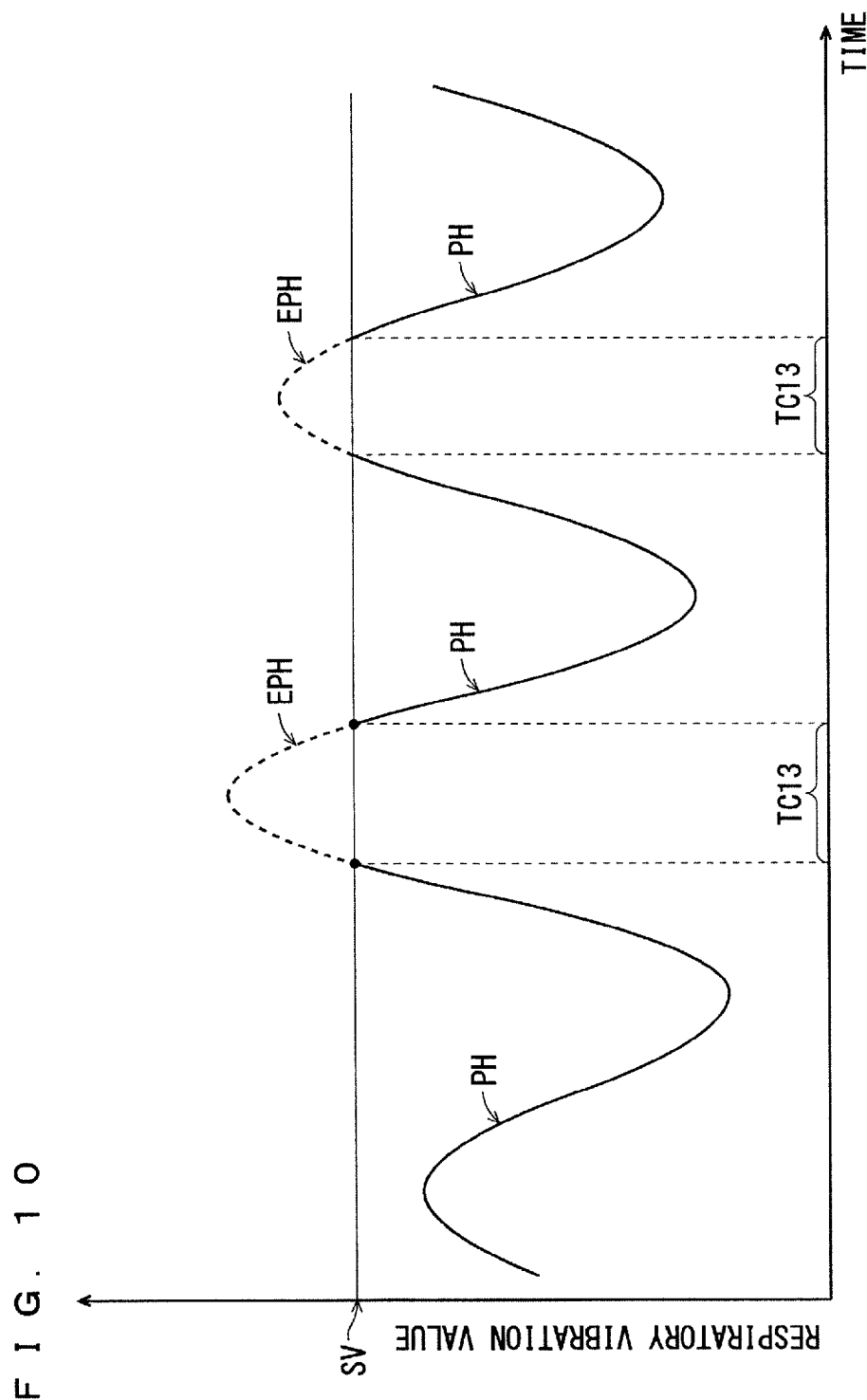
FIG. 10 is still another diagram explaining a blood-flow-restricted time determining processing.

FIG. 10 is a diagram explaining the third blood-flow-restricted time determining processing, where the vertical axis represents a respiratory vibration value, and the horizontal axis represents a time at which a moving image is captured. As shown in FIG. 10, the blood-flow-restricted time determining unit 130 sets, as a blood-flow-restricted time TC13 (TC), a time period in which the respiratory vibration values acquired from a plurality of frame images MI being targets for dynamic diagnosis ire not less than a predetermined reference value SV. More specifically, a time period corresponding to a respiratory phase EPH, which is not less than the reference value SV, of the respiratory phases PH is set as a blood-flow-restricted time TC13. As described above, the third blood-flow-restricted time determining processing sets (a time included in) a certain time period as the blood-flow-restricted time TC13.

<1-3-1-4. Blood-Flow-Analysis Value Calculating Unit 150>

Referring back to FIG. 3, the blood-flow-analysis value calculating unit 150 performs a blood flow analyzing processing of obtaining a blood-flow-analysis value for the analysis data to be subjected to blood flow analysis in the moving image acquired by the moving image acquiring unit 110. The blood-flow-analysis value calculating unit 150 then outputs a blood-flow-analysis value Fv to be used in dynamic diagnosis to the storage unit 32 or the display unit 34.

The blood-flow-analysis value herein basically refers to a value acquired by obtaining a difference between a plurality of frame images MI of a moving image. The processing such as removing noise is also performed if necessary.

<1-3-1-5. Blood Flow Analysis Correcting Unit 151>

The blood flow analysis correcting unit 151 performs a blood-flow-analysis content correcting processing of excluding a frame image MI captured at the blood-flow-restricted time TC set by the blood-flow-restricted time determining unit 130 from targets for blood flow analysis or decreasing the blood-flow-analysis importance of the frame image MI compared with another time period.

The blood-flow-analysis content correcting processing herein refers to any of a preprocessing to be performed before the blood flow analyzing processing is performed and a postprocessing to be performed after the blood flow analyzing processing is performed. Here, in the preprocessing, the data at the blood-flow-restricted time TC of the analysis data is subjected to any of (a1) a processing of prohibiting the blood flow analyzing processing and (a2) a processing of decreasing the importance to allow the blood flow analysis processing. In the postprocessing, meanwhile, the data at the blood-flow-restricted time TC of the blood-flow-analysis value is subjected to any of a (a3) processing of treating the value not as a blood-flow-analysis value and (a4) a processing of decreasing the importance of the blood-flow-analysis value. The preprocessing and the postprocessing will now be described separately.

<1-3-1-5-1. Preprocessing>

In the processing (a1) being a preprocessing, data at the blood-flow-restricted time TC is removed from the analysis data. Then, the blood-flow-analysis value calculating unit 150 performs a blood flow analysis on the data at the times other than the blood-flow-restricted time TC to obtain a blood-flow-analysis value Fv, and then, outputs the blood-flow-analysis value Fv to the storage unit 32 or the display unit 34.

Contrastingly, in the processing (a2) being a preprocessing, the data at the blood-flow-restricted time TC is subjected to the processing of providing blood-flow-analysis value reliability (a weighing coefficient, referred to as "w" below) for decreasing its importance and reducing effects on a blood-flow-analysis value. Weighting herein refers to weighting the reliability of a blood-flow-analysis value f on the basis of a blood-flow-analysis value (hereinafter, referred to as "f") calculated in a normal blood flow analyzing processing in the case where for example, a position or time at which a blood clot is suspected is extracted (case 1), the case where data is rearranged in the order of patients who are more highly suspected to have a blood clot (case 2), or other case.

Specifically, in the case 1, assuming that a level of suspected blood clot is calculated from a difference (hereinafter referred to as "B") in the blood-flow-analysis value f between upstream and downstream in the direction of the blood flow of an affected part, multiplication (w*B) is performed to decrease a level of suspected blood clot for lower blood-flow-analysis value reliability w. In the case 2, the method of multiplying the level of suspected blood clot by the blood-flow-analysis value reliability w is adoptable.

In another case, the blood-flow-analysis-value reliability w can be used to calculate an accurate blood-flow-analysis value Fv per blood flow cycle. In other words, an accurate blood-flow-analysis value Fv per blood flow cycle can be obtained not by merely averaging the blood-flow-analysis values f of the blood flow cycles but by weighted average using the blood-flow-analysis value reliability w. Here, it is preferable that "w=1" at times other than the blood-flow-restricted time TC and that "w<1" to decrease the importance as the blood-flow-analysis value f at the blood-flow-restricted time IC. In other words, as in the processing (a1), data at the blood-flow-restricted time TC is not used for dynamic diagnosis. Thus, a clear distinction can be made between a blood-flow-analysis value Fv after correction, which is "w*f=0", and a blood-flow-analysis value Fv in another time period. Subsequently, the blood-flow-analysis value calculating unit 150 obtains a blood-flow-analysis value Fv after correction, and then, outputs the blood-flow-analysis value Fv to the storage unit 32 or the display unit 34.

<1-3-1-5-2. Postprocessing>

In the processing (a3) being a postprocessing, the data at the blood-flow-restricted time TC among the pieces of data (blood-flow-analysis values) after analysis calculated by the blood-flow-analysis value calculating unit 150 is not treated as a blood-flow-analysis value, and the blood-flow-analysis values at times other than the blood-flow-restricted time TC are treated as a blood-flow-analysis value Fv. Then, the blood flow analysis correcting unit 151 outputs the blood-flow-analysis value Fv to the storage unit 32 or the display unit 34.

In the processing (a4) being a postprocessing, the data at the blood-flow-restricted time TC among the pieces of data (blood-flow-analysis values) after analysis calculated by the blood-flow-analysis value calculating unit 150 is made such that, for example, "w=0" as in the processing (a2), and the blood-flow-analysis value Fv after correction is set such that "w*f=0," thereby clearly distinguishing the blood-flow-analysis value Fv from the blood-flow-analysis value Fv in another time period. Subsequently, the blood-flow-analysis value calculating unit 150 obtains a blood-flow-analysis value Fv after correction, and then, outputs the blood-flow-analysis value Fv to the storage unit 32 or the display unit 34.

<1-4. Basic Operation of Image Processing Apparatus 3>

Figure 11:
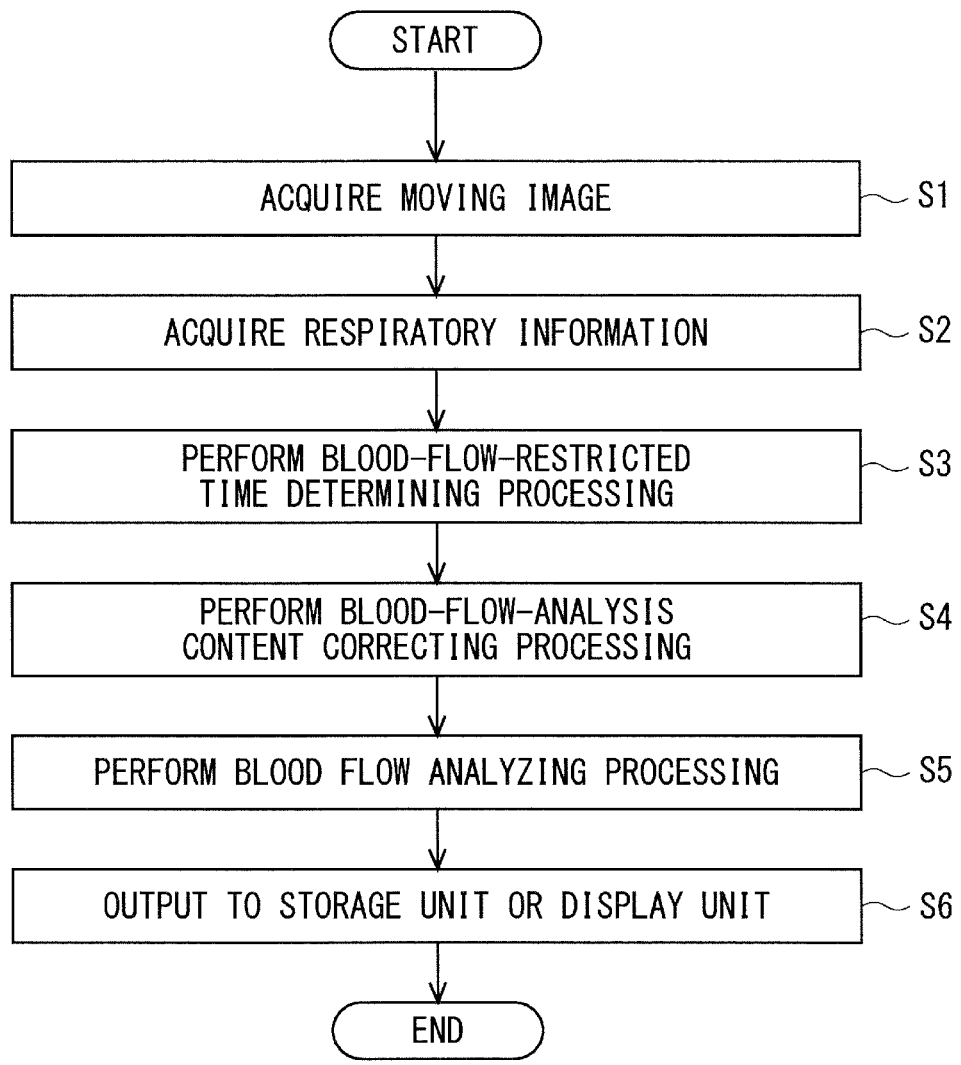
FIG. 11 is a flowchart explaining the basic operation of the image processing apparatus 3 achieved in the first embodiment.
Figure 12:
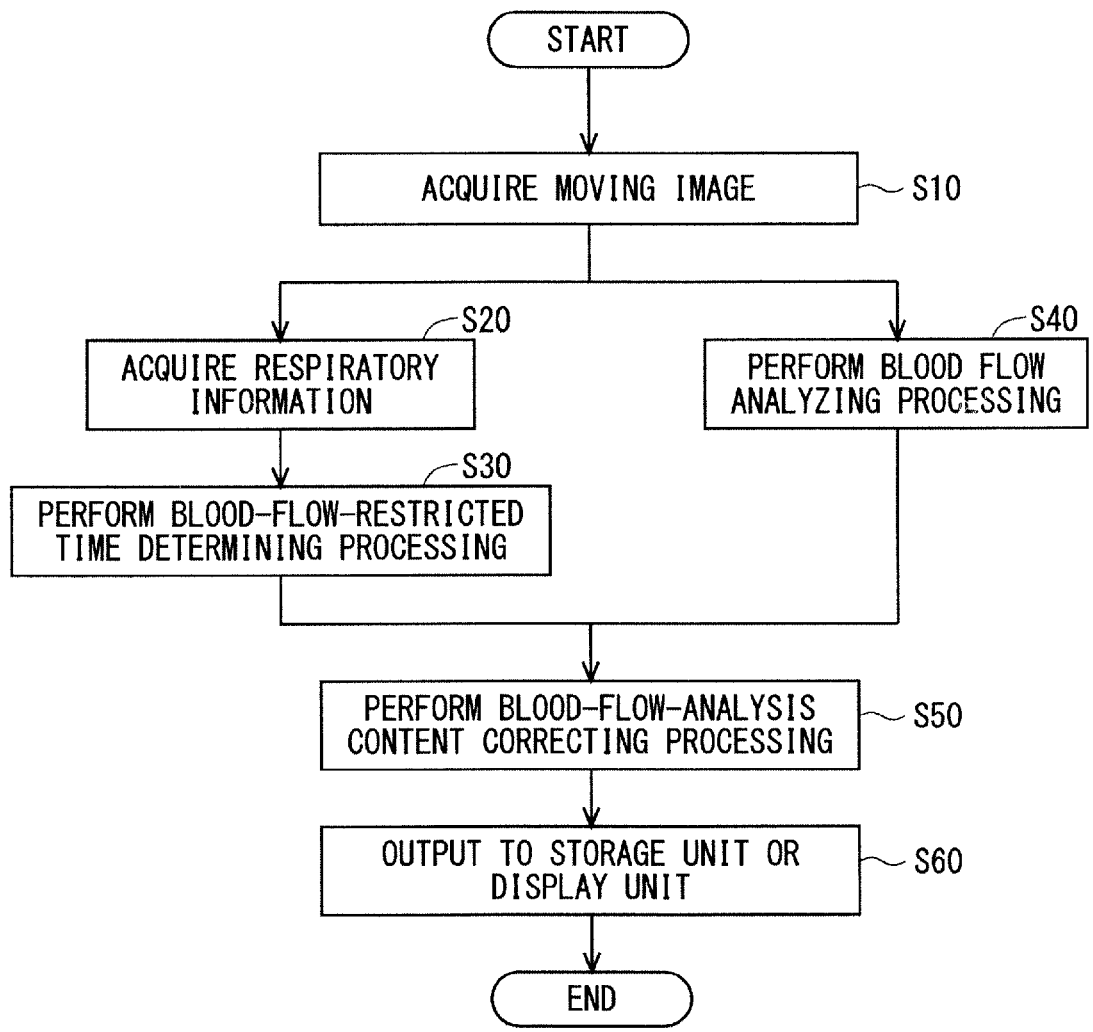
FIG. 12 is another flowchart explaining the basic operation of the image processing apparatus 3 achieved in the first embodiment.

FIG. 11 and FIG. 12 are flowcharts explaining the basic operation achieved by the image processing apparatus 3 according to this embodiment. FIG. 11 is the flowchart in the case where the blood-flow-analysis content correcting processing is the preprocessing (a1) or (a2). FIG. 12 is the flowchart in the case where the blood-flow-analysis content correcting processing is the postprocessing (a3) or (a4). The functions of the individual units have been described (see FIG. 3), and thus, only the overall flow will now be described.

<1-4-1. Flow of Preprocessing>

First, description will be given of the case where the blood-flow-analysis content correcting processing is the preprocessing with reference to FIG. 11.

As shown in FIG. 11, first, in Step S1, the moving image acquiring unit 110 of the control unit 31 acquires a moving image (a plurality of frame images MI) captured by the reading control device 14 of the photographing apparatus 1 through the photographing control apparatus 2.

In Step S2, the respiratory information acquiring unit 120 performs the first or second respiratory information acquiring processing of acquiring respiratory information such as respiratory vibration values and relative respiration values and detects a respiratory phase PH or a respiratory period PC (see FIG. 5 to FIG. 7).

In Step S3, the blood-flow-restricted time determining unit 130 performs any one of the first to third blood-flow-restricted time determining processings and sets a blood-flow-restricted time TC (any of TC11, TC12, and TC13) (see FIG. 8 to FIG. 10).

In Step S4, the blood flow analysis correcting unit 151 performs, at the blood-flow-restricted time TC set in Step S3, a blood-flow-analysis content correcting processing of eliminating a frame image MI from targets for blood flow analysis or decreasing the blood-flow-analysis importance of the frame image MI compared with another time period. In other words, the blood-flow-analysis content correcting processing herein refers to a preprocessing to be performed before the blood flow analysis, and the blood flow analysis correcting unit 151 performs any of the processings (a1) and (a2).

In Step S5, the blood-flow-analysis value calculating unit 150 performs a blood flow analyzing processing on analysis data (a plurality of frame images MI) in consideration of the result of the processing (a1) or (a2) performed in Step S4, thereby obtaining a blood-flow-analysis value Fv.

Finally, in Step S6, the blood-flow-analysis value calculating unit 150 outputs the blood-flow-analysis value Fv after the correction acquired in Step S5 to the storage unit 32 or the display unit 34 (see FIG. 3), and the operational flow is ended.

<1-4-2. Flow of Postprocessing>

Subsequently, the case where the blood-flow-analysis content correcting processing is the postprocessing will be described with reference to FIG. 12. The descriptions of Steps S10 to S30 similar to the preprocessing (Steps S1 to S3) shown in FIG. 11 will be omitted, and only Steps S40 to S60 different from the preprocessing will be described.

In Step S40, the blood-flow-analysis value calculating unit 150 performs a blood flow analyzing processing on the plurality of frame images MI acquired in Step S10, thereby obtaining a blood-flow-analysis value.

Step S40 may be performed in parallel with Step S20 and Step S30, or may be performed before or after Step S20 and Step S30. In other words, it suffices that Step S40 is performed before Step S50.

In Step S50, the blood flow analysis correcting unit 151 performs, at the blood-flow-restricted time TC set in Step S30, any one of the blood-flow-analysis content correcting processing (a3) and (a4) of eliminating a relevant blood-flow-analysis value obtained in Step S40 from the targets for blood flow analysis or decreasing the blood-flow-analysis importance of the relevant blood-flow-analysis value compared with another time period.

In Step S60, the blood flow analysis correcting unit 151 outputs the blood-flow-analysis value Fv after the correction acquired in Step S50 to the storage unit 32 or the display unit 34.

As described above, the image processing apparatus 3 determines a blood-flow-restricted time TC on the basis of the respiratory information by the blood-flow-restricted time determining unit 130 and performs, by the blood flow analysis correcting unit 151, the blood-flow-analysis content correcting processing of eliminating a frame image captured at the blood-flow-restricted time TC from the targets for blood flow analysis or decreasing the blood-flow-analysis importance of the frame image compared with another time period. The blood flow analysis accompanying the blood-flow-analysis content correcting processing is accordingly enabled, preventing the blood-flow-analysis value from becoming an abnormal value associated with respiration, which results in a highly accurate, appropriate blood-flow-analysis value Fv. This prevents a decrease in the performance of finding a blood clot, enabling dynamic diagnosis of a blood flow to be performed appropriately and efficiently.

The first blood-flow-restricted time determining processing is a processing of determining, as a blood-flow-restricted time TC11, a time at which the respiratory vibration value becomes a maximum value MX. Thus, the time when it is assumed that a blood flow is restricted most and that a blood-flow-analysis value is most adversely affected can be determined as a blood-flow-restricted time TC11.

The second blood-flow-restricted time determining processing is a processing of determining a time at which the respiratory vibration value becomes a maximum value (a maximum inspiration phase B1 in every respiratory period PC) as a blood-flow-restricted time TC12 per respiratory period. The maximum value can be obtained per respiratory period PC, enabling the determination of a time, when it is assumed that a blood-flow-analysis value is adversely affected, as the blood-flow-restricted time TC12 on the basis of a value of physical change in the lung field region.

The second blood-flow-restricted time determining processing also includes a processing of determining a time at which the relative respiration value changes from the inspiration phase to the expiration phase (a time at which the relative respiration value becomes a maximum inspiration phase B1 in every respiratory period PC in FIG. 33) as a blood-flow-restricted time TC12 per respiratory period PC. This enables the determination of the time, when it is assumed that a blood flow is restricted most and that a blood flow analysis is adversely affected, as a blood-flow-restricted time TC12 per respiratory period PC, achieving the robustness effect where there is no influence of another period. The respiratory period PC is recognized from the relative respiration value, eliminating the need for acquiring a respiratory period PC on the basis of a moving image, which simplifies the processing of acquiring respiratory information.

The third blood-flow-restricted time determining processing is a process of determining, as a blood-flow-restricted time TC13, a time included in a time period) at which the respiratory vibration value is not less than a predetermined reference value SV. Thus, the blood-flow-restricted time TC13 can be extended and set easily without obtaining a maximum inspiration phase B1 from a maximum value MX of every respiratory period PC.

Setting of a reference value SV using the statistical data obtained as knowledge enables a blood-flow-restricted time TC13 to be determined stably, independently of the data obtained from a moving image.

Further, providing a reference value SV enables accurate comparison of differences in blood-flow-analysis value Fv for pieces of moving image data on the same body (subject M) before and after the photographing period. Thus, the state of a blood flow in one body can be accurately monitored over time from dynamic diagnosis.

The blood-flow-analysis content correcting processing includes any one of the processings (a1) to (a4). In other words, the processing of prohibiting the blood flow analyzing processing is performed in the processing (a1), or the processing of alleviating the effects of the blood flow analyzing processing before this processing is performed in the processing (a2), enabling efficient blood flow analysis in consideration of a blood-flow-restricted time TC. In particular, the processing (a1) does not require the blood flow analyzing processing at a blood-flow-restricted time TC, reducing a calculation time without unnecessary calculations.

Meanwhile, for the data at the blood-flow-restricted time TC after the blood flow analysis is performed, the processing of treating the data not as a blood-flow-analysis value is performed in the processing (a3), or the processing of decreasing the importance of the data is performed in the processing (a4). This eliminates the need for setting a blood-flow-restricted time TC before the blood flow analyzing processing, allowing the blood-flow-restricted time TC to be set after the blood flow analyzing processing is performed.

Further, the target region is the blood vessel region in the lung field region, and thus, the state of a blood flow in the lung field region can be appropriately understood by dynamic diagnosis. This can prevent a decrease in the performance of finding pulmonary thromboembolism.

2. Second Embodiment

Figure 13:
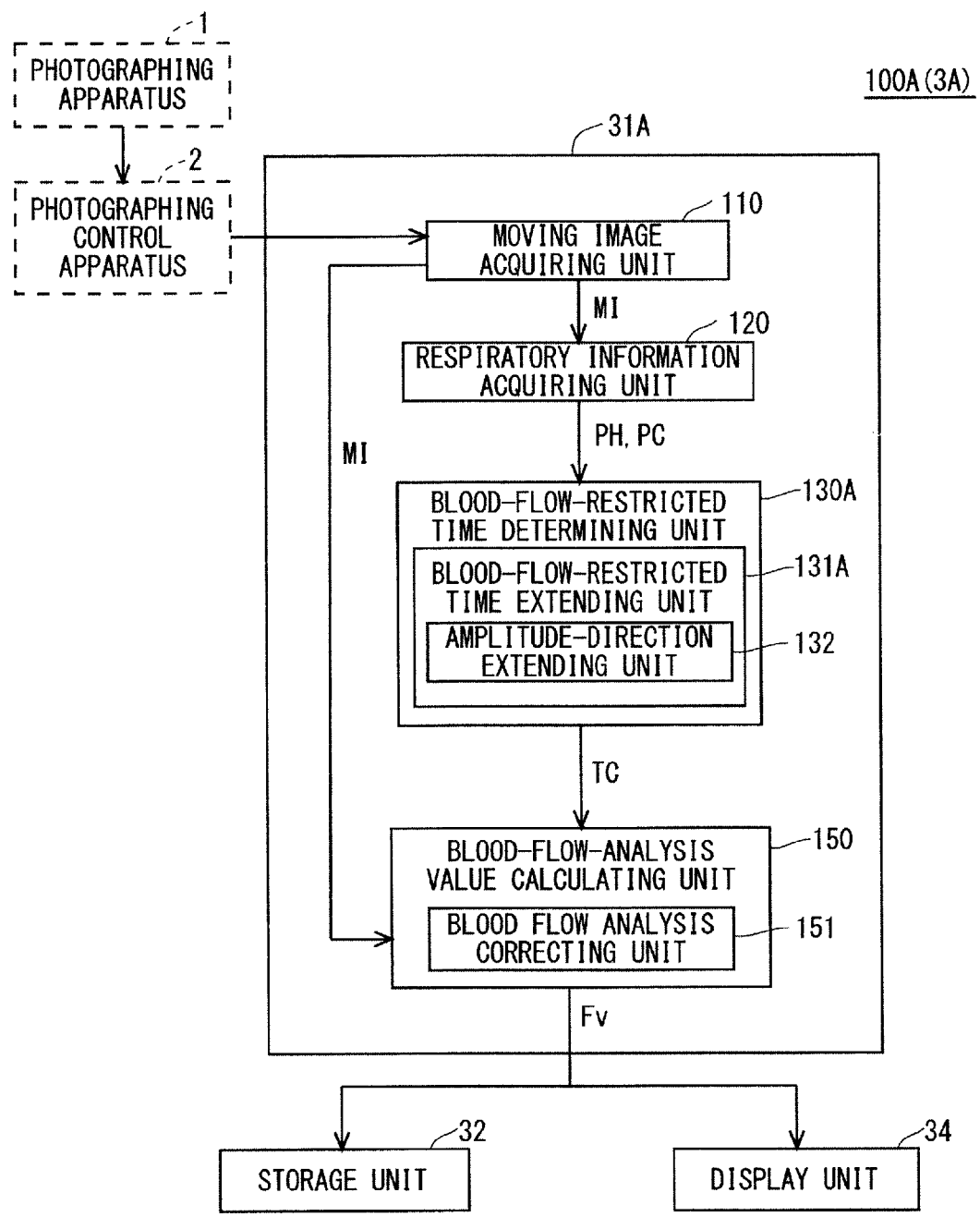
FIG. 13 is a block diagram showing the functional configuration of an image processing apparatus 3A according to a second embodiment.

FIG. 13 is a diagram showing the functional configuration of a control unit 31A to be used in an image processing apparatus 3A configured as a second embodiment of the present invention. The control unit 31A is used in place of the control unit 31 in the image processing apparatus 3 of the first embodiment (see FIG. 3). The second embodiment differs from the first embodiment in that a blood-flow-restricted time determining unit 130A corresponding to the blood-flow-restricted time determining unit 130 of the first embodiment includes a blood-flow-restricted time extending unit 131A and that the blood-flow-restricted time extending unit 131A includes an amplitude-direction extending unit 132. The other units are similar to those of the image processing apparatus 3.

<2-1. Blood-Flow-Restricted Time Extending Unit 131A, Amplitude-Direction extending Unit 137>

The blood-flow-restricted time determining unit 130A includes the blood-flow-restricted time extending unit 131A that extends a blood-flow-restricted time TC to provide a time width ΔT relative to the blood-flow-restricted time TC. The blood-flow-restricted time extending unit 131A includes the amplitude-direction extending unit 132 that performs an amplitude-direction extending processing to set the time width ΔT.

The amplitude-direction extending processing is broadly divided into four types of processings and any one of the processings is performed. First to fourth amplitude-direction extending processings will now be described separately.

<2-1-1. First Amplitude-Direction Extending Processing>

The first amplitude-direction extending processing is a processing of setting a time width at a time at which a respiratory vibration value is not less than a first threshold, which is a value smaller than a maximum respiratory vibration value by a first value.

Figure 14:
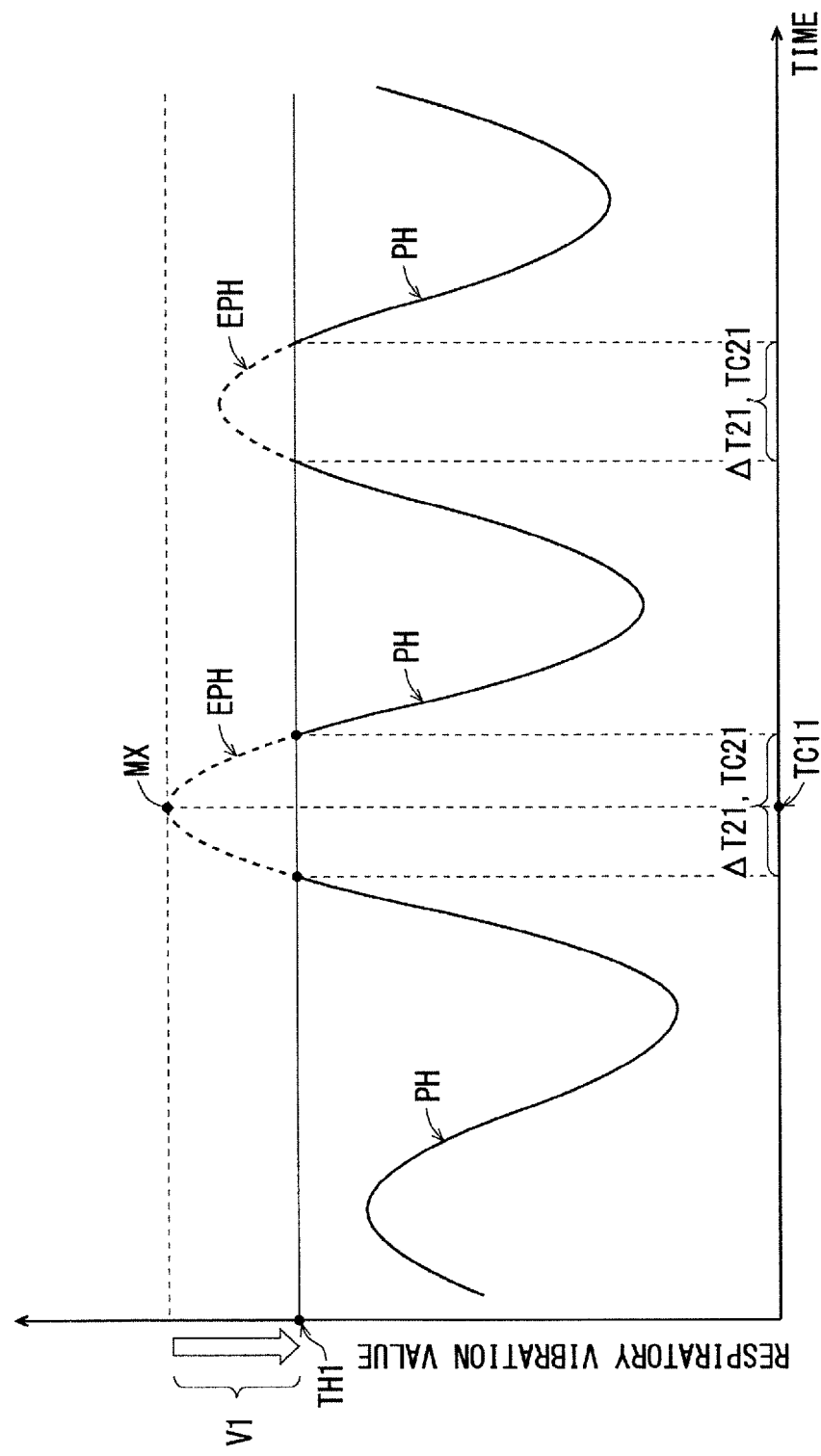
FIG. 14 is a diagram explaining an amplitude-direction extending processing.

FIG. 14 is a diagram explaining the first amplitude-direction extending processing, where the vertical axis represents a respiratory vibration value, and the horizontal axis represents a time at which a moving image is captured. As shown in FIG. 14, the blood-flow-restricted time extending unit 131A extends a blood-flow-restricted time TC11 to provide a time width ΔT21 relative to a blood-flow-restricted time TC11 set in the first blood-flow-restricted time determining processing. Specifically, with a value smaller than the maximum value MX of the respiratory vibration values by a first value V1 being a first threshold TH1, the time width ΔT21 is set at a time in a respiratory phase EPH in which the respiratory vibration value is not less than the first threshold TH1. The collection of times in the time width ΔT21 is referred to as a blood-flow-restricted time TC21.

<2-1-1-1. First Value Determining Processing>

The first value determining processing is a processing of setting a first threshold TH1 by regarding the first value V1 used in the first amplitude-direction extending processing as any one of (b1) a value calculated based on a difference between a value MX, which is a maximum respiratory vibration value, and a minimum value MN, which is a minimum respiration vibration value, and (b2) a constant value determined in advance.

Figure 16:
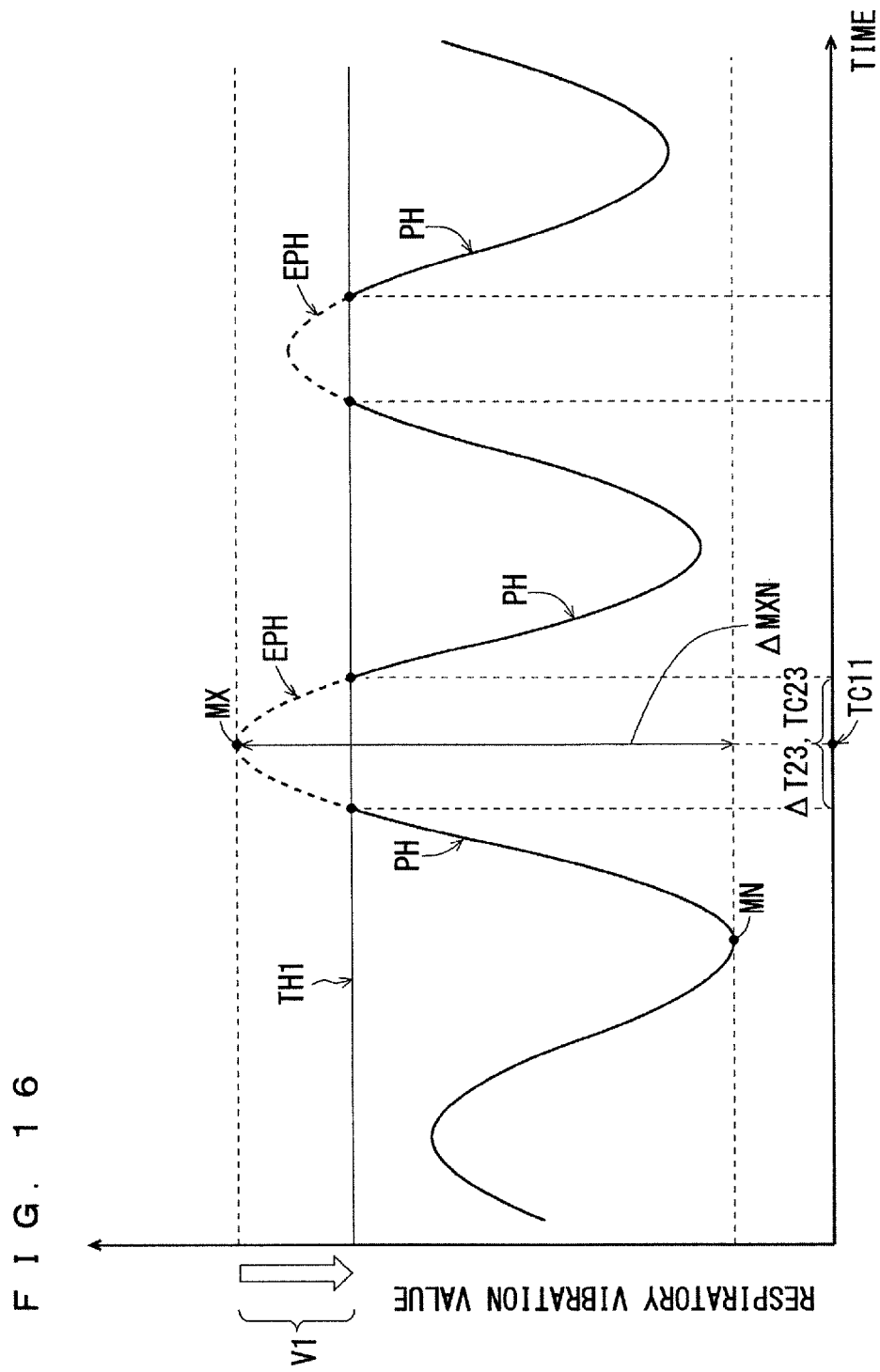
FIG. 16 is still another diagram explaining the amplitude-direction extending processing.

FIG. 16 is a diagram explaining the first value determining processing, where the vertical axis represents a respiratory vibration value, and the horizontal axis represents a time at which a moving image is captured. As shown in FIG. 16, the blood-flow-restricted time extending unit 131A extends a blood-flow-restricted time TC11 to provide a time width ΔT23 relative to a blood-flow-restricted time TC11 set in the first blood-flow-restricted time determining processing.

FIG. 16 describes the method (b1) in the first value determining processing. In other words, described here is a method of determining a first value V1 as an appropriate ratio to a difference value ΔMXN between a maximum value MX and a minimum value MN of the respiratory vibration values. For example, in the case where the first value V1 is set as a value of 20% to the difference value ΔMXN in terms of percentage and in the case where the first value V1 is set as a value of 40% to the difference value ΔMXN in terms of percentage, the first threshold TH1 becomes lower for the case of 40% than for the case of 20%, and accordingly, a time width ΔT23 is set to be larger for 40% than for 20%.

As described above, in the use of the method (b1), a time width ΔT23 varies in accordance with an appropriate ratio, resulting in the blood-flow-restricted time TC23 varying correspondingly.

In the use of the method (b2), meanwhile, the first value V1 is a fixed value determined in advance, resulting in the blood-flow-restricted time TC23 varying in accordance with a constant value specified by the user.

The first value V1 is determined by the method (b1) or (b2), which is not limited thereto, and may be determined by another method. For example, the first value V1 may be determined in consideration of the profile of a patient such as the size or the health condition of a patient, such as whether a patient suffers from chronic obstructive pulmonary disease (COPD).

<2-1-2. Second Amplitude-Direction Extending Processing>

The second amplitude-direction extending processing is a processing of setting a time width at a time at which a respiratory vibration value is not less than a second threshold, which is a value smaller than a value B1 being a maximum respiratory vibration value by a second value, per respiratory period PC.

Figure 15:
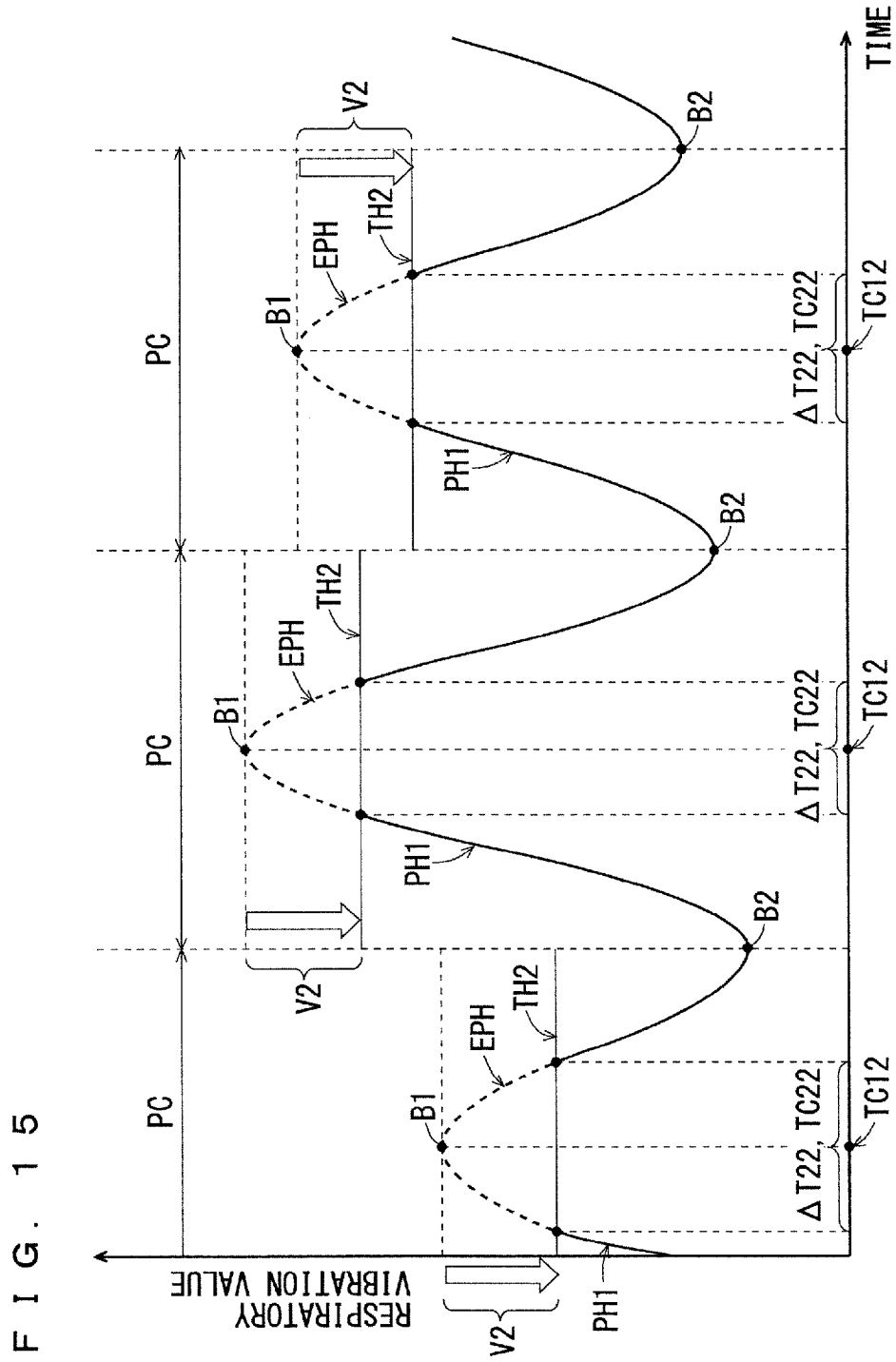
FIG. 15 is another diagram explaining the amplitude-direction extending processing.

FIG. 15 is a diagram explaining the second amplitude-direction extending processing, where the vertical axis represents a respiratory vibration value, and the horizontal axis represents a time at which a moving image is captured. As shown in FIG. 15, the blood-flow-restricted time extending unit 131A extends a blood-flow-restricted time TC12 to provide a time width ΔT22 relative to a blood-flow-restricted time TC12 set in the second blood-flow-restricted time determining processing. Specifically, a value smaller than the maximum respiratory vibration value (that is, maximum inspiration phase B1) by a second value V2 is regarded as a second threshold TH2 per respiratory period PC, and a tune width ΔT22 is set at a time in the respiratory phase EPH in which the respiratory vibration value is not less than the second threshold TH2. The collection of times in the time width ΔT22 is referred to as a blood-flow-restricted time TC22.

<2-1-2-1. Second Value Determining Processing>

The second value determining processing is a processing of setting a second threshold TH2 by regarding the second value as any one of a (c1) value set for each respiratory period PC and calculated on the basis of a difference value between a value B1, which is a maximum respiratory vibration value, and a value B2, which is a minimum respiratory vibration value, and a (c2) constant value determined in advance.

Figure 17:
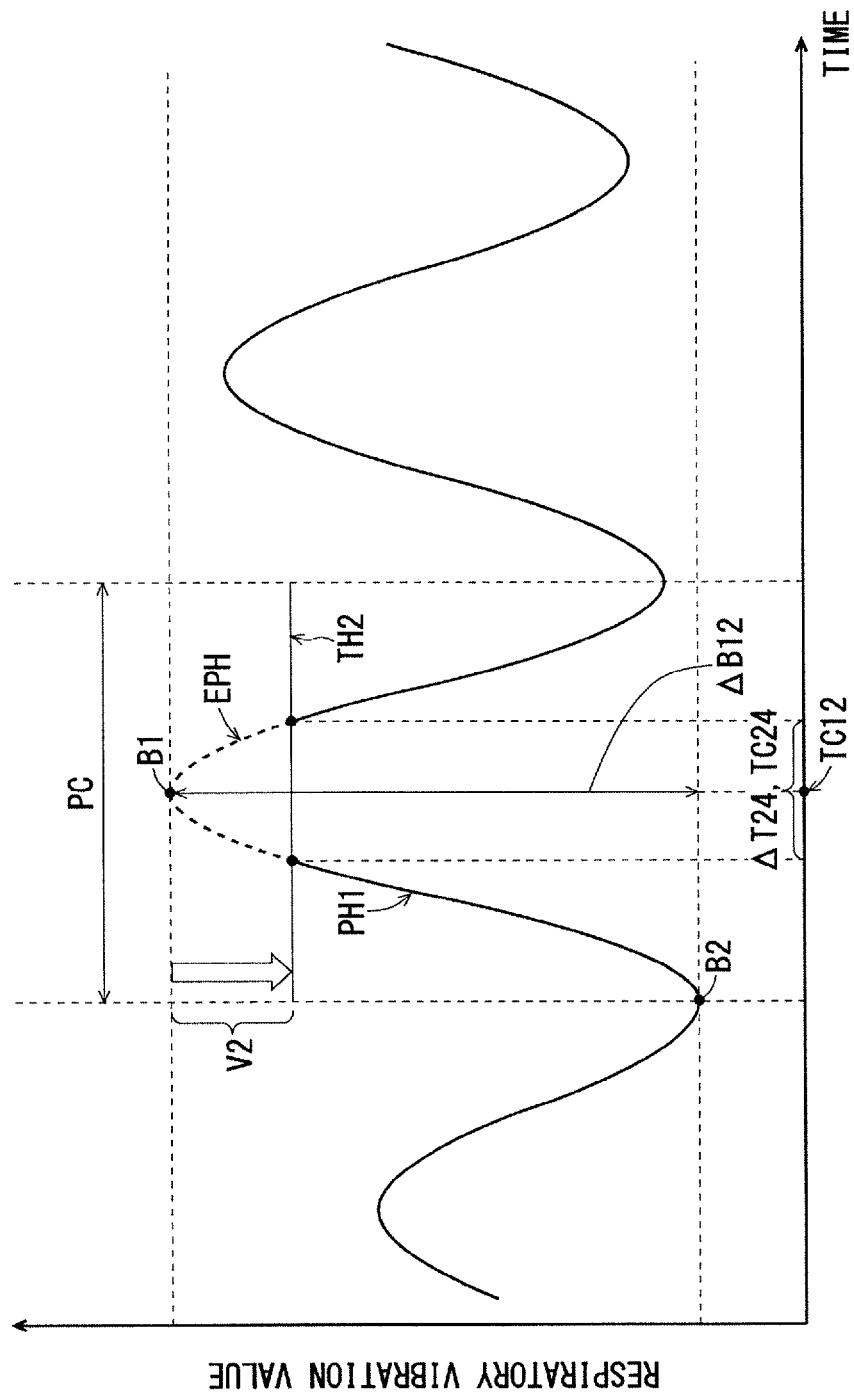
FIG. 17 is still another diagram explaining the amplitude-direction extending processing.

FIG. 17 is a diagram explaining the second value determining processing, where the vertical axis represents a respiratory vibration value, and the horizontal axis represents a time at which a moving image is captured. As shown in FIG. 17, the blood-flow-restricted time extending unit 131A extends a blood-flow-restricted time TC12 to provide a time width ΔT24 relative to a blood-flow-restricted time TC12 set in the second blood-flow-restricted time determining processing.

FIG. 17 explains the method (c1) in the second value determining processing by only showing one respiratory period PC. In other words, described here is a method of determining a second value V2, which is set per respiratory period PC, as an appropriate ratio to a difference value ΔB12 between a maximum value (that is, maximum inspiration phase B1) and a minimum value (that is, maximum expiration phase B2) of the respiratory vibration values. For example, in the case where the second value V2 is set as a value of 20% to the difference value ΔB12 in terms of percentage and in the case where the second value V2 is set as a value of 40% to the difference value ΔB12 in terms of percentage, similarly to the above, the second threshold TH2 becomes lower for the case of 40% than for the case of 20%, and accordingly, a time width ΔT24 is set to be larger for 40% than for 20%.

As described above, in the use of the method (c1), a time width ΔT24 varies in accordance with an appropriate ratio, resulting in the blood-flow-restricted time TC24 varying correspondingly.

In the use of the method (c2), meanwhile, the second value V2 is a fixed value determined in advance, resulting in the blood-flow-restricted time TC24 varying in accordance with a constant value specified by the user.

The second value V2 is determined by the method (c1) or (c2), which is not limited thereto, and may be determined by another method. For example, the second value V2 may be determined by the user specifying a desired numerical value per respiratory period PC, or the second value V2 may be determined in consideration of the above-mentioned profile of a patient.

<2-2. Basic Operation of Image Processing Apparatus 3A>

FIG. 18 is a diagram illustrating the operational flow of the image processing apparatus 3A according to the second embodiment. FIG. 18 shows a representative case where the blood-flow-analysis content correcting processing is the preprocessing (a1) or (a2). Steps SA1, SA2, and SA4 to SA6 of FIG. 18 are similar to Steps S1, S2, and S4 to S6 of FIG. 11, which will not be described here.

The blood-flow-restricted time extending unit 131A (amplitude-direction extending unit 132), which is not provided in the first embodiment, is added in the second embodiment, and thus, only the following steps are changed.

In other words, through Steps SA1 and SA2 as steps similar to the steps of the first embodiment, as shown in FIG. 18, the blood-flow-restricted time determining unit 130A performs the first or second blood-flow-restricted time determining processing in Step SA3, and then, the amplitude-direction extending unit 132 sets a time width ΔT in any one of the first and second amplitude-direction extending processings, thereby determining a blood-flow-restricted time TC (see FIG. 14 to FIG. 17).

Specifically, in the case where the blood-flow-restricted time determining unit 130A performs the first blood-flow-restricted time determining processing, the amplitude-direction extending unit 132 sets a time width ΔT21 or ΔT23 and sets a blood-flow-restricted time TC21 or TC23 in the first amplitude-direction extending processing (see FIG. 14 and FIG. 16). In the case where the blood-flow-restricted time determining unit 130A performs the second blood-flow-restricted time determining processing, the amplitude-direction extending unit 132 sets a time width ΔT22 or ΔT24 and sets a blood-flow-restricted time TC22 or TC24 in the second amplitude-direction extending processing (see FIG. 15 and FIG. 17).

The remaining steps are performed as in the first embodiment.

As described above, in the image processing apparatus 3A according to the second embodiment, the blood-flow-restricted time determining unit 130A includes the blood-flow-restricted time extending unit 131A that extends a blood-flow-restricted time TC11 or TC12 to provide a time width ΔT relative to the blood-flow-restricted time TC11 or TC12. The time period, when it is assumed that a blood flow is restricted and that a blood flow analysis is adversely affected, can accordingly be extended (see FIG. 14 to FIG. 17).

The first amplitude-direction extending processing generates a time width ΔT21 at a time at which the respiratory vibration value is not less than the first threshold TH1 to extend and reliably extract a time period during which a blood flow is highly likely to be restricted, thereby setting the time period as a blood-flow-restricted time TC21 (see FIG. 14).

The second amplitude-direction extending processing sets a time width ΔT22 using a maximum respiratory vibration value (maximum inspiration phase B1) per respiratory period PC to appropriately extract a time at which a blood flow is highly likely to be restricted during the respiratory period PC, thereby setting the time as a blood-flow-restricted time TC22. The amplitude-direction extending processing is performed per respiratory period PC, achieving the robustness effect where there is no influence of another period (see FIG. 15).

In the case where a value based on the difference value ΔMXN between the maximum value MX and the minimum value MN of the respiratory vibration values is used as the first value V1 in the first amplitude-direction extending processing, a first value V1 can be determined by a maximum respiratory amplitude value in the respiratory phase PH. This enables the first threshold TH1 to be appropriately set without being too low (see FIG. 16). In the case where a predetermined constant value is used as the first value V1, the first threshold TH1 can be set easily without specifically calculating a maximum respiratory amplitude value in the respiratory phase PH.

Further, in the case where a value based on the difference value ΔB12 between a maximum respiratory vibration value (maximum inspiration phase B1) and a minimum respiratory vibration value (maximum expiration phase B2) per respiratory period PC is used as the second value V2 in the second amplitude-direction extending processing, the second value V2 can be determined by a respiratory amplitude value, enabling the second threshold TH2 to be appropriately set without being too low (see FIG. 17). In the case where a predetermined constant value is used as the second value V2, the second threshold TH2 can be set easily without specifically calculating a respiratory amplitude value.

3. Third Embodiment

Figure 19:
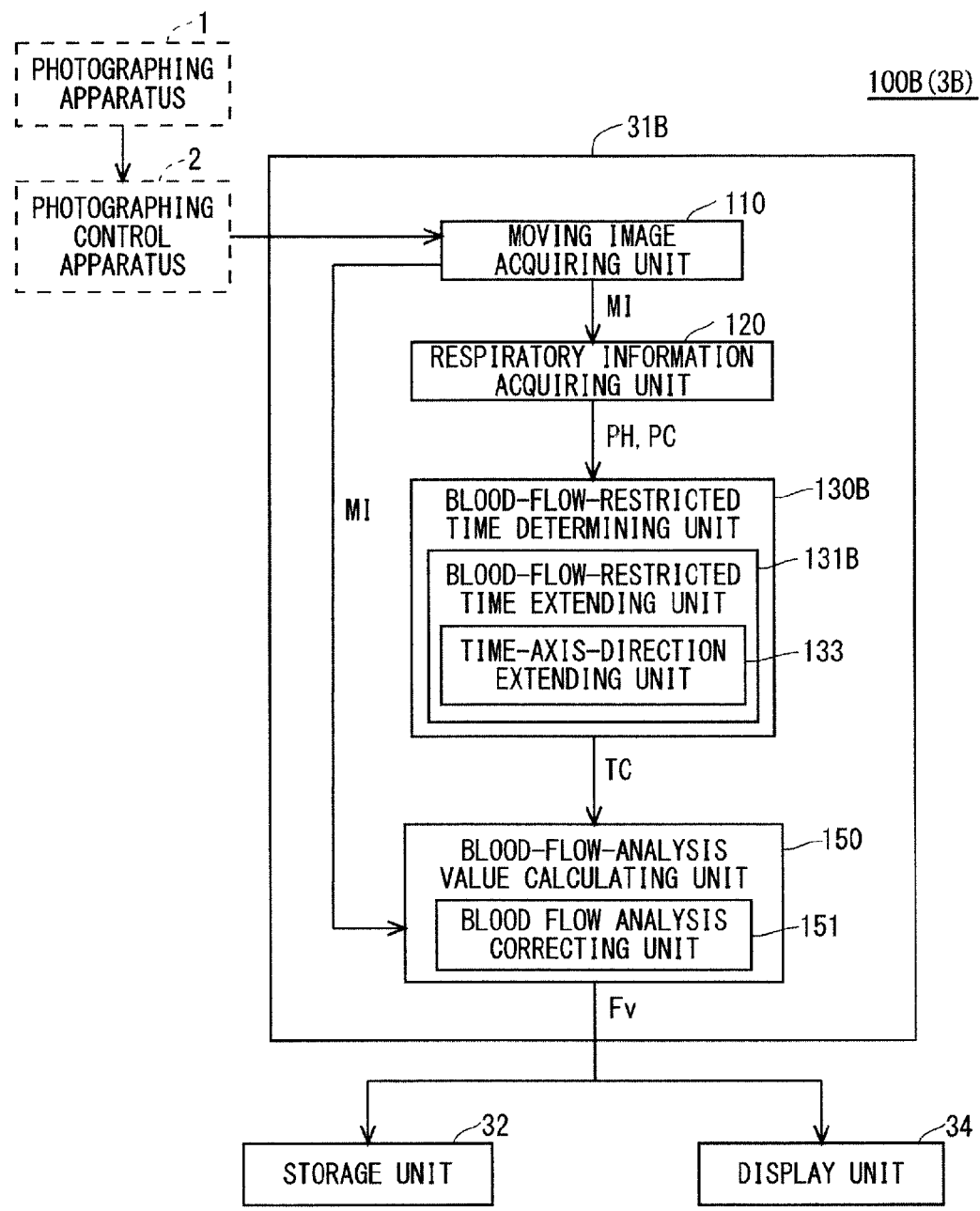
FIG. 19 is a block diagram showing the functional configuration of an image processing apparatus 3B according to a third embodiment.

FIG. 19 is a diagram showing the functional configuration of a control unit 318 to be used in an image processing apparatus 3B configured as a third embodiment of the present invention. The control unit 318 is used in place of the control unit 31 in the image processing apparatus 3 of the first embodiment (see FIG. 3). The third embodiment differs from the first embodiment in that a blood-flow-restricted time determining unit 130B corresponding to the blood-flow-restricted time determining unit 130 of the first embodiment includes a blood-flow-restricted time extending unit 131B and the blood-flow-restricted time extending unit 131B includes a time-axis-direction extending unit 133. The remaining components are similar to those of the image processing apparatus 3.

<3-1. Blood-Flow-Restricted Time Extending Unit 131B, Time-Axis-Direction Extending Unit 133>

The blood-flow-restricted time determining unit 130B includes the blood-flow-restricted time extending unit 131B that extends a blood-flow-restricted time TC to provide a time width $\Delta T$ relative to a blood-flow-restricted time TC. The blood-flow-restricted time extending unit 131B includes the time-axis-direction extending unit 133 that performs a time-axis-direction extending processing to set the time width $\Delta T$.

The time-axis-direction extending processing is broadly divided into three types of processings, and any one of the processings is performed. The first to third time-axis-direction extending processings will now be described separately.

<3-1-1. First Time-Axis-Direction Extending Processing>

The first time-axis-direction extending processing is a processing of setting a time width $\Delta T$ as a combined time width of the first time width determined on the basis of the time required for the inspiration phase PH1 and the second time width determined on the basis of the time required for the expiration phase PH2 per respiratory period PC. The "combined time width" herein refers to a time width which combines the first time width and the second time width set independently while they are kept as known information. In other words, the blood-flow-restricted time extending unit 131B extends the blood-flow-restricted time TC12 to provide a time width (a combined time width of a first time width and a second time width) $\Delta T3$ relative to the blood-flow-restricted time TC12 determined in the second blood-flow-restricted time determining processing, and the blood-flow-restricted time determining unit 130B determines a blood-flow-restricted time TC31 (see FIG. 20 and FIG. 21 below).

Figure 20:
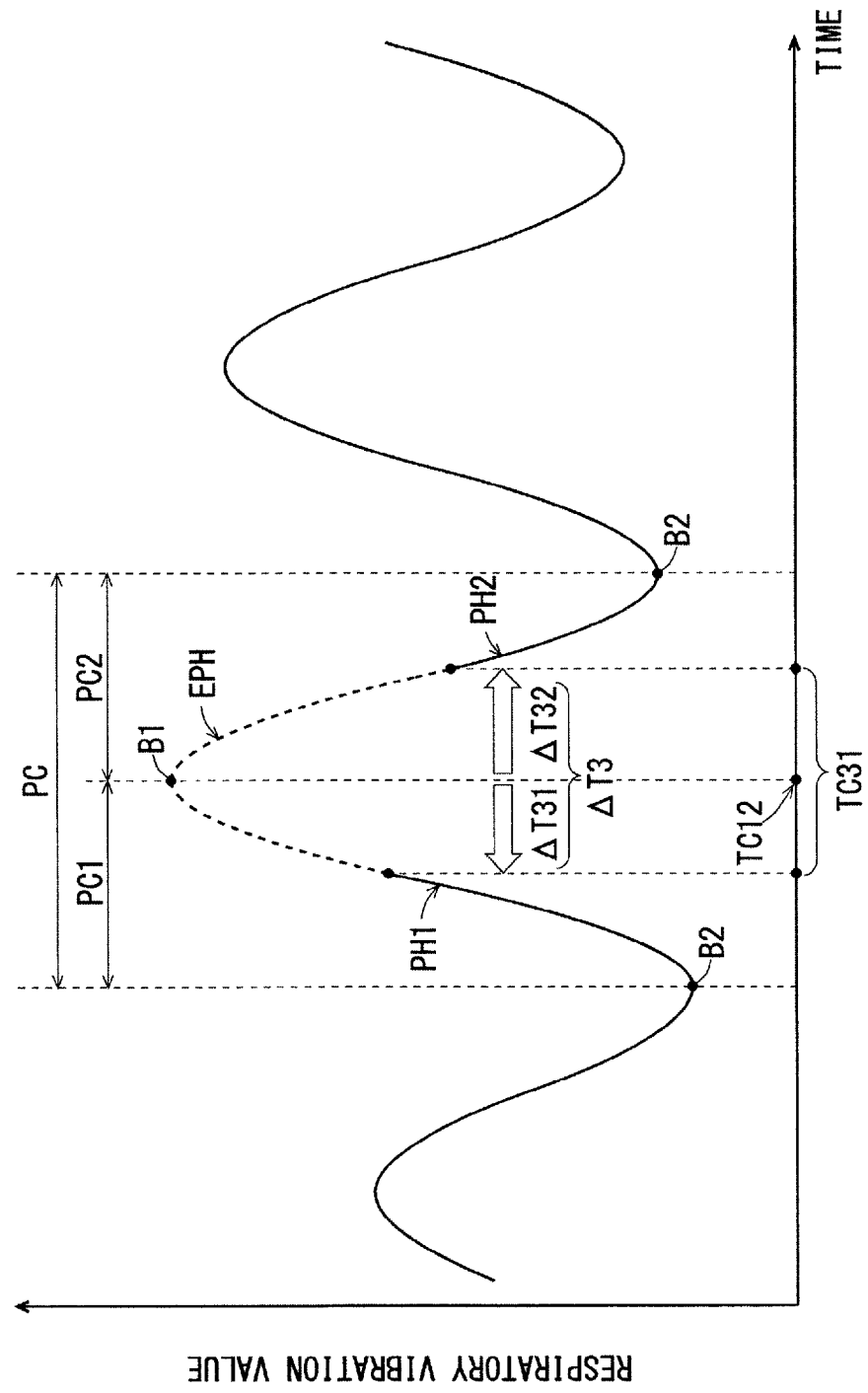
FIG. 20 is a diagram explaining a time-axis-direction extending processing.
Figure 21:
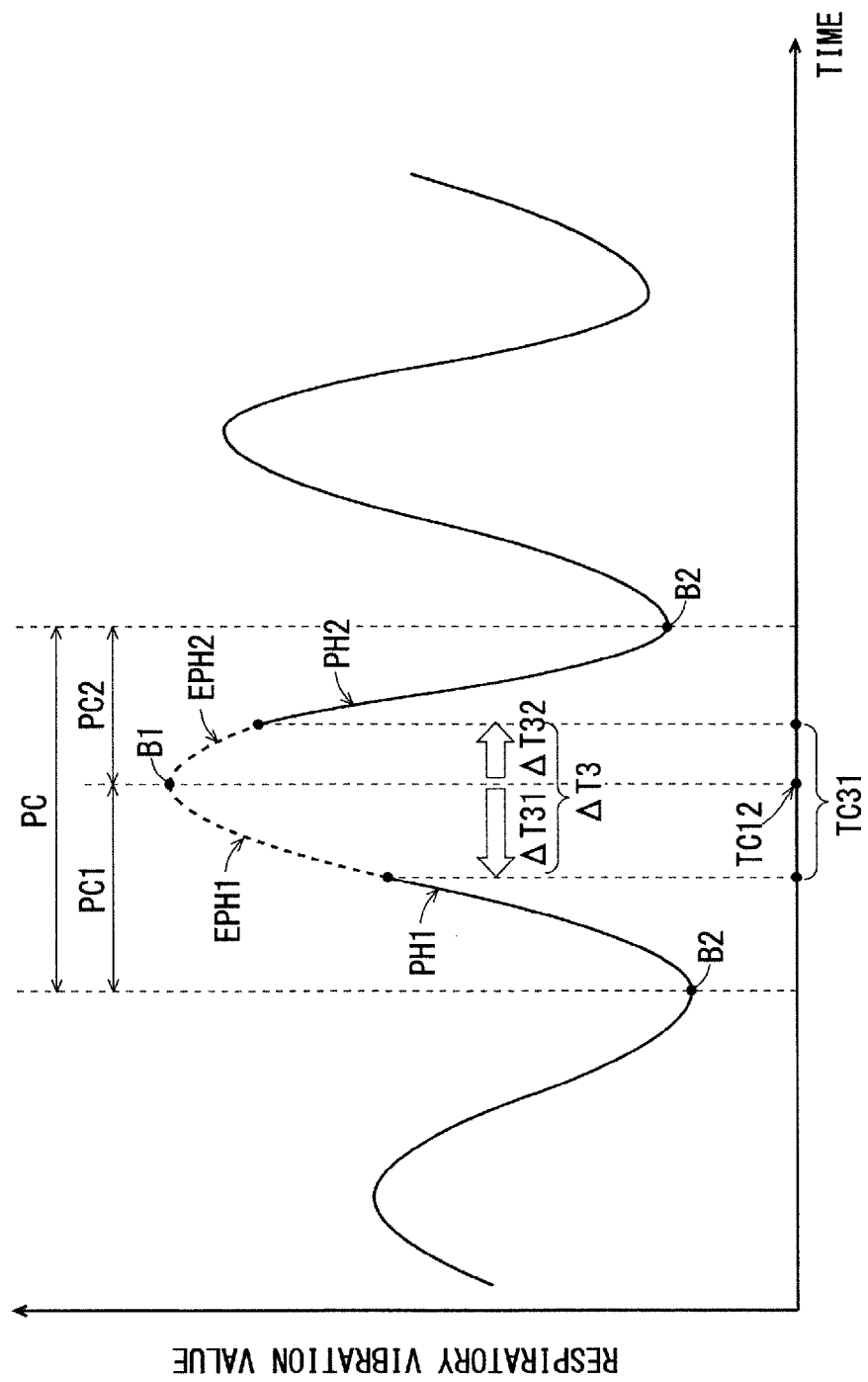
FIG. 21 is another diagram explaining the time-axis-direction extending processing.

FIG. 20 and FIG. 21 are diagrams explaining the first time-axis-direction extending processing, where the vertical axis represents a respiratory vibration value, and the horizontal axis represents a time at which a moving image is captured. As shown in FIG. 20, a combined time width of first and second time widths $\Delta T31$ and $\Delta T32$ is set as a time width $\Delta T3$. The first and second time widths $\Delta T31$ and $\Delta T32$ are determined on the basis of times PC1 and PC2 required for the inspiration phase PH1 and the expiration phase PH2, respectively, per respiratory period PC.

The first and second time widths $\Delta T31$ and $\Delta T32$, set per respiratory period PC, may be set as values specified by the user. In one method, the first and second time widths $\Delta T31$ and $\Delta T32$ may be determined as appropriate ratios to the times PC1 and PC2 required for the inspiration phase PH1 and the expiration phase PH2, respectively. For example, as shown in FIG. 20, the ratios may be changed in accordance with the times PC1 and PC2 required for the respective phases such that the first time width $\Delta T31$ is set as a value of 45% to the time PC1 required for the inspiration phase PH1 and that the second time width $\Delta T32$ is set as a value of 60% to the time PC2 required for the expiration phase PH2. Then, the blood-flow-restricted time TC31 can be changed in accordance with the time width $\Delta T3$.

Meanwhile, in an abnormal respiration state of the test subject M, for example, the time PC1 required for the inspiration phase PH1 may be longer than the time PC2 required for the expiration phase PH2 (see FIG. 21), or the time PC1 may be shorter than the time PC2. In such a case, the first time-axis-direction extending processing is extremely effective. In other words, the user can set the first and second time widths $\Delta T31$ and $\Delta T32$ at desired ratios, allowing the times in the inspiration phase EPH1 and the expiration phase EPH2, when it is assumed that a blood-flow-analysis value is adversely affected, to be directly included in the blood-flow-restricted time TC31 without the use of a respiratory amplitude value or the like.

<3-1-2. Second Time-Axis-Direction Extending Processing>

The second time-axis-direction extending processing is a processing of setting a time width $\Delta T$ as a time width determined on the basis of a time required for one period per respiratory period PC. Specifically, in the second time-axis-direction extending processing, a time width $\Delta T3$ (=$\Delta T31$+$\Delta T32$) is not determined on the basis of the times PC1 and PC2 required for the inspiration phase PH1 and the expiration phase PH2, respectively, as in the first time-axis-direction extending processing, but a time width $\Delta T$ is set on the basis of a time required for one period (a time obtained by adding an inspiration period PC1 and an expiration period PC2 in FIG. 20) PC. In this manner, the time width $\Delta T$ set per respiratory period PC can be determined as an appropriate ratio to the time PC required for one period, if the ratios are specified as 40% evenly, the time PC required for one period differs from respiratory period to respiratory period. In such a case, thus, a blood-flow-restricted time TC32 (not shown) varies in accordance with the time width $\Delta T$ per respiratory period.

The blood-flow-restricted time extending unit 131B extends the blood-flow-restricted time TC12 to provide a time width $\Delta T$ relative to the blood-flow-restricted time TC12 determined in the second blood-flow-restricted time determining processing, and the blood-flow-restricted time determining unit 130B determines a blood-flow-restricted time TC32.

<3-1-3. Third Time-Axis-Direction Extending Processing>

The third time-axis-direction extending processing is a processing of setting a time width $\Delta T$ as a predetermined time width. This causes a blood-flow-restricted time TC33 (not shown) to vary in accordance with the time width $\Delta T$ specified by the user. In other words, the blood-flow-restricted time extending unit 131B extends the blood-flow-restricted time TC11 or TC12 to provide a time width $\Delta T$ relative to the blood-flow-restricted time TC11 determined in the first blood-flow-restricted time determining processing or the blood-flow-restricted time TC12 determined in the second blood-flow-restricted time determining processing, and the blood-flow-restricted time determining unit 130B determines a blood-flow-restricted time TC33.

<3-1-4. Other Time-Axis-Direction Extending Processing>

The time width $\Delta T$ is set in the first to third time-axis-direction extending processings, which is not limited to these methods and may be set by another method. For example, the user may set a time width $\Delta T$ by specifying a desired numerical value per respiratory period PC or set a time width $\Delta T$ in consideration of the profile of a patient as described above.

<3-2. Basic Operation of Image Processing Apparatus 3B>

Figure 22:
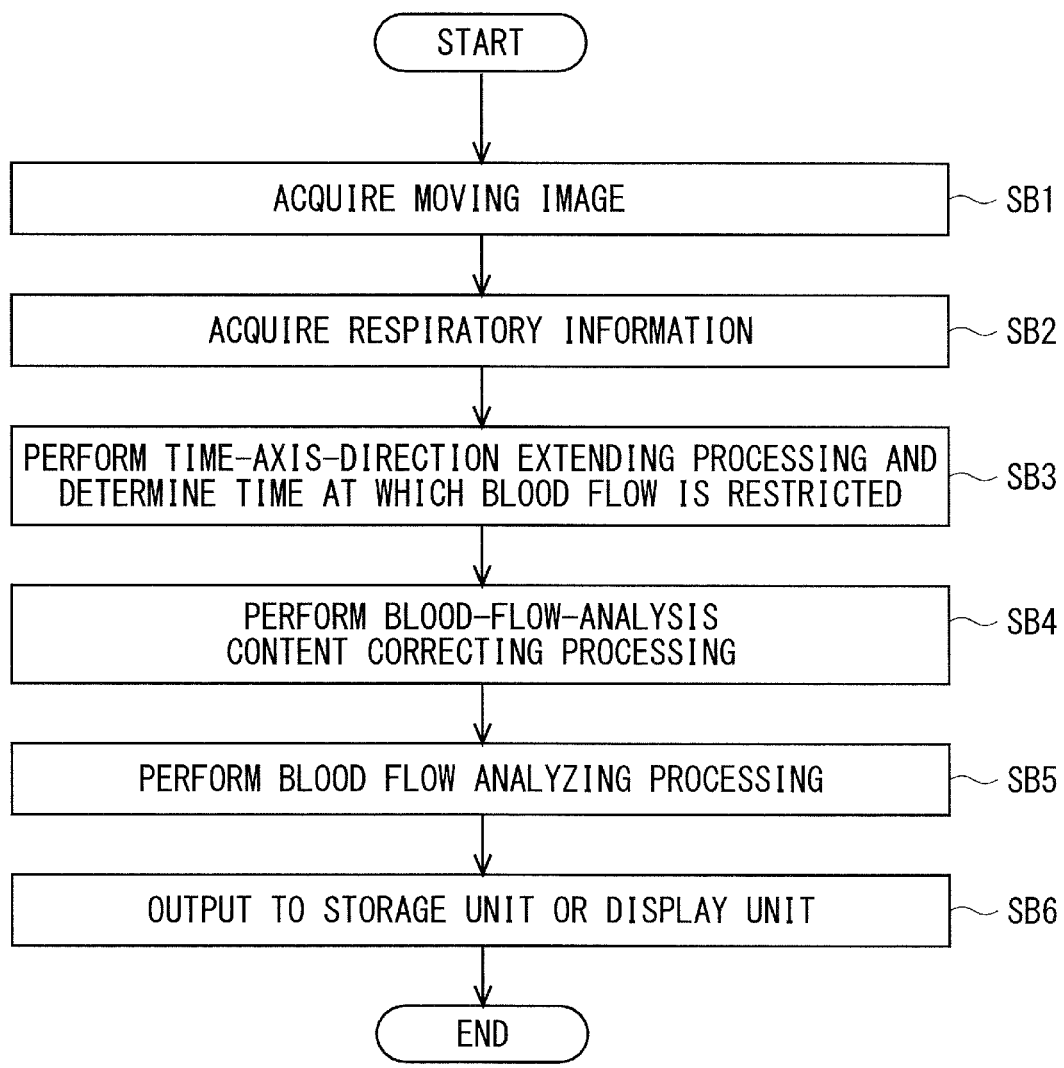
FIG. 22 is a flowchart explaining the basic operation of the image processing apparatus 3B achieved in the third embodiment.

FIG. 22 is a diagram illustrating the operational flow of the image processing apparatus 3B according to the third embodiment. FIG. 22 illustrates a representative example in which the blood-flow-analysis content correcting processing is the preprocessing (a1) or (a2). Steps SB1, SB2, and SB4 to SB6 of FIG. 22 are similar to Steps S1, S2, and S4 to S6 of FIG. 11, which will not be described here.

In the third embodiment, the blood-flow-restricted time extending unit 131B (time-axis-direction extending unit 133), which is not provided in the first embodiment, is added, and thus, only the following steps are changed.

In other words, after Steps SB1 and SB2 as steps similar to the steps of the first embodiment, as shown in FIG. 22, the blood-flow-restricted time determining unit 130B performs the first or second blood-flow-restricted time determining processing in Step SB3. Then, the time-axis-direction extending unit 133 sets a time width ΔT in any one of the first to third time-axis-direction extending processings, thereby determining a blood-flow-restricted time TC.

Specifically, in the case where the blood-flow-restricted time determining unit 130B performs the first blood-flow-restricted time determining processing, the time-axis-direction extending unit 133 sets a time width ΔT in the third time-axis-direction extending processing, thereby determining a blood-flow-restricted time TC33. In the case where the blood-flow-restricted time determining unit 130B performs the second blood-flow-restricted time determining processing, meanwhile, the time-axis-direction extending unit 133 sets a time width ΔT in any one of the first to third time-axis-direction extending processings, thereby determining a blood-flow-restricted time TC, namely, any of TC31 to TC33 (see FIG. 20 and FIG. 21).

The remaining steps are performed as in the first embodiment.

As described above, in the image processing apparatus 3B according to third embodiment, the blood-flow-restricted time determining unit 130B includes the blood-flow-restricted time extending unit 131B that extends the blood-flow-restricted time TC11 or TC12 to provide a time width ΔT relative to the blood-flow-restricted time TC11 or TC12. This restricts a blood flow, extending a time period assumed to adversely affect a blood-flow-analysis value.

The time width ΔT is a time width determined in any of the first to third time-axis-direction extending processings. Thus, in the use of the first time-axis-direction extending processing of setting a time width on the basis of the times PC1 and PC2 required for the respective phases, a time width ΔT3 (=ΔT31+ΔT32) to be set will not be relatively long compared with the times PC1 and PC2 required for the respective phases, allowing a blood-flow-restricted time TC31 to be appropriately extended and determined (see FIG. 20). If the time required for the inspiration phase PH1 differs from the time required for the expiration phase PH2, a time width ΔT3 can be set appropriately by a combination of the first and second time widths ΔT31 and ΔT32 in accordance with the inspiration phase PH1 and the expiration phase PH2 (see FIG. 21). This allows the blood-flow-restricted time TC31 to be determined suitably for patients who have difficulty in respiration in which the time PC1 required for the inspiration phase PIll differs from the time PC2 required for the expiration phase PH2 (see FIG. 20 and FIG. 21).

When a time width is set on the basis of a time required for one period, meanwhile, it suffices to calculate only a time PC required for one period without calculating the times PC1 and PC2 required for the inspiration phase PH1 and the expiration phase PH2, respectively, reducing a calculation time.

In the use of the third time-axis-direction extending processing of setting a predetermined time width, the blood-flow-restricted times TC11 and TC12 can be easily extended to determine the blood-flow-restricted time TC32, independently of a respiratory vibration value at each time (that is, without calculating a time of a respiratory phase).

4. Fourth Embodiment

FIG. 23 is a diagram showing the functional configuration of a control unit 31C to be used in an image processing apparatus 3C configured as a fourth embodiment of the present invention. The control unit 31C is used in place of the control unit 31 in the image processing apparatus 3 of the first embodiment (see FIG. 3). The fourth embodiment differs from the first embodiment in that a blood-flow-restricted time limiting unit 140 is added. The blood-flow-restricted time determining unit 130C has a function similar to that of the blood-flow-restricted time determining unit 130 of the first embodiment. The blood-flow-restricted time determining unit 130C, however, differs from the blood-flow-restricted time determining unit 130 in that it exchanges signals with the blood-flow-restricted time limiting unit 140. The remaining units are similar to those of the image processing apparatus 3.

Figure 24:
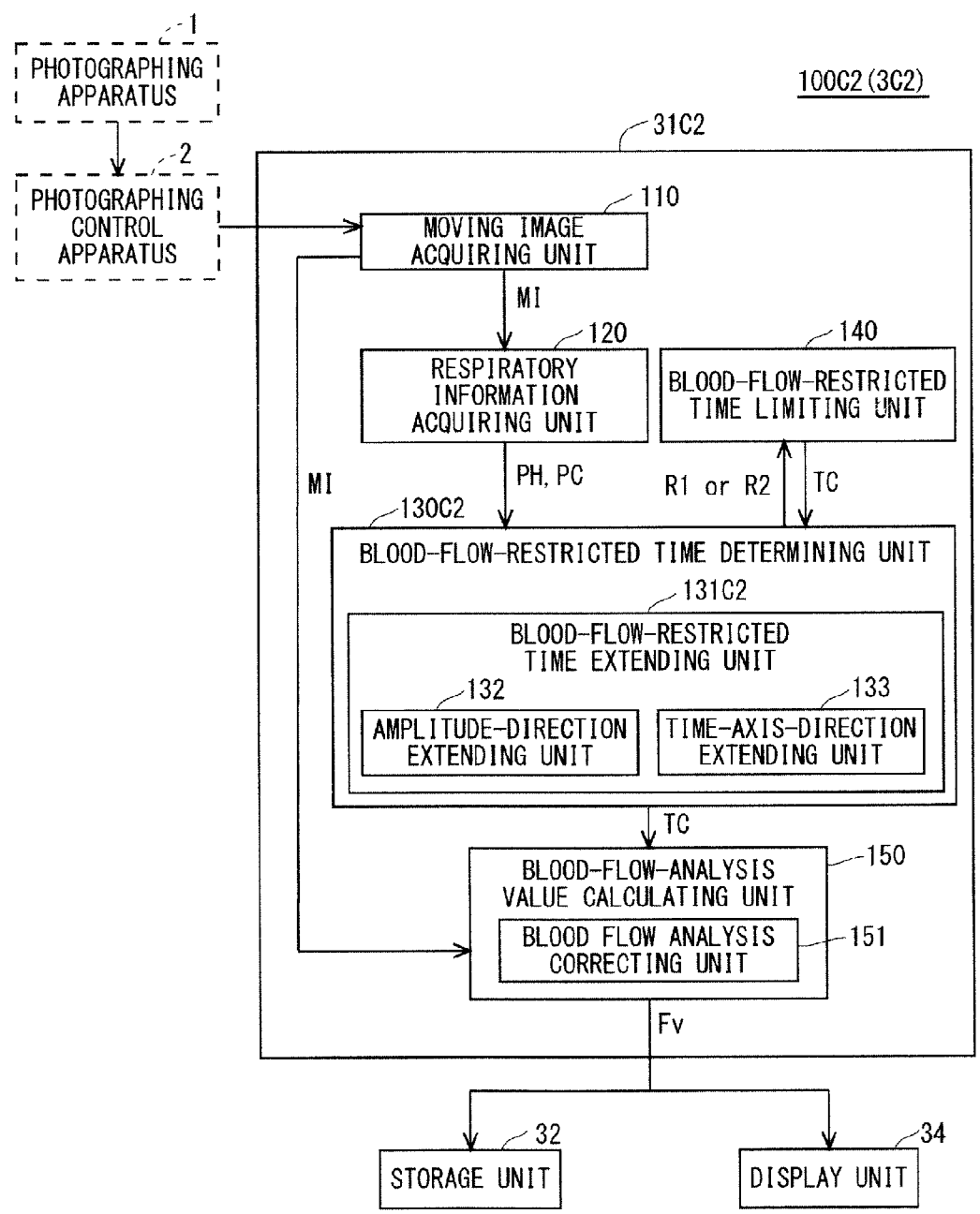
FIG. 24 is a block diagram showing the functional configuration of a modification of the image processing apparatus 3C according to the fourth embodiment.

FIG. 24 shows a modification of the image processing apparatus 3C, which is a diagram showing the functional configuration of a control unit 31C2 to be used in an image processing apparatus 3C2. In other words, the image processing apparatus 3C2 differs from the image processing apparatus 3C in that, as shown in FIG. 24, in the image processing apparatus 3C2, the blood-flow-restricted time determining unit 130C2 includes a blood-flow-restricted time extending unit 131C2 and the blood-flow-restricted time extending unit 131C2 includes the amplitude-direction extending unit 132 and the time-axis-direction extending unit 133. In other words, the image processing apparatus 3C2 has a configuration in which the second and third embodiments are combined and the blood-flow-restricted time limiting unit 140 is further added.

FIG. 24 shows an example modification of the image processing apparatus 3C. For example, the blood-flow-restricted time extending unit 131C2 may include only the amplitude-direction extending unit 132 or only the time-axis-direction extending unit 133.

<4-1. Blood-Flow-Restricted Time Limiting Unit 140>

The blood-flow-restricted time limiting unit 140 limits the blood-flow-restricted time determining unit 130C or 130C2 (blood-flow-restricted time determining processing) to satisfy any one of (e1) a condition that the total time required for analysis, which is used in blood flow analysis at times other than the blood-flow-restricted time TC, is not less than a first reference time and (e2) a condition that the time required for analysis, which is used in blood flow analysis at times other than the blood-flow-restricted time TC, per respiratory period PC is not less than a second reference time (see FIG. 23 and FIG. 24).

Figure 25:
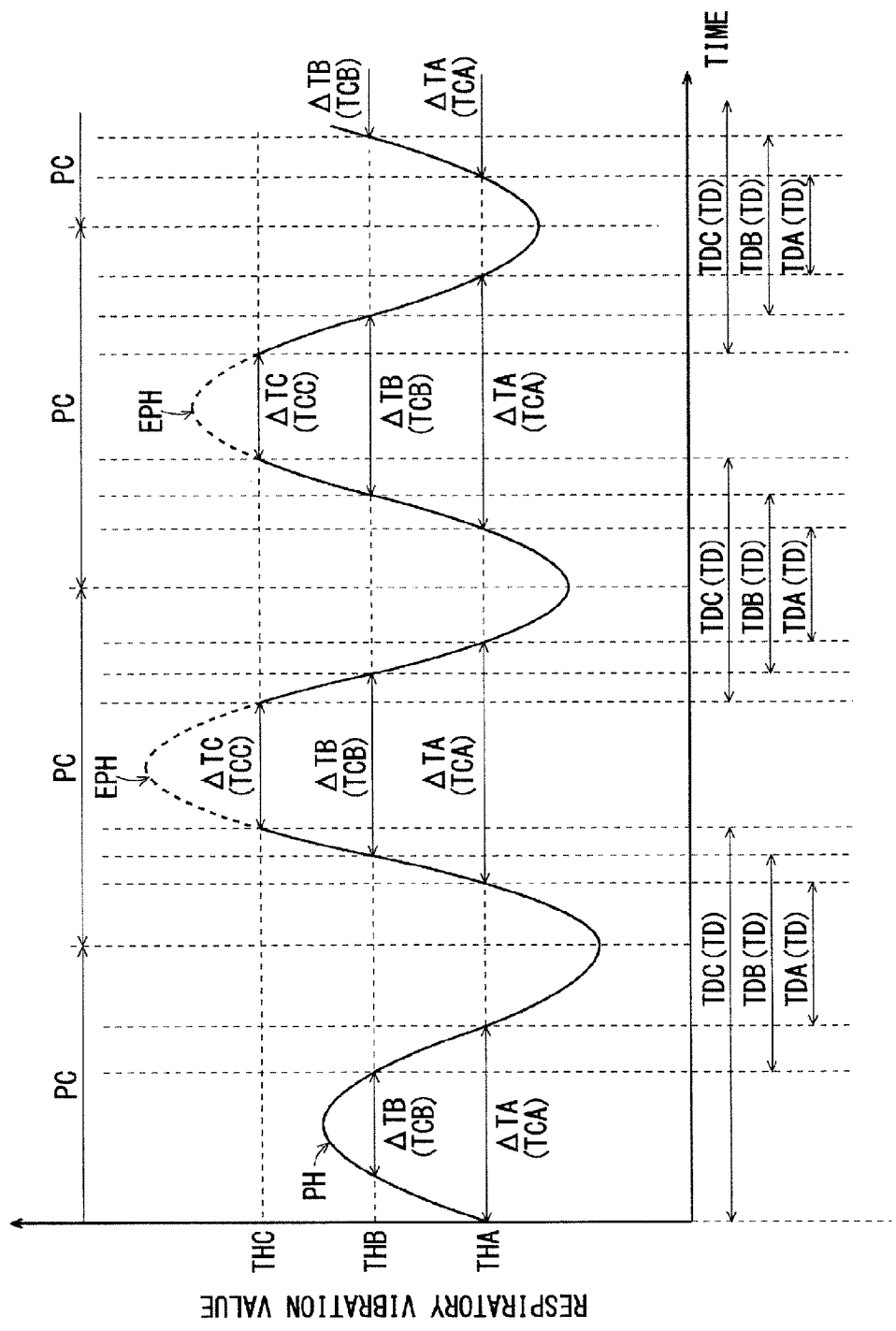
FIG. 25 is a diagram explaining a processing of limiting the blood-flow-restricted time determining processing.

FIG. 25 is a diagram explaining a processing of limiting the blood-flow-restricted time determining processing, where the vertical axis represents a respiratory vibration value, and the horizontal axis represents a time at which a moving image is captured.

The correspondence between FIG. 25 and FIG. 23 in the case where the configuration of FIG. 23 is employed and the correspondence between FIG. 25 and FIG. 24 in the case where the configuration of FIG. 24 is employed will be described below individually.

In the case where the blood-flow-restricted time limiting unit 140 shown in FIG. 23 limits the blood-flow-restricted time determining unit 130C, the reference values SV in the third blood-flow-restricted time determining processing (see FIG. 10) correspond to thresholds THA, THB, and THC (see FIG. 25), and the blood-flow-restricted times TC13 (see FIG. 10) correspond to TCA, TCB, and TCC (see FIG. 25).

Meanwhile, the case where the blood-flow-restricted time limiting unit 140 shown in FIG. 24 limits the blood-flow-restricted time determining unit 130C2 may be the case where the blood-flow-restricted time limiting unit 140 limits the amplitude-direction extending unit 132 and/or the case where the blood-flow-restricted time limiting unit 140 limits the time-axis-direction extending unit 133.

In the case where the blood-flow-restricted time limiting unit 140 limits the amplitude-direction extending unit 132, the first thresholds TH1 in the first amplitude-direction extending processing (see FIG. 14 and FIG. 16) correspond to THA, THB, and THC (see FIG. 25), the time widths ΔT21 and ΔT23 (see FIG. 14 and FIG. 16) correspond to ΔTA, ΔTB, and ΔTC (see FIG. 25), and the blood-flow-restricted times TC21 and TC23 (see FIG. 14 and FIG. 16) correspond to TCA, TCB, and TCC (see FIG. 25). Meanwhile, the second thresholds TH2 in the second amplitude-direction extending processing (see FIG. 15 and FIG. 17) correspond to thresholds THA, THB, and THC (see FIG. 25), the time widths ΔT22 and ΔT24 (see FIG. 15 and FIG. 17) correspond to ΔTA, ΔTB, and ΔTC (see FIG. 25), and the blood-flow-restricted times TC22 and TC24 (see FIG. 15 and FIG. 17) correspond to TCA, TCB, and TCC (see FIG. 25).

In the case where the blood-flow-restricted time limiting unit 140 limits the time-axis-direction extending unit 133, the time widths ΔT in any of the first to third time-axis-direction extending processings (see FIG. 20 and FIG. 21) correspond to ΔTA. ΔTB, and ΔTC (see FIG. 25), and the blood-flow-restricted times TC31 and TC32 (see FIG. 20 and FIG. 21) correspond to TCA, TCB, and TCC (see FIG. 25).

In any case, as described above, changing a blood-flow-restricted time in the order of TCA, TCB, and TCC (a time width is changed in the order of ΔTA, ΔTB, and ΔTC) causes a time required for analysis to shift in the order of TDA, TDB, and TDC (see FIG. 25). For example, when the blood-flow-restricted time determining unit 130C or 130C2 first sets the blood-flow-restricted time to TCA, the blood-flow-restricted time limiting unit 140 limits the blood-flow-restricted time determining unit 130C or 130C2 to satisfy any one of (e1) a condition that a total time of the times required for analysis TDA (a total number of frame images), which are used in blood flow analysis at times other than the blood-flow-restricted time TCA, in an overall time is not less than a first reference time (first number of frame images) and (e2) a condition that the time required for analysis TDA (the number of frame images), which is used in blood flow analysis at times other than the blood-flow-restricted time TCA, per respiratory period PC is not less than a second reference time (second number of frame images) N2. Here, the first reference time (first number of frame images) N1 is preferably a time (the number of frame images) corresponding to three periods of blood flow, and the second reference time (second number of frame images) N2 is preferably a time (the number of frame images) corresponding to one period of blood flow.

Providing that a first ratio of the time required for analysis TDA, which is used for blood flow analysis at times other than the blood-flow-restricted time TCA, to an overall time is represented by R1 and that a second ratio of the time required for analysis TDA, which is used for blood flow analysis at times other than the blood-flow-restricted time TCA, to the respiratory period PC is represented by R2 per respiratory period PC, the first ratio R1 and the second ratio R2 are preferably at least 30% or more in terms of percentage.

When judging that the condition (e1) or (e2) is not satisfied and that "the total time of the times required for analysis TDA in the overall time is shorter than a first reference time N1" or that "the time required for analysis TDA of the respiratory period PC is shorter than the second reference time N2" (that is, the time required for analysis TDA is short), the blood-flow-restricted time limiting unit 140 instructs the blood-flow-restricted time determining unit 130C or 130C2 to set the blood-flow-restricted time to a TCB whose time width is shorter than that of TCA. The blood-flow-restricted time is set to TCB, so that the time required for analysis increases from TDA to TDB, and the blood-flow-restricted time limiting unit 140 again judges whether the condition (e1) or (e2) is satisfied. If the condition is satisfied, the blood-flow-restricted time limiting unit 140 instructs the blood-flow-restricted time determining unit 130C or 130C2 to set the blood-flow-restricted time to TCB.

If the condition is not satisfied, the blood-flow-restricted time limiting unit 140 instructs the blood-flow-restricted time determining unit 130C or 130C2 to determine TCC whose time width is shorter than that of the TCB as the blood-flow-restricted time. TCC is determined as the blood-flow-restricted time, so that the time required for analysis increases from TDB to TDC, and the blood-flow-restricted time limiting unit 140 again judges whether the condition (e1) or (e2) is satisfied.

The blood-flow-restricted times TC are set in order as described above, and this loop is repeatedly performed until the condition (e1) or (e2) is eventually satisfied. Then, the time width at the judgment stage in the loop is determined as a blood-flow-restricted time IC.

The example above has described that blood-flow-restricted time TCs are determined from a longer time width to a shorter time width in the order of TCA (ΔTA). TCB (ΔTB), and TCC (ΔTC), which is not limited thereto. In another method, blood-flow-restricted times TC may be determined from a shorter time width to a longer time width in the order of TCC (ΔTC), TCB (ΔTB), and TCA (ΔTA). In this case, the loop is repeatedly performed until it is eventually judged that the condition (e1) or (e2) is not satisfied, and the time width at the stage prior to the judgment in the loop is set as a blood-flow-restricted time IC.

As described above, the addition of the blood-flow-restricted time limiting unit 140 allows a blood-flow-restricted time TC to be determined while keeping a blood flow analysis time required for the user.

As described above, the example of FIG. 25 has been given for the blood-flow-restricted time limiting unit 140 shown in FIG. 23 and FIG. 24. As to the blood-flow-restricted time limiting unit 140 shown in FIG. 23, only the third blood-flow-restricted time determining processing has been described. The blood-flow-restricted time limiting unit 140 shown in FIG. 23 mainly performs the third blood-flow-restricted time determining processing of setting a blood-flow-restricted time with a time width. In the example as described below, also, the blood-flow-restricted time limiting unit 140 is effective for the first and second blood-flow-restricted time determining processings.

Figure 34:
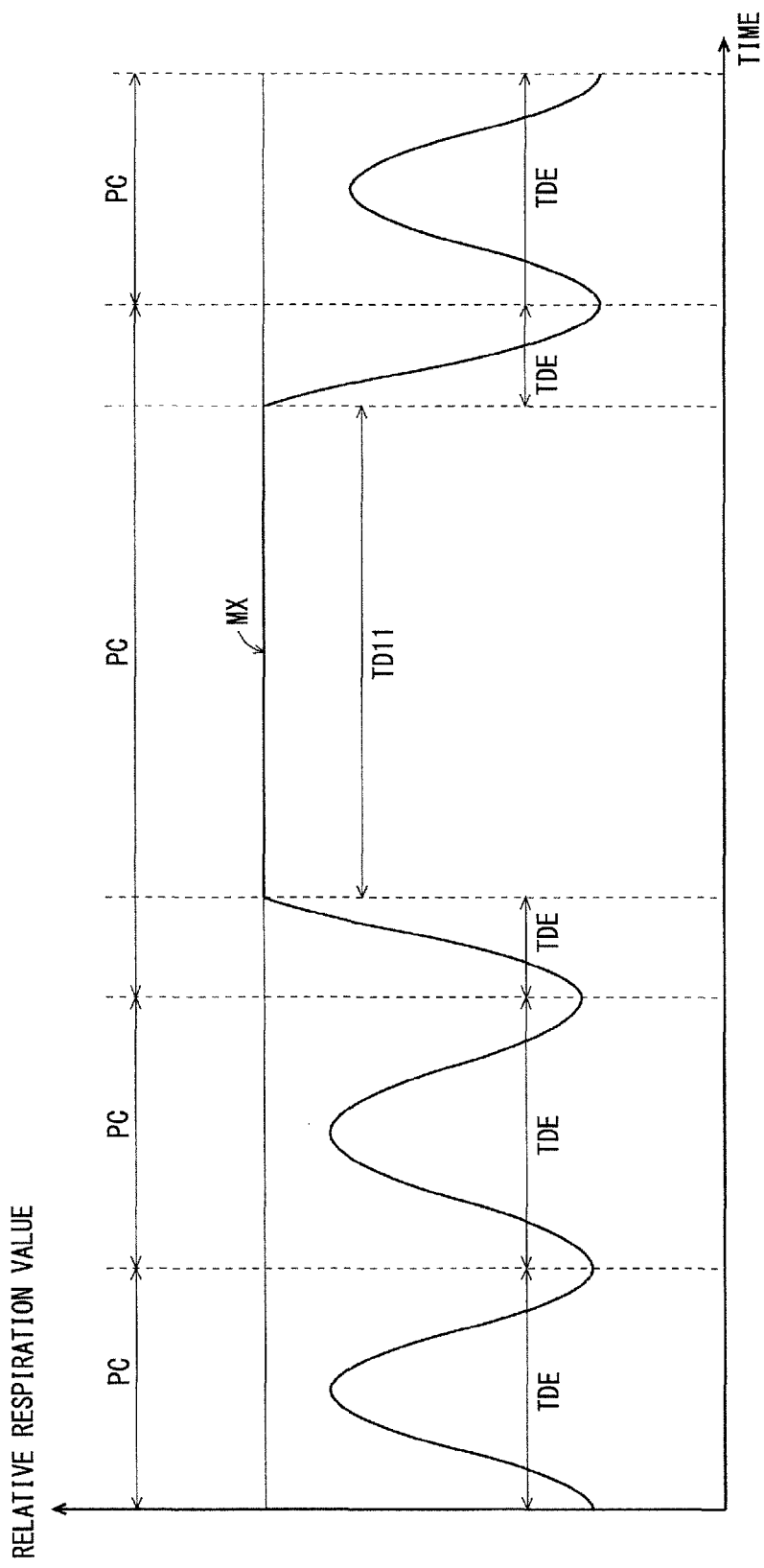
FIG. 34 is a diagram explaining a processing of limiting the blood-flow-restricted time determining processing.

FIG. 34 is a diagram explaining the processing of limiting the first blood-flow-restricted time determining processing in the configuration of FIG. 23, where the vertical axis represents a respiratory vibration value, and the horizontal axis represents a time at which a moving image is captured. As shown in FIG. 34, a moving image is captured while breath is being held in the maximum inspiration phase, and thus, there is a time with a time width at which the respiratory vibration value is a maximum value MX. When the first blood-flow-restricted time determining processing is performed, accordingly, the blood-flow-restricted time IC 11 is determined with a time width, so that the time excluding the blood-flow-restricted time TC11 becomes a time required for analysis TDE. The blood-flow-restricted time limiting unit 140 therefore limits the blood-flow-restricted time determining unit 130C (first blood-flow-restricted time determining processing) to satisfy any one of (e1) the condition that "the total time of times required for analysis TDE in the overall time is not less than the first reference time N1" and (e2) the condition that "the time required for analysis TDE per respiratory period PC is not less than the second reference time N2" (see FIG. 23).

When a moving image is captured without breath holding as shown in FIG. 9, the maximum value MX of the respiratory vibration values is fixed as a single point, and thus, the blood-flow-restricted time TC11 has no time width. In the case where a moving image is captured during breath holding as shown in FIG. 34, contrastingly, the maximum value MX of the respiratory vibration values continues. This provides a time width to the blood-flow-restricted time TC11, so that the function of the blood-flow-restricted time limiting unit 140 becomes effective. Particularly in the condition (e2), judgment is made per respiratory period PC, and thus, the blood-flow-restricted time limiting unit 140 operates effectively in the case where analysis is performed per respiratory period PC.

Although FIG. 34 solely explains the first blood-flow-restricted time determining processing, the blood-flow-restricted time limiting unit 140 achieves similar effects also in the second blood-flow-restricted time determining processing.

<4-2. Basic Operation of Image Processing Apparatus 3C>

Figure 26:
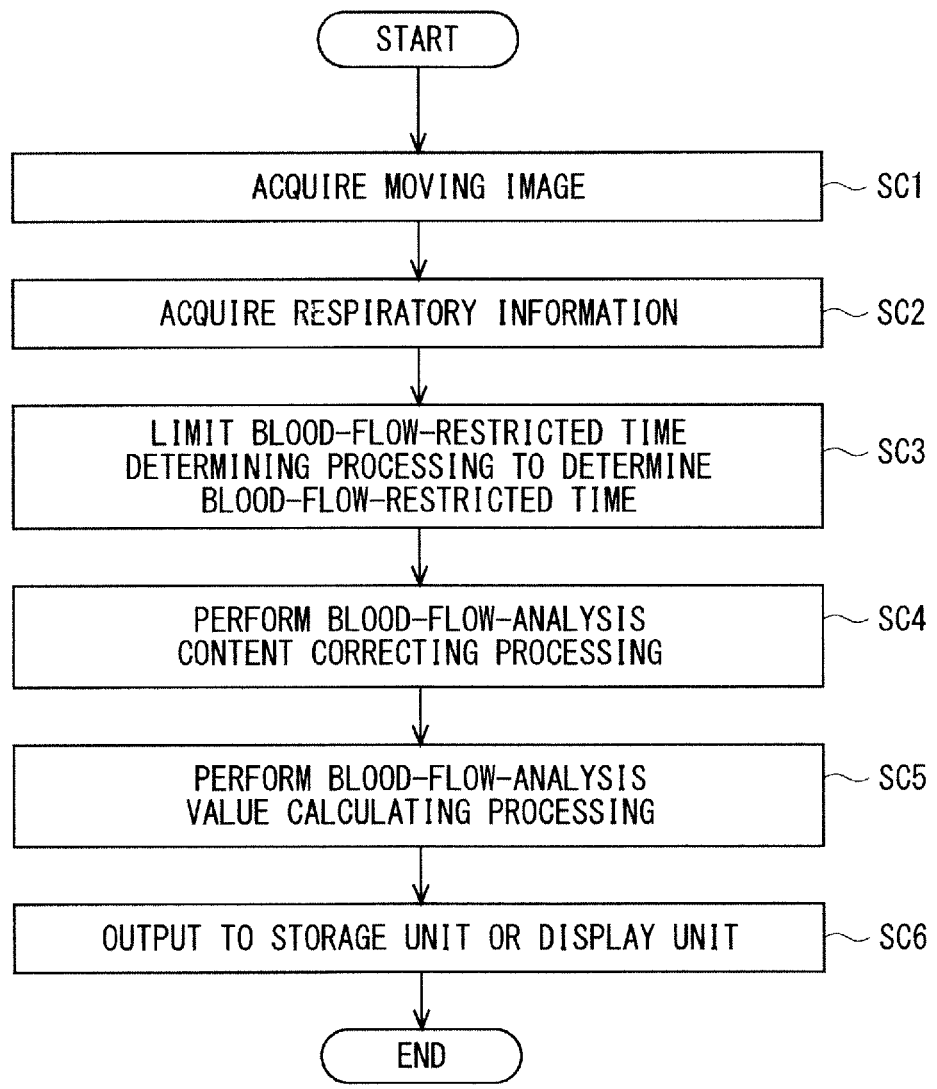
FIG. 26 is a flowchart explaining the basic operation of the image processing apparatus 3C achieved in the fourth embodiment.

FIG. 26 is a diagram illustrating the operational flow of the image processing apparatus 3C according to the fourth embodiment. FIG. 26 shows a representative case where the blood-flow-analysis content correcting processing is the preprocessing (a1) or (a2). Steps SC1, SC2, and SC4 to SC6 of FIG. 26 are similar to Steps S1, S2, and S4 to S6 of FIG. 11, which will not be described here.

The blood-flow-restricted time limiting unit 140, which is not provided in the first embodiment, is added in the fourth embodiment, and thus, only the following steps are changed.

In other words, through Steps SC1 and SC2 as steps similar to the steps of the first embodiment, as shown in FIG. 26, the blood-flow-restricted time limiting unit 140 limits the blood-flow-restricted time determining unit 130C or 130C2 (blood-flow-restricted time determining processing) to satisfy any one of the conditions (e1) and (e2) in Step SC3, so that the blood-flow-restricted time determining unit 130C or 130C2 determines an appropriate blood-flow-restricted time TC (see FIG. 25).

The remaining steps are performed as in the first embodiment.

As described above, the image processing apparatus 3C according to the fourth embodiment further includes the blood-flow-restricted time limiting unit 140 that limits the blood-flow-restricted time determining processing. Thus, a minimum amount of data in the time required for analysis TD used for blood flow analysis can be allocated, enabling appropriate dynamic diagnosis of a blood flow.

5. Fifth Embodiment

Figure 27:
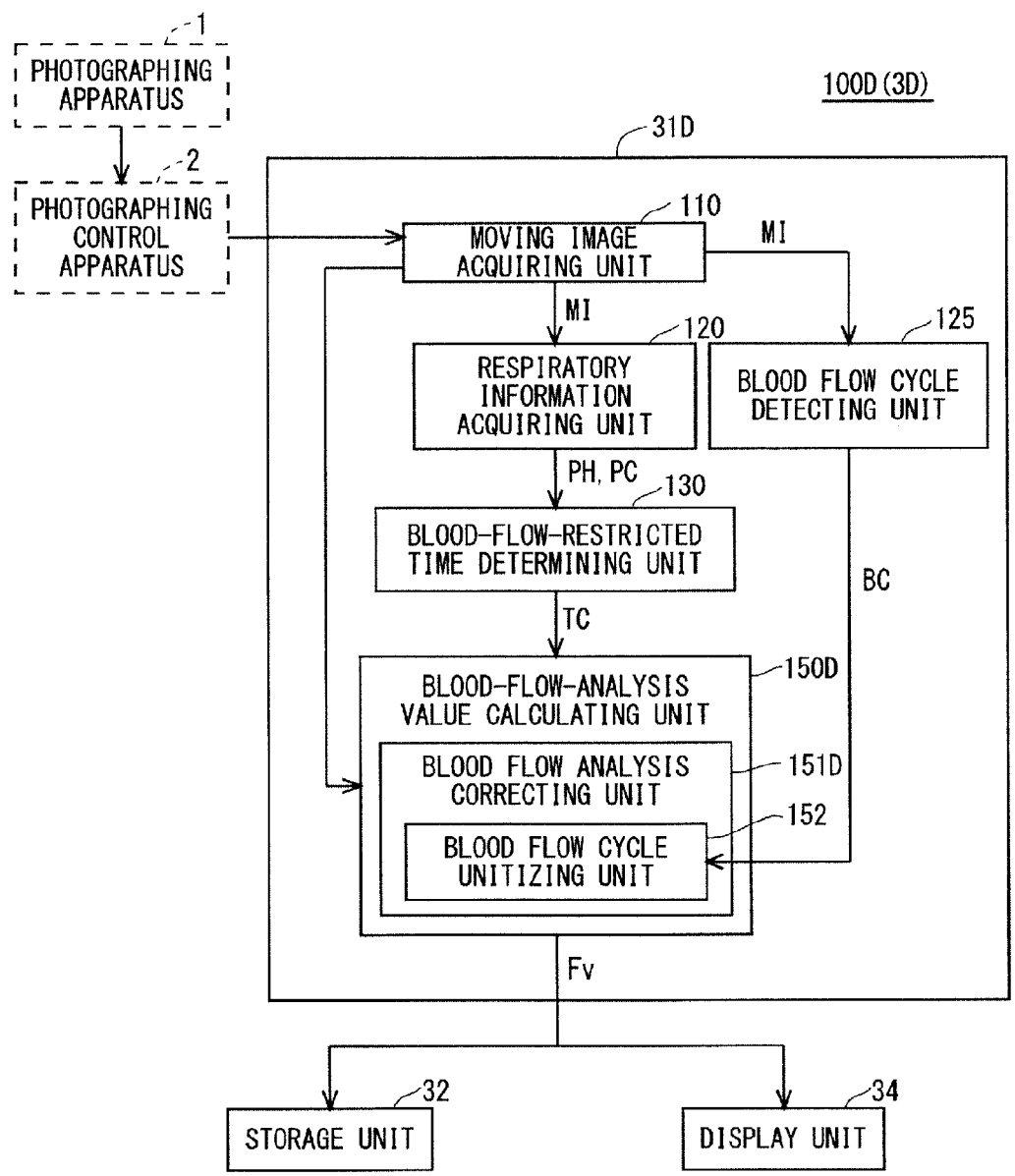
FIG. 27 is a block diagram showing the functional configuration of an image processing apparatus 3D according to a fifth embodiment.

FIG. 27 is a diagram showing the functional configuration of a control unit 31D to be used in an image processing apparatus 3D configured as a fifth embodiment of the present invention. The control unit 31D is used in place of the control unit 31 in the image processing apparatus 3 of the first embodiment (see FIG. 3). The fifth embodiment differs from the first embodiment in that a blood flow cycle detecting unit 125 is added and that a blood-flow-analysis value calculating unit 150D and a blood flow analysis correcting unit 151D that have similar functions as those of the blood-flow-analysis value calculating unit 150 and the blood flow analysis correcting unit 151 of the first embodiment include a blood flow cycle unitizing unit 152. The remaining components are similar to those of the image processing apparatus 3.

Figure 28:
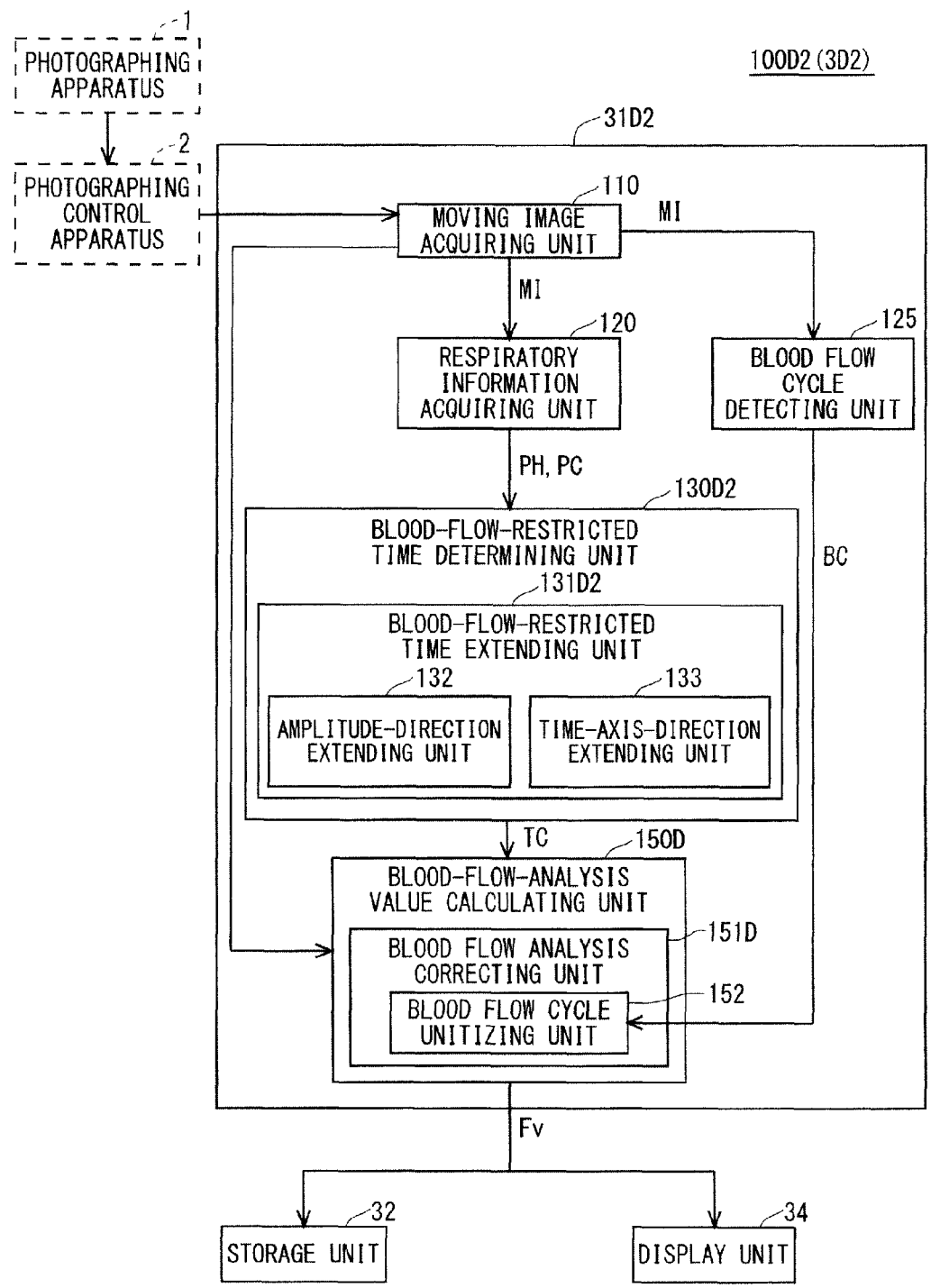
FIG. 28 is a block diagram showing the functional configuration of a modification of the image processing apparatus 3D according to the fifth embodiment.

FIG. 28 shows a modification of the image processing apparatus 3D, which shows the functional configuration of a control unit 31D2 to be used in the image processing apparatus 3D2. In other words, the modification differs from the image processing apparatus 3D in that as shown in FIG. 28, in the image processing apparatus 3D2, the blood-flow-restricted time determining unit 130D2 includes a blood-flow-restricted time extending unit 131D2 and that the blood-flow-restricted time extending unit 131D2 includes the amplitude-direction extending unit 132 and the time-axis-direction extending unit 133. In other words, the image processing apparatus 3D2 has the configuration in which the second and the third embodiments are further combined and the blood flow cycle detecting unit 125 and the blood flow cycle unitizing unit 152 are further added.

FIG. 28 shows an example of the modification of the image processing apparatus 3D. For example, the blood-flow-restricted time extending unit 131D2 may include only the amplitude-direction extending unit 132 or only the time-axis-direction extending unit 133.

<5-1. Blood Flow Cycle Detecting Unit 125>

The blood flow cycle detecting unit 125 detects the blood flow cycle of a target pixel in a target region using a plurality of frame images MI acquired by the moving image acquiring unit 110. In one method of detecting a blood flow cycle, for example, a difference between frame images MI is obtained, and a change in the density value (namely, a change in the blood-flow amount) of a pixel (target pixel) whose signal is clear in the target region is regarded as a blood flow phase, thereby detecting a blood flow cycle on the basis of the blood flow phase.

Figure 29:
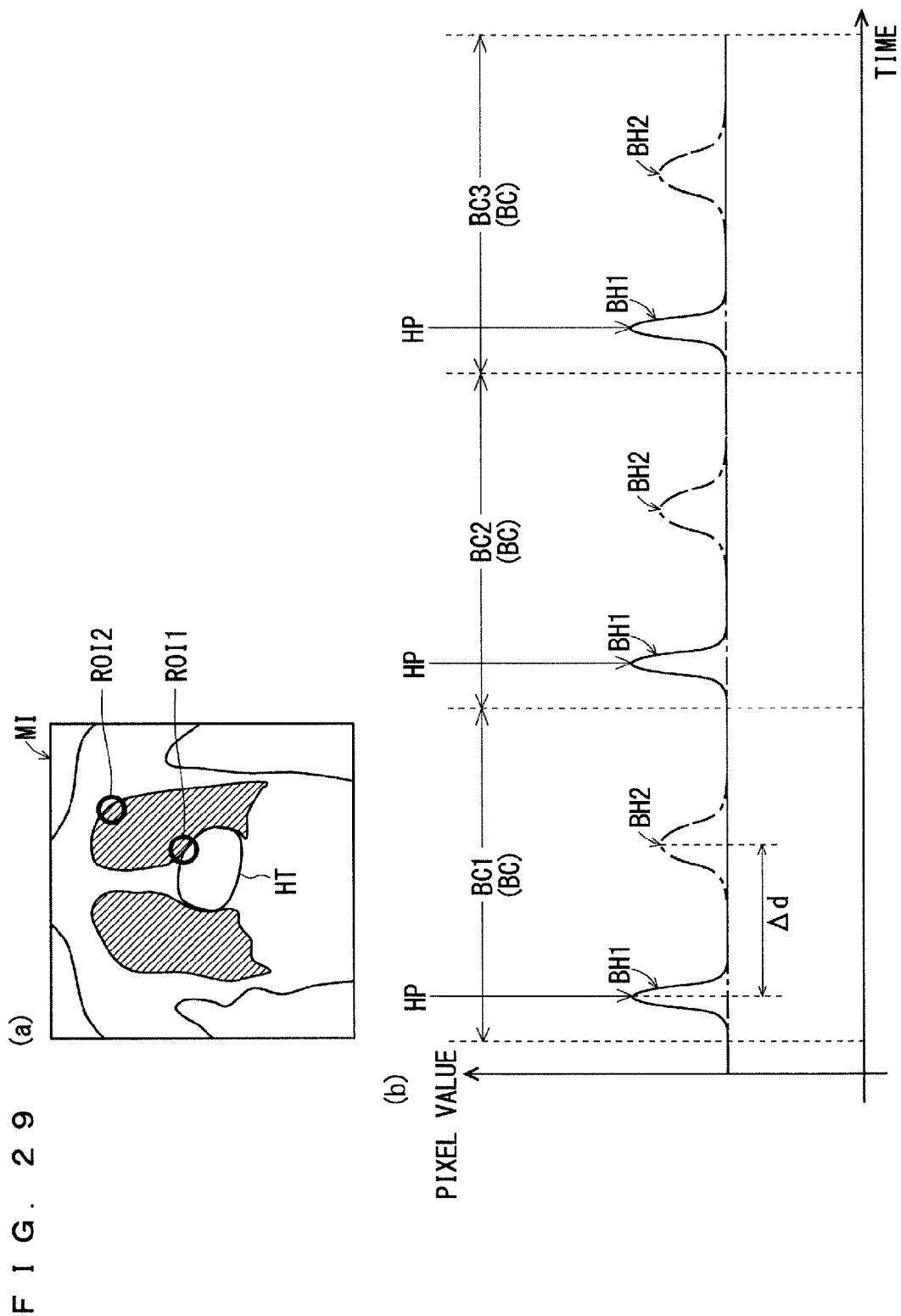
FIG. 29 is a diagram explaining a blood flow cycle achieved from a plurality of frame images.

FIG. 29 is a diagram explaining blood flow phases and blood flow cycles that are detected from a plurality of frame images MI by the blood flow cycle detecting unit 125. Part (a) of FIG. 29 shows the positions of target regions (target pixels) ROI1 and ROI2 of the frame image MI, and part (b) of FIG. 29 shows blood flow phases and blood flow cycles in the target pixels ROI1 and ROI2. The vertical axis of part (b) of FIG. 29 represents pixel values (blood flow amounts) of the target pixels ROI1 and ROI2 acquired by obtaining a difference between frame images MI, and the horizontal axis of part (b) of FIG. 29 represents times at which a moving image is captured.

Part (b) of FIG. 29 shows an example of detecting blood flow cycles BC1 to BC3 with reference to the blood flow phase BH1 of the target region ROI1 detected by the blood flow cycle detecting unit 125. The method of determining the blood flow cycles BC1 to BC3 may be, for example, a method of searching for a rise on the basis of a highest value HP of the blood flow phase BH1 and determining a blood flow cycle with reference to the rise.

Meanwhile, in the selection of the target region ROI2 located farther from the heart HT than the target region ROI1 (see part (a) of FIG. 29), a change as indicated by the blood flow phase BH2, which has a phase gap Δd between the blood flow phase BH1 and the blood flow phase BH2, is shown (see part (b) of FIG. 29). The blood flow phase typically depends on factors such as the distance from the heart HT and how a blood flow runs. Thus, the blood flow phase of a target region can be estimated from a pixel whose signal is clear. A signal of a pixel closer to the heart HT is generally clearer than a signal of a pixel farther from the heart HT. For example, to perform a blood flow analysis also on the target region ROI2, accordingly, the blood flow phase BH2 of the target region ROI2 can be estimated after the blood flow phase BH of the target region ROI1 is obtained.

<5-2. Blood Flow Cycle Unitizing Unit 152>

The blood flow cycle unitizing unit 152 adjusts a blood-flow-restricted time TC such that a blood flow analysis is performed on the blood-flow-restricted time TC set in the blood-flow-restricted time determining processing in units of blood flow cycle BC detected by the blood flow cycle detecting unit 125.

Figure 30:
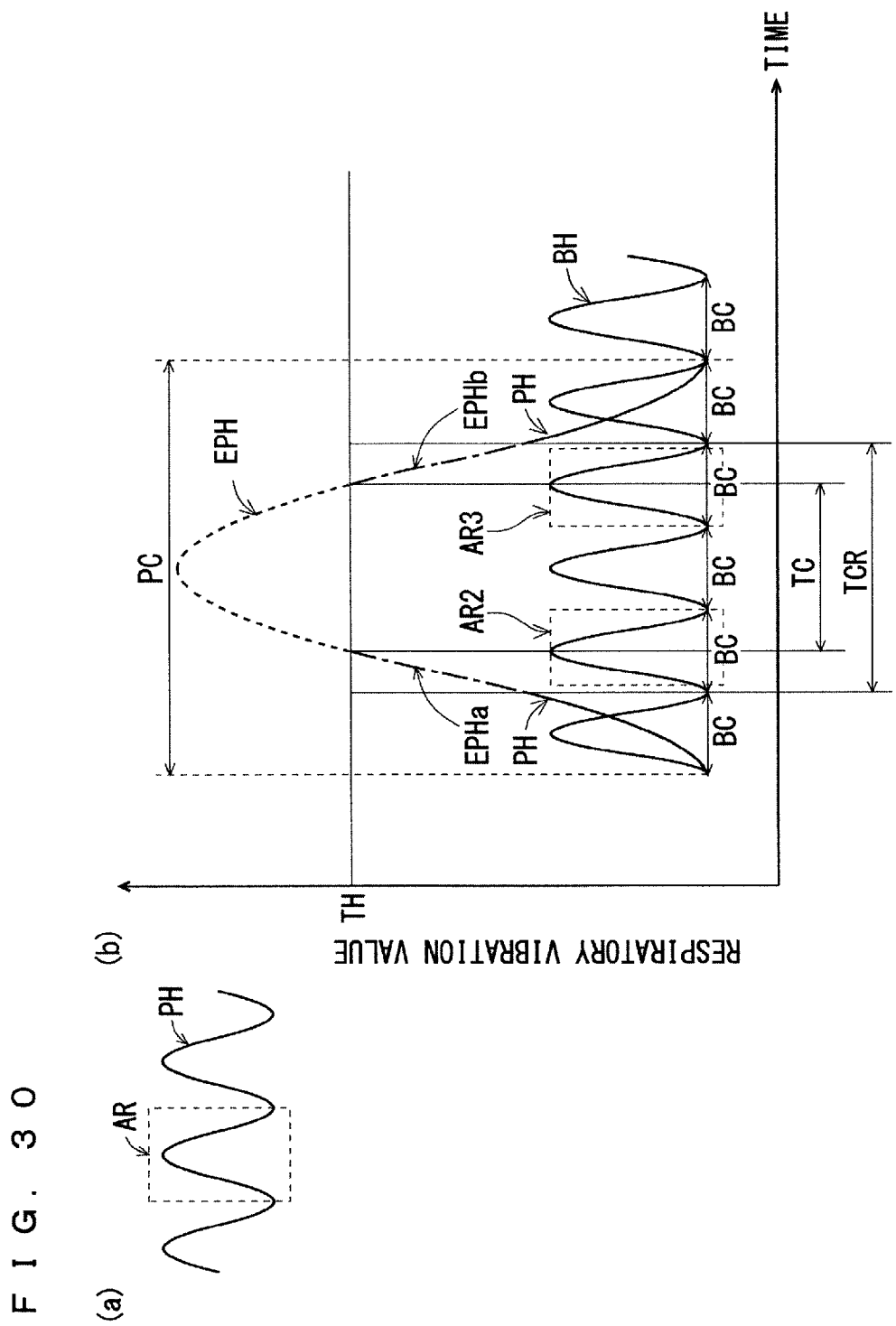
FIG. 30 is a diagram explaining a processing of adjusting a blood-flow-restricted time to be set in units of blood flow cycle.

FIG. 30 is a diagram explaining a processing of adjusting a blood-flow-restricted time TC such that a blood flow analysis is performed in units of blood flow cycle BC detected by the blood flow cycle detecting unit 125. Part (a) of FIG. 30 shows a partial waveform in the respiratory phase PH, and part (b) of FIG. 30 shows the respiratory phase PH in a region AR (for one period) of part (a) of FIG. 30 and a corresponding blood flow phases BH in a superimposed manner. The vertical axis of part (b) of FIG. 30 represents a respiratory vibration value for the respiratory phase PH and a pixel value (blood flow amount) for the blood flow phase BH, and the horizontal axis of part (b) of FIG. 30 represents a time at which a moving image is captured for these phases. Although in practice, the blood flow phases BH have a time interval between a highest value HP to a following highest value HP as shown in FIG. 29, part (b) of FIG. 30 schematically shows blood flow phases BH without time intervals.

Described below are the correspondence between FIG. 30 and FIG. 27 in the case where the configuration of FIG. 27 is employed and the correspondence between FIG. 30 and FIG. 28 in the case where the configuration of FIG. 28 is employed.

In the employment of the image processing apparatus 3D shown in FIG. 27, the blood-flow-restricted time TC13 (see FIG. 10) set in the third blood-flow-restricted time determining processing by the blood-flow-restricted time determining unit 130 corresponds to the blood-flow-restricted time TC shown in FIG. 30.

In the employment of the image processing apparatus 3D2 shown in FIG. 28, meanwhile, the blood-flow-restricted times TC21 to TC24 (see FIG. 14 to FIG. 17) determined by the amplitude-direction extending unit 132 of the blood-flow-restricted time determining unit 130D2 or the blood-flow-restricted times TC31 and TC32 (see FIG. 20 and FIG. 21) determined by the time-axis-direction extending unit 133 correspond to the blood-flow-restricted time TC shown in FIG. 30. The blood-flow-restricted time TC shown in FIG. 30 may be a blood-flow-restricted time TC determined by mutually causing the amplitude-direction extending unit 132 and the time-axis-direction extending unit 133 to function.

In any case, as described above, the blood flow phase BH corresponding to the set blood-flow-restricted time TC is not typically set in units of blood flow cycle BC. When a blood flow analysis is performed in units of blood flow cycle BC, a blood-flow-analysis value is missing in the blood flow cycle BC at the time of the boundary between blood-flow-restricted times TC (that is, regions AR2 and AR3), and accordingly, the blood flow state of the overall blood flow cycle BC cannot be understood.

Therefore, the blood flow cycle unitizing unit 152 adjusts and changes a blood-flow-restricted time TC such that a blood flow analysis is performed on the blood-flow-restricted time TC in units of blood flow cycle BC (see FIG. 29) detected by the blood flow cycle detecting unit 125, thereby determining a blood-flow-restricted time TCR again. In other words, the blood flow cycles BC in the regions AR2 and AR3 (in other words, an inspiration phase EPHa and an expiration phase EPHb in the regions AR2 and AR3) are also included in the blood-flow-restricted time TCR. Thus, analysis data is present in units of blood flow cycle BC at times other than the blood-flow-restricted time TCR, enabling blood flow analysis in units of blood flow cycle BC.

Although the blood flow cycle unitizing unit 152 adjusts the blood-flow-restricted time IC to be extended to the blood-flow-restricted time TCR in the example of FIG. 30, it may adjust the blood-flow-restricted time TC to be reduced. In other words, in the reduction, blood flow analysis can be performed in units of blood flow cycle BC at times other than the blood-flow-restricted time TCR as in the extension. Meanwhile, in the reduction, an amount of data for two blood flow cycles BC can be used in blood flow analysis compared with the case of extension.

<5-3. Basic Operation of Image Processing Apparatus 3D>

Figure 31:
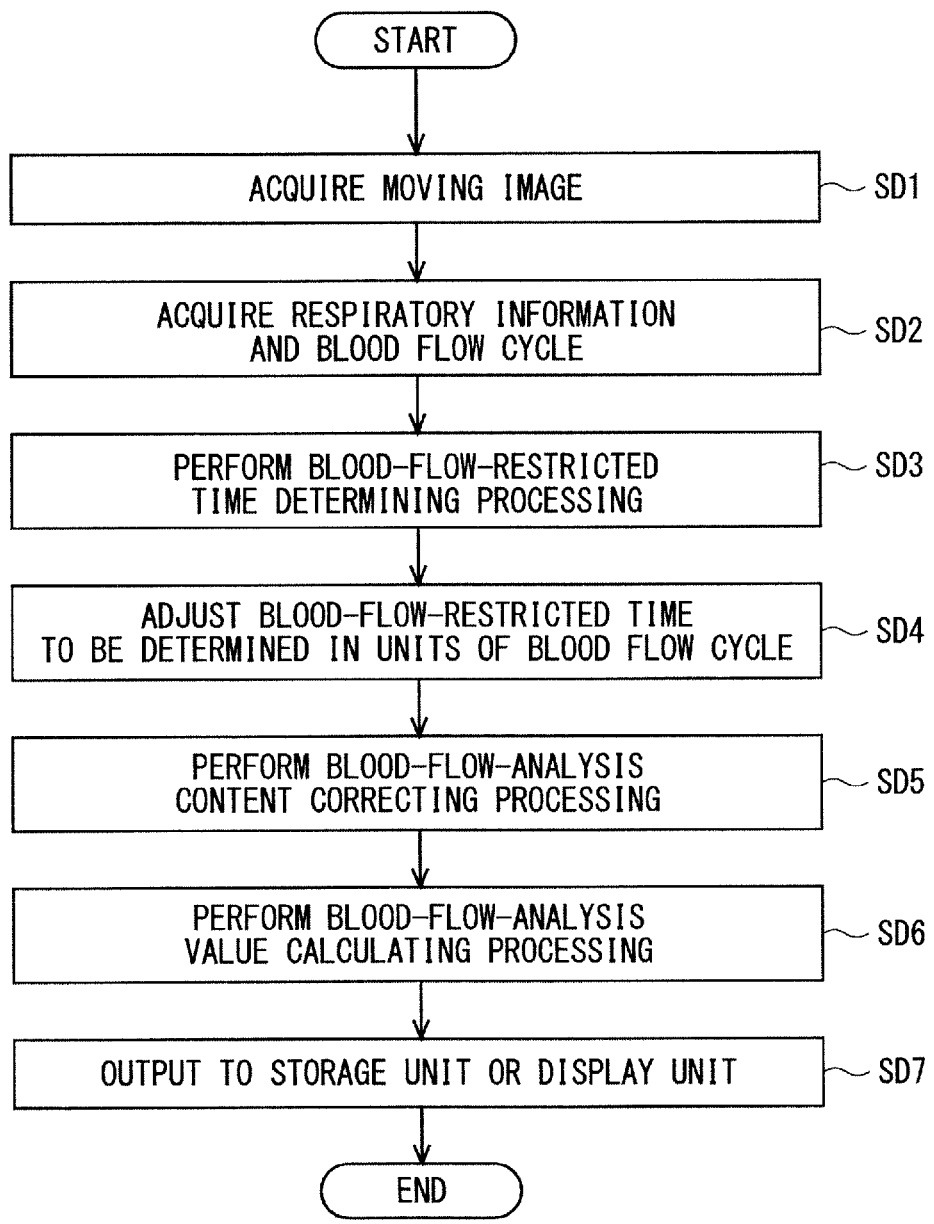
FIG. 31 is a flowchart explaining the basic operation of the image processing apparatus 3D achieved in the fifth embodiment.

FIG. 31 is a diagram illustrating the operational flow of an image processing apparatus 3D according to the fifth embodiment. FIG. 31 shows a representative case where the blood-flow-analysis content correcting processing is the preprocessing (a1) or (a2). Steps SD1, SD3, SD6, and SD7 of FIG. 30 are similar to Steps S1, S3, S5, and S6 of FIG. 11, which will not be described here.

In the fifth embodiment, the blood flow cycle detecting unit 125 and the blood flow cycle unitizing unit 152, which are not provided in the first embodiment, are added, and thus, only the following steps are added or changed.

In other words, through Step SD1 as a step similar to the step of the first embodiment, as shown in FIG. 31, in Step SD2, the respiratory information acquiring unit 120 performs the first or second respiratory information acquiring processing to detect a respiratory phase PH and a respiratory period PC (see FIG. 5 to FIG. 7), and the blood flow cycle detecting unit 125 detects the blood flow cycle BC of a target region using a plurality of frame images MI acquired in Step SD1 (see FIG. 29).

In Step SD4, the blood flow cycle unitizing unit 152 adjusts a blood-flow-restricted time TC such that a blood flow analysis is performed on the blood-flow-restricted time TC determined in the blood-flow-restricted time determining processing of Step SD3 in units of blood flow cycle BC, determining as a blood-flow-restricted time TCR again (see FIG. 30).

In Step SD5, the blood flow analysis correcting unit 151D performs a blood-flow-analysis content correcting processing of excluding a frame image MI from targets for blood flow analysis or decreasing the blood-flow-analysis importance of the frame image MI compared with another time period at the blood-flow-restricted time TCR determined in Step SD4. In other words, the blood-flow-analysis content correcting processing herein refers to a preprocessing to be performed before the blood flow analyzing processing, and the blood flow analysis correcting unit 151D performs any of the processings (a1) and (a2).

The remaining steps are performed as in the first embodiment.

As described above, in the image processing apparatus 3D according to the fifth embodiment, the blood flow analysis correcting unit 151D includes the blood flow cycle unitizing unit 152 that adjusts a blood-flow-restricted time TC such that a blood flow analysis is performed on the blood-flow-restricted time TC determined in the blood-flow-restricted time determining processing in units of blood flow cycle BC. This prevents missing of a blood-flow-analysis value in units of blood flow cycle BC, whereby an overall blood flow state in the blood flow cycle BC can be understood.

6. Modifications

First Embodiment to Fifth Embodiment

While the first embodiment group (the first embodiment to the fifth embodiment) of the present invention has been described above, the present invention is not limited to the first embodiment group and may be modified variously While the image processing apparatuses 3, 3A, 3B, 3C, 3C2, and 3D have been described in the respective embodiments to be performed individually in the first embodiment group, the individual functions thereof may be combined unless they are inconsistent with each other.

The fourth embodiment has described only the case where the blood-flow-restricted time limiting unit 140 limits the third blood-flow-restricted time determining processing (see FIG. 10) in the case of limiting the blood-flow-restricted time determining unit 130C. In another configuration, the blood-flow-restricted time limiting unit 140 may limit the second blood-flow-restricted time determining processing (see FIG. 9). If the configuration in which the blood-flow-restricted time limiting unit 140 limits the second blood-flow-restricted time determining processing of the blood-flow-restricted time determining unit 130C is employed, however, the blood-flow-restricted time limiting unit 140 limits the blood-flow-restricted time determining unit 130C so as to satisfy the condition (e1).

The blood flow cycle unitizing unit 152 (see FIG. 27 and FIG. 28) is provided in the blood flow analysis correcting unit 151D in the fifth embodiment, which is not limited thereto. For example, if a configuration in which the units of blood flow cycle BC, detected by the blood flow cycle detecting unit 125, can be input to the blood-flow-restricted time determining unit 130 is employed, the blood flow cycle unitizing unit 152 may be provided in the blood-flow-restricted time determining unit 130.

The respiratory information and the blood flow cycle BC are acquired simultaneously in Step SD1 (see FIG. 31) in the fifth embodiment, which is not limited thereto. In other words, it suffices that the blood flow cycle BC is acquired before Step SD4 in which the blood flow cycle unitizing unit 152 adjusts the blood-flow-restricted time TC such that a blood flow analysis is performed in units of blood flow cycle BC. Thus, the following configuration may be employed; the blood flow cycle BC is acquired after the respiratory information is acquired, or the respiratory information is acquired after the blood flow cycle BC is acquired.

Figure 32:
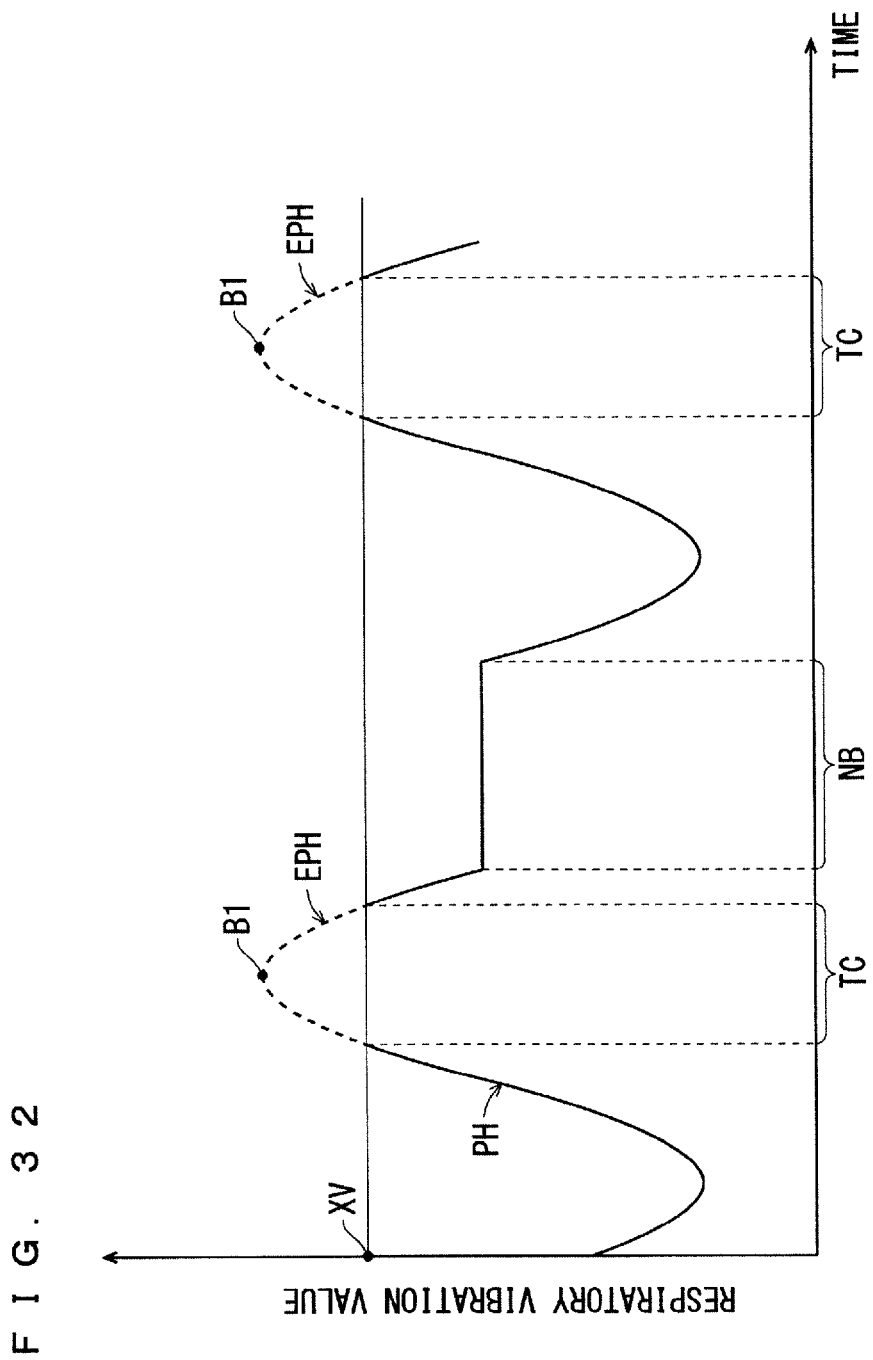
FIG. 32 is a diagram explaining a respiratory phase PH in the case where a moving image is captured during breath holding in respiration.

The blood-flow-restricted time TC in the case where a moving image is captured while breath is being held during respiration can be set with the use of, for example, a threshold of the respiratory vibration value statistically obtained. FIG. 32 is a diagram explaining a respiratory phase PH in the case where a moving image is captured during breath holding in respiration.

As shown in FIG. 32, the respiratory phase PH in the case where a moving image is captured while breath is being held is acquired as a constant respiratory vibration value during a time section NB. The time section NB while breath is being held can be used as analysis data if it does not belong to the maximum inspiration phase B1 or its neighbor. As described above, however, a constant respiratory vibration value appears during the time section NB and the slope of the respiratory phase PH is always zero during the section. As a result, in the second blood-flow-restricted time determining processing (see FIG. 9), the respiratory vibration value may be falsely detected as a local maximum value (maximum inspiration phase B1) or a local minimum value (maximum expiration phase B2). Thus, in the third blood-flow-restricted time determining processing (see FIG. 10), a blood-flow-restricted time TC can be determined with, for example, a statistically obtained respiratory vibration value as a threshold XL, which corresponds to a reference value SV of FIG. 10 (see FIG. 32).

If the test subject M is not a healthy person and has different respiratory phases PH in the left lung field and the right lung field, the respiratory phase PH is desirably detected for each of the left and right lung fields to individually determine blood-flow-restricted times TC.

A blood flow amount can be measured accurately if a respiratory vibration value changes less (the slope of the respiratory phase PH is closer to zero) at the times other than the blood-flow-restricted time TC. Thus, a blood flow analysis is desirably performed near the maximum expiration phase B2.

The subject may be an animal body as well as a human body.

<6-1. Summary of Image Processing Apparatuses Described in First Embodiment Group>

For example, the following first to sixteenth aspects of the image processing apparatuses according to the first embodiment group (the first embodiment to the fifth embodiment) described above are conceivable. The first aspect relates to an image processing apparatus that performs a blood flow analysis, which includes moving image acquiring unit, respiratory information acquiring unit, blood-flow-restricted time determining unit, and blood flow analysis correcting unit. The moving image acquiring unit acquires a moving image including a plurality of frame images sequentially capturing, in a time direction, a state in which a blood flow of a target region inside a body of a human or an animal changes. The respiratory information acquiring unit performs a respiratory information acquiring processing of acquiring respiratory information in the body synchronized at times at which the frame images are captured. The blood-flow-restricted time determining unit performs a blood-flow-restricted time determining processing of determining on the basis of the respiratory information, a blood-flow-restricted time indicating at a time at which the blood flow of the target region is assumed to be restricted due to respiration. The blood flow analysis correcting unit performs a blood-flow-analysis content correcting processing of excluding the frame image captured at the blood-flow-restricted time from targets for blood flow analysis or decreasing the blood-flow-analysis importance of the frame image compared with another time period.

In the second aspect, in the image processing apparatus of the first aspect, the respiratory information acquiring processing includes a processing of acquiring, as the respiratory information, respiratory vibration values indicated as physical change values of a lung field region of the body. The blood-flow-restricted time determining processing includes a processing of determining, as the blood-flow-restricted time, a time at which the respiratory vibration value becomes a maximum value.

In the third aspect, in the image processing apparatus of the first aspect, the respiratory information acquiring processing includes a processing of acquiring, as the respiratory information, respiratory vibration values indicated as physical change values of a lung field region of the body. A respiratory period is recognizable from the respiratory vibration values. The blood-flow-restricted time determining processing includes a processing of determining, per respiratory period, a time at which the respiratory vibration value becomes a maximum value as the blood-flow-restricted time.

In the fourth aspect, in the image processing apparatus of the first aspect, the respiratory information acquiring processing includes a processing of acquiring, as the respiratory information, relative respiration values indicating relative values that enable judgment about to which of an inspiration phase and an expiration phase of the body the respiratory vibration values belong. A is respiratory period is recognizable from the relative respiration values. The blood-flow-restricted time determining processing includes a processing of determining, per respiratory period, a time at which the relative respiration value changes from the inspiration phase to the expiration phase as the blood-flow-restricted time.

In the fifth aspect, in the image processing apparatus of the second to fourth aspects, the blood-flow-restricted time determining unit includes a blood-flow-restricted time extending unit that extends the blood-flow-restricted time to provide a time width relative to the blood-flow-restricted time.

In the sixth aspect, in the image processing apparatus of the second aspect, the blood-flow-restricted time determining unit includes a blood-flow-restricted time extending unit that extends the blood-flow-restricted time to provide a time width relative to the blood-flow-restricted time. The blood-flow-restricted time extending unit includes an amplitude-direction extending unit that performs an amplitude-direction extending processing of setting the time width at a time at which the respiratory vibration value is not less than a first threshold, the first threshold being a value smaller by a first value than a value that is the maximum value of the respiratory vibration values.

In the seventh aspect, in the image processing apparatus of the sixth aspect, the first value includes any one of (b1) a value calculated on the basis of a difference value between the maximum value and a minimum value of the respiratory vibration values, and (b2) a predetermined constant value.

In the eighth aspect, in the image processing apparatus of the third aspect, the blood-flow-restricted time determining unit includes a blood-flow-restricted time extending unit that extends the blood-flow-restricted time to provide a time width relative to the blood-flow-restricted time. The blood-flow-restricted time extending unit includes an amplitude direction extending unit that performs an amplitude-direction extending processing of setting the time width at a time at which the respiratory vibration value is not less than a second threshold, the second threshold being a value smaller by a second value than the maximum value of the respiratory vibration values for each respiratory period.

In the ninth aspect, in the image processing apparatus of the eighth aspect, the second value includes any one of (c1) a value set per respiratory period and calculated on the basis of a difference value between the maximum value and a minimum value of the respiratory vibration values for each respiratory period, and (c2) a predetermined constant value.

In the tenth aspect, in the image processing apparatus of the first aspect, the respiratory information acquiring processing includes a processing of acquiring, as the respiratory information, respiratory vibration values indicated as physical change values of a lung field region of the body. The blood-flow-restricted time determining processing includes a processing of determining, as the blood-flow-restricted time, a time at which the respiratory vibration value is not less than a predetermined reference value.

In the eleventh aspect, in the image processing apparatus of the third or fourth aspect, the blood-flow-restricted time determining unit includes a blood-flow-restricted time extending unit that extends the blood-flow-restricted time to provide a time width relative to the blood-flow-restricted time. The time width includes any one of (d1) a combined time width of a first time width determined on the basis of a time required for the inspiration phase and a second time width determined on the basis of a time required for the expiration phase per respiratory period, (d2) a time width determined, per respiratory period, on the basis of a time required for one period, and (d3) a predetermined time width.

In the twelfth aspect, the image processing apparatus according to any one of the second to eleventh aspects further includes blood-flow-restricted time limiting unit for limiting the blood-flow-restricted time determining processing to satisfy any one of (e1) a condition that a total time of times required for analysis used in the blood flow analysis at times other than the blood-flow-restricted time in an overall time is not less than a first reference time, and (e2) a condition that times required for analysis used in the blood flow analysis at times other than the blood-flow-restricted time per respiratory period is not less than a second reference time.

In the thirteenth aspect, the image processing apparatus according to any one of the first to twelfth aspects further includes blood-flow-cycle detecting unit for detecting a blood flow cycle of the target region, wherein the blood flow analysis correcting unit includes a blood flow cycle unitizing unit that adjusts the blood-flow-restricted time such that a blood flow analysis is performed on the blood-flow-restricted time determined in the blood-flow-restricted time determining processing in units of the blood flow cycle.

In the fourteenth aspect, in the image processing apparatus according to any one of the first to thirteenth aspects, the blood-flow-analysis content correcting processing includes any one of, for analysis data being a target for the blood flow analysis in the moving image, a preprocessing to be performed before a blood flow analyzing processing of obtaining a blood-flow-analysis value is performed, and a postprocessing to be performed after the blood flow analyzing processing is performed. The preprocessing includes, for data at the blood-flow-restricted time of the analysis data, any one of (a1) processing of prohibiting the blood flow analyzing processing, and (a2) a processing of decreasing importance to cause the blood flow analyzing processing to be performed. The postprocessing includes, for data at the blood-flow-restricted time of the blood-flow-analysis value, any one of (a3) a processing of treating the data not as the blood-flow-analysis value, and (a4) a processing of decreasing the blood-flow-analysis importance of the data.

In the fifteenth aspect, in the image processing apparatus according to any one of the first to fourteenth aspects, the target region includes a blood vessel region in the lung field region.

The sixteenth aspect relates to a computer-readable non-transitory storage medium storing a program, which is executed by a computer included in an image processing apparatus according to any one of the first to fifteenth aspects.

According to the image processing apparatus of the first aspect, the blood-flow-restricted time determining unit determines a blood-flow-restricted time on the basis of respiratory information, and the blood flow analysis correcting unit performs the blood-flow-analysis content correcting processing of eliminating a frame image captured at the blood-flow-restricted time from targets for blood flow analysis or decreasing the blood-flow-analysis importance of the frame image compared with another time period. Thus, blood flow analysis involving the blood-flow-analysis content correcting processing is enabled, preventing a blood-flow-analysis value from becoming an abnormal value due to respiration, which achieves a highly accurate, appropriate blood flow analysis value. This prevents a decrease in the performance of finding a blood clot, enabling appropriate, efficient dynamic diagnosis of a blood flow.

According to the image processing apparatus of the second aspect, the blood-flow-restricted time determining processing includes the processing of determining, as the blood-flow-restricted time, a time at which the respiratory vibration value becomes a maximum value. This allows the time, at which it is assumed that a blood flow is restricted most and a blood-flow-analysis value is most adversely affected, to be determined as a blood-flow-restricted time.

According to the image processing apparatus of the third aspect, a time at which the respiratory vibration value becomes a maximum value is determined as a blood-flow-restricted time per respiratory period. The maximum value is obtained per respiratory period, allowing a time, at which it is assumed that a blood-flow-analysis value is adversely affected, to be determined as a blood-flow-restricted time on the basis of a physical change value of the lung field region.

According to the image processing apparatus of the fourth aspect, the blood-flow-restricted time determining processing includes the processing of determining a time at which a relative respiration value changes from the inspiration phase to the expiration phase as the blood-flow-restricted time per respiratory period. This allows the time, at which it is assumed that a blood flow is restricted most and that a blood flow analysis value is most adversely affected, to be determined as a blood-flow-restricted time in each respiratory period, achieving the robustness effect where there is no influence of another period. Recognizing the respiratory period from the relative respiration values eliminates the need for acquiring a respiratory period on the basis of a moving image, correspondingly simplifying the respiratory information acquiring processing.

According to the image processing apparatus of the fifth aspect, the blood-flow-restricted time determining unit includes the blood-flow-restricted time extending unit that extends a blood-flow-restricted time to provide a time width relative to the blood-flow-restricted time. This extends a time period when it is assumed that a blood flow is restricted and that a blood-flow-analysis value is adversely affected.

According to the image processing apparatus of the sixth aspect, a time width is generated at a time at which the respiratory vibration value is not less than the first threshold. Thus, the time period in which a blood flow is highly likely to be restricted can be extended and extracted more reliably, thereby being determined as a blood-flow-restricted time.

According to the image processing apparatus of the seventh aspect, in the case where a value based on a difference value between the maximum value and the minimum value of the respiratory vibration values is used as a first value, the first value can be determined by a maximum respiratory amplitude value in the respiratory phase. Thus, the first threshold can be appropriately set without being too low. In the case where a predetermined constant value is used as the first value, the first threshold can be set easily without specifically calculating a maximum respiratory amplitude value in the respiratory phase.

According to the image processing apparatus of the eighth aspect, a time width is set using a maximum respiratory vibration value per respiratory period. Thus, the time, at which a blood flow is highly likely to be restricted in the respiratory period, can be appropriately extracted and then be determined as a blood-flow-restricted time. The amplitude-direction extending processing is performed per respiratory period, achieving the robustness effect where there is no influence of another period.

According to the image processing apparatus of the ninth aspect, in the case where a value calculated on the basis of a difference value between a maximum respiratory vibration value and a minimum respiratory vibration value per respiratory period is used as a second value, the second value can be determined by a respiratory amplitude value. Thus, the second threshold can be appropriately set without being too low. In the case where a predetermined constant value is used as the second value, the second threshold can be set easily without specifically calculating respiratory amplitude values.

According to the image processing apparatus of the tenth aspect, the blood-flow-restricted time determining processing includes the processing of determining, as the blood-flow-restricted time, a time at which the respiratory vibration value is not less than a predetermined reference value. Thus, the blood-flow-restricted time can be extended and determined easily without determining a maximum value per respiratory period.

Further, setting a reference value using the statistical data obtained as knowledge enables a blood-flow-restricted time to be determined stably, independently of the data obtained from a moving image.

Further, providing a reference value enables accurate comparison of differences in blood-flow-analysis value for pieces of data on a moving image in the same body before and after the photographing period. Thus, the state of a blood flow in one body can be monitored accurately over time from dynamic diagnosis.

According to the image processing apparatus of the eleventh aspect, the time width includes any one of the time widths (d1) to (d3). Thus, in the setting of a time width on the basis of a time required for each phase, the time width to be set can be prevented from becoming relatively too large compared with the time required for each phase, and a blood-flow-restricted time can be appropriately extended and determined. If the time required for the inspiration phase differs from the time required for the expiration phase, a time width can be set appropriately by combination of the first and second time widths according to the inspiration phase and the expiration phase. This allows a blood-flow-restricted time to be appropriately determined also for patients who have difficulty in respiration in which the time required for the inspiration phase differs from the time required for the expiration phase.

In the setting of a time width on the basis of a time required for one period, it suffices to calculate only the time required for one period without individually calculating the time required for the inspiration phase and the time required for the expiration phase, reducing a calculation time.

In the use of a predetermined time width, a blood-flow-restricted time can be easily extended and determined, independently of a respiratory vibration value at each time (that is, without calculating a time of the respiratory phase).

According to the image processing apparatus of the twelfth aspect, blood-flow-restricted time limiting for limiting the blood-flow-restricted time determining processing is further provided. Thus, a minimum amount of data in the time required for blood flow analysis can be allocated, enabling appropriate dynamic diagnosis of a blood flow.

According to the image processing apparatus of the thirteenth aspect, the blood-flow-analysis value controlling unit includes a blood flow cycle unitizing unit that adjusts a blood-flow-restricted time such that a blood flow analysis is performed on the blood-flow-restricted time determined in the blood-flow-restricted time determining processing in units of blood flow cycle. This prevents missing of a blood-flow-analysis value per blood flow cycle, whereby an overall blood flow state in the blood flow cycle can be understood.

According to the image processing apparatus of the fourteenth aspect, the blood-flow-analysis content correcting processing includes any one of the processings (a1)) to (a4). In other words, in the processing (a1) or (a2), the processing of prohibiting the blood flow analyzing processing or reducing effects of the blood flow analyzing processing is performed before the blood flow analyzing processing is performed, enabling efficient blood flow analysis in consideration of a blood-flow-restricted time. In particular, the processing (a1)) does not require the blood flow analyzing processing at a blood-flow-restricted time, reducing a calculation time without unnecessary calculations.

In the processing (a3) or (a4), the processing of treating the data at the blood-flow-restricted time, which has been subjected to the blood flow analysis, not as a blood-flow-analysis value or the processing of decreasing its importance. This eliminates the need for determining a blood-flow-restricted time before the blood flow analyzing processing, allowing the blood-flow-restricted time to be determined after the blood flow analyzing processing is performed.

According to the fifteenth aspect, the target region is a blood vessel region in the lung field region, allowing the state of a blood flow in the lung field region to be understood appropriately by dynamic diagnosis. This prevents a decrease in the performance of finding pulmonary thromboembolism by dynamic diagnosis.

According to the sixteenth aspect, effects similar to those of the first to fifteenth aspects can be achieved.

7. Sixth Embodiment

A radiographic dynamic image capturing system according to a sixth embodiment of the present invention will now be described.

<7-1. Overall Configuration of Radiographic Dynamic Image Photographing System>

The radiographic dynamic image capturing system according to the sixth embodiment captures a radiographic image of a human body or an animal body as a subject in the state in which the physical state of the target region of the subject changes periodically over time.

Figure 35:
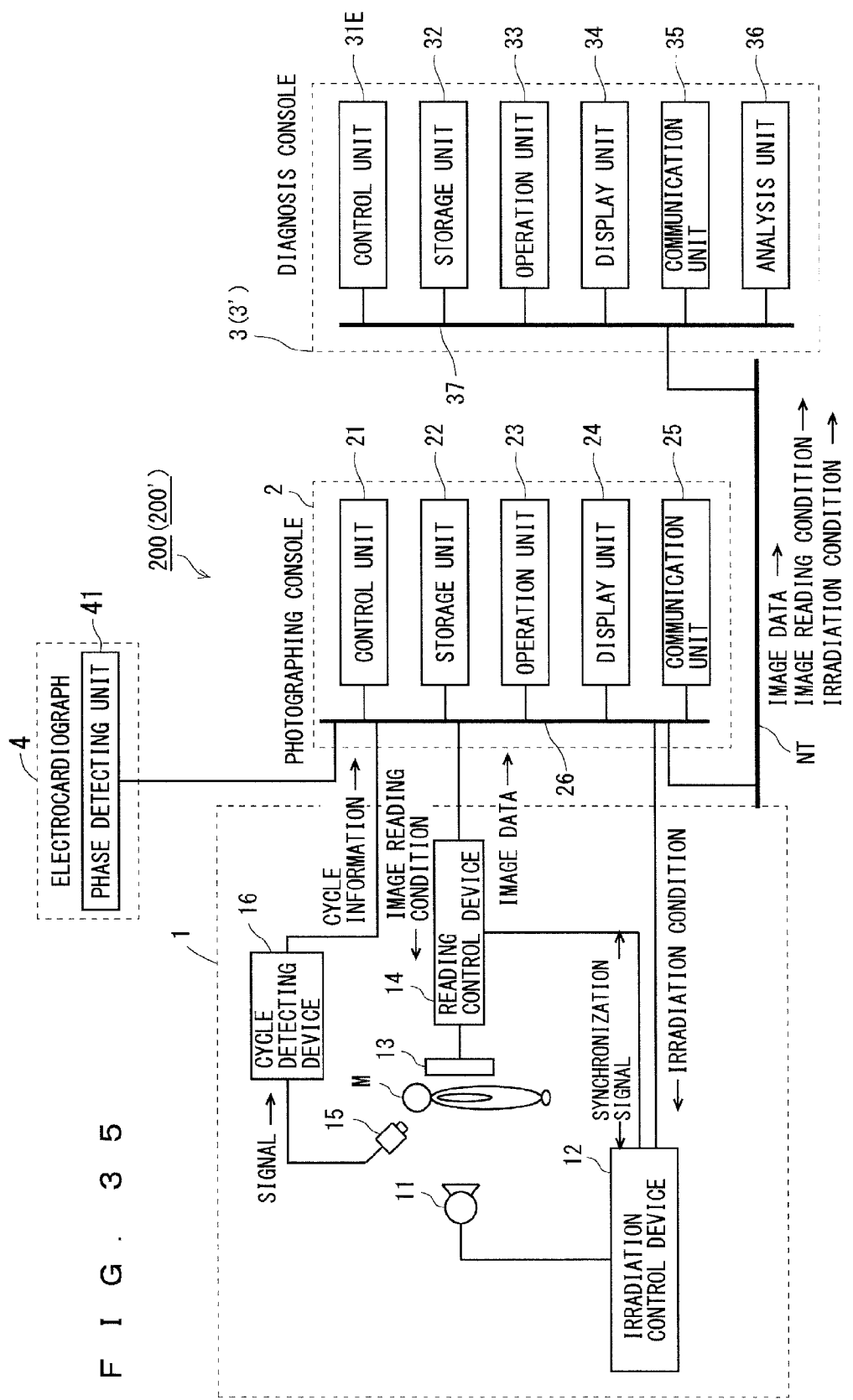
FIG. 35 is a diagram showing the overall configuration of a radiographic dynamic image capturing system 200 according to a sixth embodiment.

FIG. 35 is a diagram showing the overall configuration of the radiographic dynamic image capturing system according to the sixth embodiment. As shown in FIG. 35, a radiographic dynamic image capturing system 200 includes a photographing apparatus 1, a photographing control apparatus 2 (photographing console), an image processing apparatus 3 (diagnosis console), and an electrocardiograph 4. The photographing apparatus 1 and the electrocardiograph 4 are connected with the photographing control apparatus 2 by communication cables or the like, and the photographing control apparatus 2 is connected with the image processing apparatus 3 through a communication network NT such as LAN. The apparatuses constituting the radiographic dynamic image capturing system 200 comply with the digital image and communications in medicine (DICOM) standard, and communicate with each other in accordance with the DICOM standard.

<7-1-1. Configuration of Photographing Apparatus 1 and Other Apparatuses>

The photographing apparatus 1, the photographing control apparatus 2, and the image processing apparatus 3 have the same configurations as those of the photographing apparatus 1, the photographing control apparatus 2, and the image processing apparatus 3 of the first embodiment shown in FIG. 1, which will be denoted by the same references and their description will be omitted as appropriate.

<7-1-2. Configuration of Electrocardiograph 4>

Although FIG. 35 shows the electrocardiograph 4 located far from the subject M, in practice, the electrode terminals of the electrocardiograph 4 are individually attached to the test subject M and output an electrocardiogram waveform of the test subject M as a digital signal. As shown in FIG. 35, the electrocardiograph 4 includes a phase detecting unit 41. The phase detecting unit 41 detects the phase of a heartbeat of the subject M, in response to a control signal from the CPU of the control unit 21, as basic information for synchronizing a photographing operation of the photographing apparatus 1.

The configuration of the electrocardiograph 4 is not necessarily required in this embodiment and is not required when a first cardiac period acquiring processing of FIG. 38, described below, is employed.

<7-2. General Characteristics of Respiratory Phase and Problem with Blood-Flow-Analysis Value>

The general characteristics of a respiratory phase and the problem with a blood-flow-analysis value obtained through blood flow analysis will be described as the premise of the detailed description of the image processing apparatus 3 in this embodiment.

Figure 36:
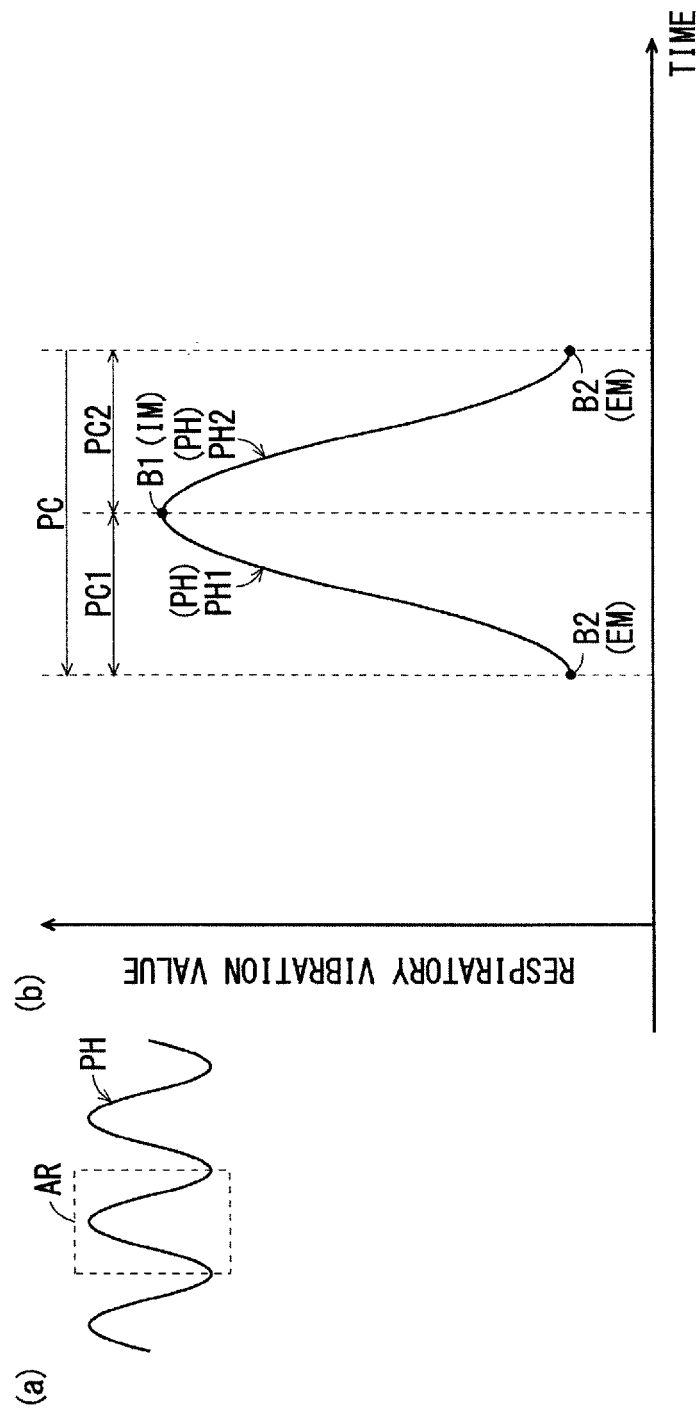
FIG. 36 is a diagram explaining respiratory phases.

Described here is the relations in the respiratory phase state and the cardiac phase state, which is important in blood flow analysis. FIG. 36 is a view illustrating general characteristics of the respiratory phase, where part (a) of FIG. 36 shows a partial waveform of a respiratory phase PH, and part (b) of FIG. 36 shows the respiratory phase PH in a region AR (for one period) of part (a) of FIG. 36. FIG. 37 is a view illustrating the relationship between the respiratory phase PH and the cardiac phase BH. In FIG. 36 and FIG. 37, the horizontal axis represents a time at which a moving image is captured (in the time direction), and the vertical axis represents a respiratory vibration value (described below in detail).

As shown in part (b) of FIG. 36, the respiratory phase PH for one period PC has a maximum inspiration phase IM corresponding to a maximum value B1 in the respiratory period PC and a maximum expiration phase EM corresponding to a minimum value B2 (described below in detail). The section of the respiratory phase PH from the maximum expiration phase EM to the maximum inspiration phase IM is referred to as an inspiration phase PH1, and the section of the respiratory phase PH from the maximum inspiration phase IM to the maximum expiration phase EM is referred to as an expiration phase PH2. Hereinafter, a first half period PC1 and a second half period PC2 of one period PC starting from the maximum expiration phase EM are referred to as an inspiration phase PH1 and an expiration phase PH2, respectively.

As shown in FIG. 37, a cardiac phase BH1 of a region AR1, corresponding to the maximum inspiration phase IM, and a cardiac phase BH2 of a region AR2, corresponding to the maximum expiration phase EM, have smaller pulsations than the cardiac phases BH in the regions other than the regions AR1 and AR2.

Among the major causes of the smaller pulsations, as shown in FIG. 37, are the following three.

First, in the maximum inspiration phase IM, a phenomenon in which a blood flow through the blood vessels in the lung field region is restricted (a blood flow is attenuated) occurs. This decreases the accuracy of blood flow analysis. As described above, two types of factors are considered to attenuate a blood flow: (i) blood vessel compression and (ii) blood vessel expansion.

Third, (iii) the following phenomenon occurs, in which the thickness of a blood vessel varies due to a different pressure on the blood vessel between in the maximum inspiration phase IM and the maximum expiration phase EM. This decreases the accuracy of blood flow analysis. Specifically, the following phenomenon occurs, in which a pressure on a blood vessel varies between in the inspiration phase PH1 and in the expiration phase PH2 because the lung is stretched vertically in the inspiration phase PH1 and, meanwhile, is contracted vertically in the expiration phase PH. This phenomenon may cause the thickness of the blood vessel and the relative positional relationship of the blood vessel in the lung field to greatly differ between in the inspiration phase PH1 and in the expiration phase PH2. Thus, if an analysis using all blood flows in the resting respiration state and the forced respiration state is merely performed, blood-flow-analysis values are adversely affected due to different pressures on the blood vessel in the inspiration phase PH1 state and in the expiration phase PH2 state.

To solve the problems (i) and (ii), for example, a maximum value acquired from a plurality of difference images acquired from a difference between frame images is used as a pixel value and then the analysis result is output, as described in Japanese Patent Application Laid-Open No. 2004-312434, thereby avoiding the maximum inspiration phase IM and the maximum expiration phase EM. The traditional technology, however, cannot prevent a decrease in the accuracy of a blood flow analysis associated with each of the phase states: the inspiration phase PH1 state and the expiration phase PH2 state.

Against this background, to prevent a false diagnosis due to a decrease in the accuracy of blood flow analysis associated with each of the inspiration phase PH1 state and the expiration phase PH2 state, an appropriate blood-flow-analysis value, which corresponds to each of the inspiration phase PH1 state and the expiration phase PH2, is desired to be obtained.

In each configuration described below, a blood flow analysis is performed in consideration of each of the inspiration phase PH1 and the expiration phase PH2 to prevent a decrease in the accuracy of blood flow analysis associated with each of the phase states, acquiring an appropriate blood-flow-analysis value.

The image processing apparatus 3 in the sixth embodiment will be described below in detail.

<7-3. Specific Configuration of Image Processing Apparatus 3>

The image processing apparatus 3 of the radiographic dynamic image capturing system 200 in the sixth embodiment of the present invention can obtain blood-flow-analysis values in consideration of each of the inspiration phase PH1 state and the expiration phase PH2 state to appropriately and efficiently diagnose an image of a blood flow.

The functional configuration achieved by the image processing apparatus 3 will be described below.

<7-3-1. Functional Configuration of Image Processing Apparatus 3>

Figure 39:
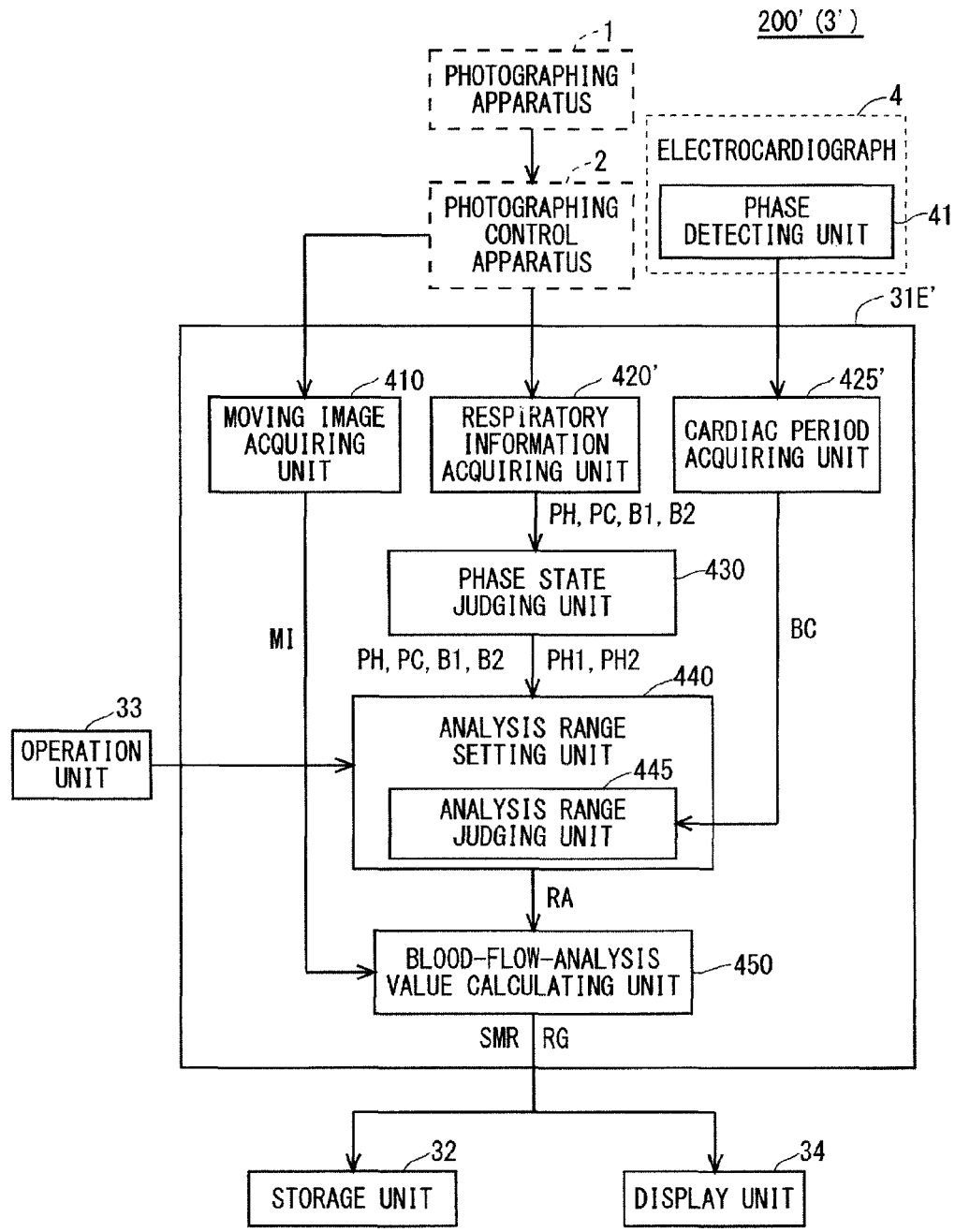
FIG. 39 is a block diagram showing the functional configuration of an image processing apparatus 3' according to the sixth embodiment.

FIG. 38, FIG. 39 is a diagram showing, together with other configurations, the functional configuration achieved by control unit 31E, 31E' through an operation of the CPU or the like in accordance with various programs in the image processing apparatus 3, 3' of the radiographic dynamic image capturing system 200, 200'. The functional configurations are achieved by the CPU or the like operating in accordance with various programs in the image processing apparatus 3, 3' of the radiographic dynamic image capturing system 200, 200'. The image processing apparatus 3, 3' in this embodiment uses a dynamic image capturing the chest mainly including the heart and the both lungs.

The control unit 31E, 31E' is mainly composed of a moving image acquiring unit 410, a respiratory information acquiring unit 420, 420', a cardiac period acquiring unit 425, 425', a phase state judging unit 430, an analysis range setting unit 440, and a blood-flow-analysis value calculating unit 450.

Although the following description will be given on the assumption that the functional configuration of the control unit 31E, 31E' as shown in FIG. 38, FIG. 39 is achieved through execution of a preinstalled program, the functional configuration may be achieved by a dedicated hardware configuration.

The processings performed by the moving image acquiring unit 410, the respiratory information acquiring unit 420, 420', the cardiac period acquiring unit 425, 425', the phase state judging unit 430, the analysis range setting unit 440, and the blood-flow-analysis value calculating unit 450 will be described below in order with reference to FIG. 38 and FIG. 39.

<7-3-1-1. Moving Image Acquiring Unit 410>

The moving image acquiring unit 410 acquires a moving image composed of a plurality of frame images captured by the reading control device 14 of the photographing apparatus 1, in which how a blood flow of the target region in the body of the test subject M changes is captured sequentially in the time direction. The target region in this embodiment is a region being a target for blood flow analysis, an assumed example of which is a blood vessel region in the lung field region. In other words, as shown in FIG. 38 and FIG. 39, the photographing control apparatus 2 is located between the photographing apparatus 1 and the image processing apparatus 3, and detection data (a plurality of frame images) stored in the storage unit 22 of the photographing control apparatus 2 is output to the communication unit 35 of the image processing apparatus 3 through the communication unit 25.

As shown in FIG. 4 used in the first embodiment, the frame images M1 to M10 (MI) acquired by the moving image acquiring unit 410 are images in which one period of the respiratory cycle is captured sequentially at constant photographing timings, similar to the moving image acquiring unit 110 of the first embodiment. Specifically, images captured at photographing timings at the time t=t1, t2, t3, . . . , and t10 correspond to the frame images M1, M2, M3, . . . , and M10, respectively.

<7-3-1-2. Respiratory Information Acquiring Unit 420, 420'>

The respiratory information acquiring unit 420, 420' performs the respiratory information acquiring processing of acquiring respiratory information of the test subject M, which is synchronized at the time at which the frame image MI is captured. Specifically, the respiratory information acquiring processing involves a processing of setting respiratory vibration values indicated as physical change values of the lung field region as respiratory information, thereby performing the processing of acquiring respiratory vibration values for at least one respiratory period PC. Additionally, the respiratory information acquiring processing involves the processing of calculating the maximum value B1 and the minimum value B2 of the respiratory vibration values in the respiratory period PC (see FIG. 36 and FIG. 37).

The method of detecting respiratory vibration values of the respiratory information acquiring processing (first step) is broadly classified into two types of processings, which will now be described separately. Then, the method of calculating the maximum value B1 and the minimum value B2 of the respiratory vibration values in the respiratory period PC and the respiratory period PC (second step) will be described.

<7-3-1-2-1. First Respiratory Information Acquiring Processing: Image Analysis (FIG. 38)>

The first step of the first respiratory information acquiring processing is the processing of calculating respiratory vibration values on the basis of a plurality of frame images MI constituting a moving image acquired by the moving image acquiring unit 410 (see FIG. 38).

As shown in FIG. 38, first, in the first respiratory information acquiring processing, the respiratory information acquiring unit 420 calculates respiratory vibration values using a plurality of frame images MI acquired by the moving image acquiring unit 410. Specifically, the respiratory vibration value is an indicator for measuring a change in the size of the lung field region due to respiration. Examples of such a respiratory vibration value include "the distance between feature points of the lung field region (such as the distance between the apical portion of the lung and the diaphragm," "the area value of the lung field portion (the size of the lung field region)," "the absolute position of the diaphragm," and "the pixel density value of the lung field region." Description will be given of the example cases in which the respiratory vibration value is "the area value of the lung field portion" and "the distance between feature points of the lung field region."

In the case where the respiratory vibration value is "the area value of the lung field portion," the contour of the lung field portion can be extracted to define the number of pixels in the region surround by the contour as the area of the lung field portion.

As shown in FIG. 5 used in the first embodiment, the lung field portion may be extracted for each of the left and right or may be extracted as the contour including the regions of the heart and the spine (see part (b) of FIG. 5).

As described above, the respiratory information acquiring unit 420 extracts the contour OL of the lung field portion using a plurality of frame images MI acquired and detects the number of pixels in the extracted region as an area value of the lung field portion, thereby acquiring respiratory vibration values (see FIG. 38).

In the case where the respiratory vibration value is "the distance between feature points of the lung field region," the distance between the feature points of the lung field region is calculated using a plurality of frame images MI. In other words, the lung field portion is extracted as in the method described above, and two feature points are determined from the extracted region. Then, the distance between the two points is obtained, thereby detecting the distance as a respiratory vibration value. Then, a change in the distance between the feature points (respiratory vibration value) is regarded as a respiratory phase PH.

In the case where a change in the length (lung field length) from the upper end LT to the lower end LB of the lung region is calculated, part (a) of FIG. 6 used in the first embodiment shows an example in which extraction is performed with the apical portion of the lung being the upper end LT of the lung region and with the intersection between the diaphragm and the straight line extending downward from the apical portion of the lung in the body axis direction being the lower end LB of the lung region, and art (b) of FIG. 6 shows an example in which extraction is performed with the apical portion of the lung being the upper end LT of the lung region and with the costophrenic angle being the lower end LB of the lung region.

As described above, the respiratory information acquiring unit 420 extracts the contour OL of the lung field region using a plurality of frame images MI acquired and detects the distance between feature points from the extracted region, thereby acquiring respiratory vibration values (see FIG. 38).

FIG. 40 is a schematic diagram of the respiratory phase PH showing waveform data of the respiratory vibration values detected by the respiratory information acquiring unit 420 in time sequence, which shows the results obtained by calculating respiratory vibration values, such as the area value of the lung field region and the distance between the feature points, and monitoring the respiratory vibration values in the time direction at every photographing timing TM. The vertical arrow shown in FIG. 40 indicates the amplitude direction AP of the respiratory phase PH.

<7-3-1-2-2. Second Respiratory Information Acquiring Processing: Separate Equipment (FIG. 39)>

The first step of the second respiratory information acquiring processing is a processing of measuring a respiratory vibration value by separate equipment, namely, external equipment (see FIG. 39). For example, there may be used a monitoring technique by the device as described in Japanese Patent No. 3793102 or the monitoring technique using the laser light and the sensor composed of a CCD camera.

In this embodiment, the cycle detecting sensor 15 of the cycle detecting device 16 can be used as shown in FIG. 35. Examples of the method of detecting respiratory vibration values from external equipment include the method of detecting the movement of the chest of the subject using a respiration monitoring belt and the method of detecting an air flow of respiration by an air flow meter. These methods are applicable.

As described above, the respiratory information acquiring unit 420' acquires a plurality of frame images MI through the moving image acquiring unit 410 and also acquires respiratory vibration values synchronized with the plurality of frame images MI from external equipment (see FIG. 39). Then, the respiratory vibration values are acquired as time series data as in FIG. 40.

<7-3-1-2-3. Method of Detecting Respiratory Period PC, Maximum Value B1, and Minimum Value B2>

As the second steps of the first and the second respiratory information acquiring processings, the following processing is performed; changes in the respiratory vibration value detected in the first step are regarded as the respiratory phase PH, and the respiratory period PC and the maximum value B1 and the minimum value B2 of the respiratory vibration values in the respiratory period PC are calculated (see FIG. 40).

As shown in FIG. 40, one respiratory period (respiratory cycle) PC is composed of inspiration and expiration, namely, one expiration and one inspiration. In inspiration, the region of the lung field in the rib cage becomes larger as the diaphragm descends and breath is inhaled. The time of inhaling to the maximum extent (a switching point from inspiration to expiration) is the maximum inspiration phase IM. In expiration, the region of the lung field becomes smaller as the diaphragm ascends and breath is exhaled. The time of exhaling to the maximum extent (a switching point from expiration to inspiration) is the maximum expiration phase EM.

Two methods will be described below as the second steps of the first and second respiratory information acquiring processings.

In the first method, times at which the respiratory vibration values reach a local maximum value and a local minimum value are calculated sequentially in the overall time to determine a respiratory period PC, thereby determining a maximum value B1 and a minimum value B2 of the respiratory vibration values in the respiratory period PC. Specifically, the respiratory vibration values in the overall time are smoothed to reduce high-frequency noise components, and then, a local maximum value (maximum inspiration phase IM) and a local minimum value (maximum expiration phase EM) of the respiratory vibration values are calculated. This prevents the noise components contained in the respiratory vibration value from being falsely detected as a local maximum value or a local minimum value.

In the second method, a respiratory period PC is first detected, and then, times at which the respiratory vibration values reach a maximum value and a minimum value are detected per respiratory period PC. The second method differs from the first method in that a maximum value (namely, maximum inspiration phase IM) and a minimum value (maximum expiration phase EM) are calculated not in the overall time but per respiratory period PC. As in the first method, respiratory vibration values may be smoothed to reduce high-frequency noise components, and then, a maximum value and a minimum value may be extracted in the second method.

As described above, the respiratory information acquiring unit 420, 420' regards changes in respiratory vibration value as a respiratory phase PH, thereby detecting the respiratory period PC and a maximum value B1 and a minimum value B2 of the respiratory vibration values in the respiratory period PC (see FIG. 40).

<7-3-1-3. Cardiac Period Acquiring Unit 425, 425'>

The cardiac period acquiring unit 425, 425' performs a cardiac period acquiring processing of acquiring a cardiac period in the body synchronized at a photographing time (see FIG. 38 and FIG. 39).

The cardiac period acquiring processing is broadly classified into two types of processings, which will now be described separately.

<7-3-1-3-1. First Cardiac Period Acquiring Processing: Image Analysis (FIG. 38)>

In the first cardiac period acquiring processing, as shown in FIG. 38, the cardiac period acquiring unit 425 calculates the movement amount of the cardiac wall using a captured image acquired by the moving image acquiring unit 410, thereby acquiring a cardiac period. Specifically, a change of the cardiac wall is detected from a moving image, so that the phase of pulsation of the heart at the timing at which each frame image is captured can be detected. Then, a cardiac period is determined from the phase of the pulsation of the heart.

FIG. 41 is a schematic diagram illustrating changes of the cardiac wall captured in a moving image. As illustrated in FIG. 41, a change of the width of the heart is used as an example of the change of a cardiac wall HL. Part (a) of FIG. 41 to part (c) of FIG. 41 illustrate how the width of the heart increases from w1 to w3 during the expansion of the heart.

The cardiac period acquiring unit 430 detects the width of the heart from each frame image to detect a cardiac period. In one specific example of the technique of detecting the width of the heart, detection is performed by detecting the contour of the heart. Various known techniques can be used as the technique of detecting the contour of the heart. For example, a technique of detecting the contour of the heart by matching, using a model showing the shape of the heart (heart model), feature points in an X-ray image with feature points in the heart model (for example, see "Image feature analysis and computer-aided diagnosis in digital radiography: Automated analysis of sizes of heart and lung in chest images", Nobuyuki Nakamori et al., Medical Physics, Volume 17, Issue 3, May, 1990, pp. 342-350) can be used.

Figure 42:
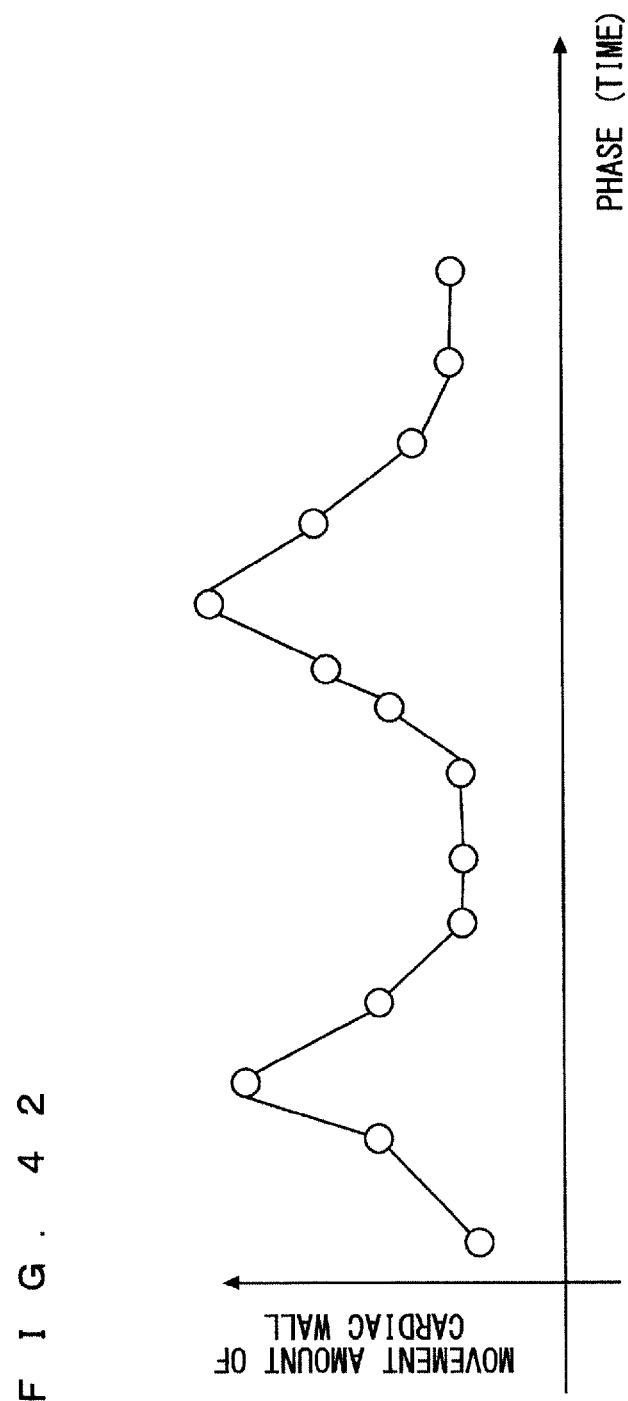
FIG. 42 is a schematic diagram illustrating a change cycle of the width of the heart.

FIG. 42 is a schematic diagram illustrating the relationship between a photographing time and the width of the heart for a plurality of frame images constituting a moving image. In FIG. 42, the horizontal axis represents a time, the vertical axis represents the width of the heart, and a circle represents a value of the detected width of the heart.

Letting the width of the heart obtained at a time t be Hwt and the width of the heart obtained at a time t+1 be Hwt+1, if (Hwt+1−Hwt)≥0 is satisfied, the frame image captured at the time t is categorized as an image in the expansion of the heart. If (Hwt+1−Hwt)<0 is satisfied, the frame image captured at the time t is classified as an image in the contraction of the heart.

As described above, detecting a change of the width of the heart, namely, the cardiac wall HL, allows classification into the expansion and contraction of the heart, enabling the detection of a phase of pulsation of the heart.

As described above, the cardiac period acquiring unit 425 detects a cardiac period on the basis of the movement of the cardiac wall captured in a moving image, thereby automatically acquiring a cardiac period.

<7-3-1-3-2. Second Cardiac Period Acquiring Processing: Electrocardiograph (FIG. 39)>

In the second cardiac period acquiring processing, as shown in FIG. 39, the cardiac period acquiring unit 425' acquires a cardiac period using the result acquired from the phase detecting unit 41 of the electrocardiograph 4. FIG. 43 is a diagram illustrating one period HBC of the electrocardiograph waveform of the test subject M. In FIG. 43, the horizontal and vertical axes represent a time and the magnitude of an electrical signal (voltage), respectively, and a curve indicating a change of the electrical signal including curves Pp, Qp, Rp, Sp, Tp, and Up respectively showing shapes of so-called P, Q, R, S, T, and U waves is shown.

The cardiac period acquiring unit 425 acquires a cardiac period HBC by detecting the points (Pp, Qp, Rp, Sp, Tp, and Up) on the basis of the detection result of the cardiac phase BH acquired from the phase detecting unit 41.

The detecting operation by the phase detecting unit 41 is performed in synchronization with the photographing operation by the photographing apparatus 1 (see FIG. 35).

As described above, the cardiac period acquiring unit 425' acquires a cardiac period HBC from the outside, thereby automatically acquiring a periodic temporal change of the heart.

<7-3-1-4. Phase State Judging Unit 430>

The phase state judging unit 430 performs a phase state judging processing of judging to which of the inspiration phase PH1 state and the expiration phase PH2 state the respiratory information acquired by the respiratory information acquiring unit 420 belongs and obtains the phase state judgment result. The "phase state judgment result" herein refers to the result of any of the inspiration phase PH1 state and the expiration phase PH2 state.

Specifically, the phase state judging processing refers to a processing of judging to which of the inspiration phase PH1 state and the expiration phase PH2 state a respiratory vibration value belongs, on the basis of the maximum value B1 and the minimum value B2 of the respiratory vibration values in the respiratory period PC calculated by the respiratory information acquiring unit 420.

In other words, in the phase state judging processing, as shown in FIG. 36 and FIG. 40, the maximum value B1 and the minimum value B2 of the respiratory vibration values in the respiratory period PC, calculated by the respiratory information acquiring unit 420, are regarded as the maximum inspiration phase IM and the maximum expiration phase EM, respectively, thereby obtaining the phase state judgment result in which a phase from a maximum expiration phase EM to a maximum inspiration phase IM is judged as an inspiration phase PH1, and a phase from the maximum inspiration phase IM to the maximum expiration phase EM is judged as an expiration phase PH2.

<7-3-1-5. Analysis Range Setting Unit 440>

The analysis range setting unit 440 performs an analysis range setting processing of setting a blood-flow-analysis range in at least one of the inspiration phase PH1 state and the expiration phase PH2 state on the basis of respiratory information and the phase state judgment result. The "respiratory information" herein refers to the respiratory phase PH obtained from respiratory vibration values, the respiratory period PC, and the maximum value B1 and the minimum value B2 of the respiratory vibration values in the respiratory period PC. The analysis range setting unit 440 acquires the respiratory information from the phase state judging unit 430 (see FIG. 38 and FIG. 39).

Specifically, in the analysis range setting processing, a blood-flow-analysis range is set on the basis of respiratory vibration values in at least one respiratory period PC, and also, a blood-flow-analysis range is set to include at least one cardiac period HBC. The blood-flow-analysis range has an analysis range for inspiration phase RA1 and an analysis range for expiration phase RA2 corresponding to the inspiration phase PH1 and the expiration phase PH2, respectively.

Description will be given assuming that a plurality of respiratory periods PC are provided, which is not limited thereto, and one respiratory period PC will suffice. Although description will be given assuming that the analysis range for inspiration phase RA1 and the analysis range for expiration phase RA2 are both set, only any one of the ranges (RA1 or RA2) may be set.

For the amplitude direction AP (see FIG. 40) of the respiratory vibration values, (a) an "amplitude value range RB1" set on the basis of the amplitude value of respiratory vibration values is adopted as a blood-flow-analysis range (see FIG. 44 or the like described below). For the photographing time direction, any one of the ranges is adopted as a blood-flow-analysis range: (c) an "analysis target period RT1" being an analysis target of the respiratory periods PC of the respiratory vibration values acquired in the respiratory information acquiring processing (see FIG. 44 described below) and (d) a "phase-specific analysis target period RT2" corresponding to any one of the inspiration phase PH1 or the expiration phase PH2 of the period being an analysis target period (see FIG. 45 described below). In other words, the blood-flow-analysis range in the sixth embodiment is any of the range satisfying the "amplitude value range RB1" and the "analysis target period RT1" and the range satisfying the "amplitude value range RB1" and the "phase-specific analysis target period RT2."

The "amplitude value range RB1" herein shows any one value in (a1) a range set on the basis of a preset first range or (a2) a range set on the basis of the maximum value B1 and the minimum value B2 of the respiratory vibration values in the respiratory period PC.

Herein, the "first range," the "analysis target period RT1," and the "phase-specific analysis target period RT2" are set by the user inputting them through the operation unit 33 of the image processing apparatus 3 (3'), as shown in FIG. 38, FIG. 39.

Further, if a plurality of "the same amplitude ranges," in which the range of the respiratory vibration values is the same among a plurality of blood-flow-analysis ranges RA that have been set, are present in a plurality of inspiration phases PH1 or a plurality of expiration phases PH2, the analysis range setting processing instructs the blood-flow-analysis value calculating unit 450 to perform any one of processings (e1) to (e3) and a processing (f) described below.

<7-3-1-5-1. Example of Analysis Range Setting Processing>

Figure 44:
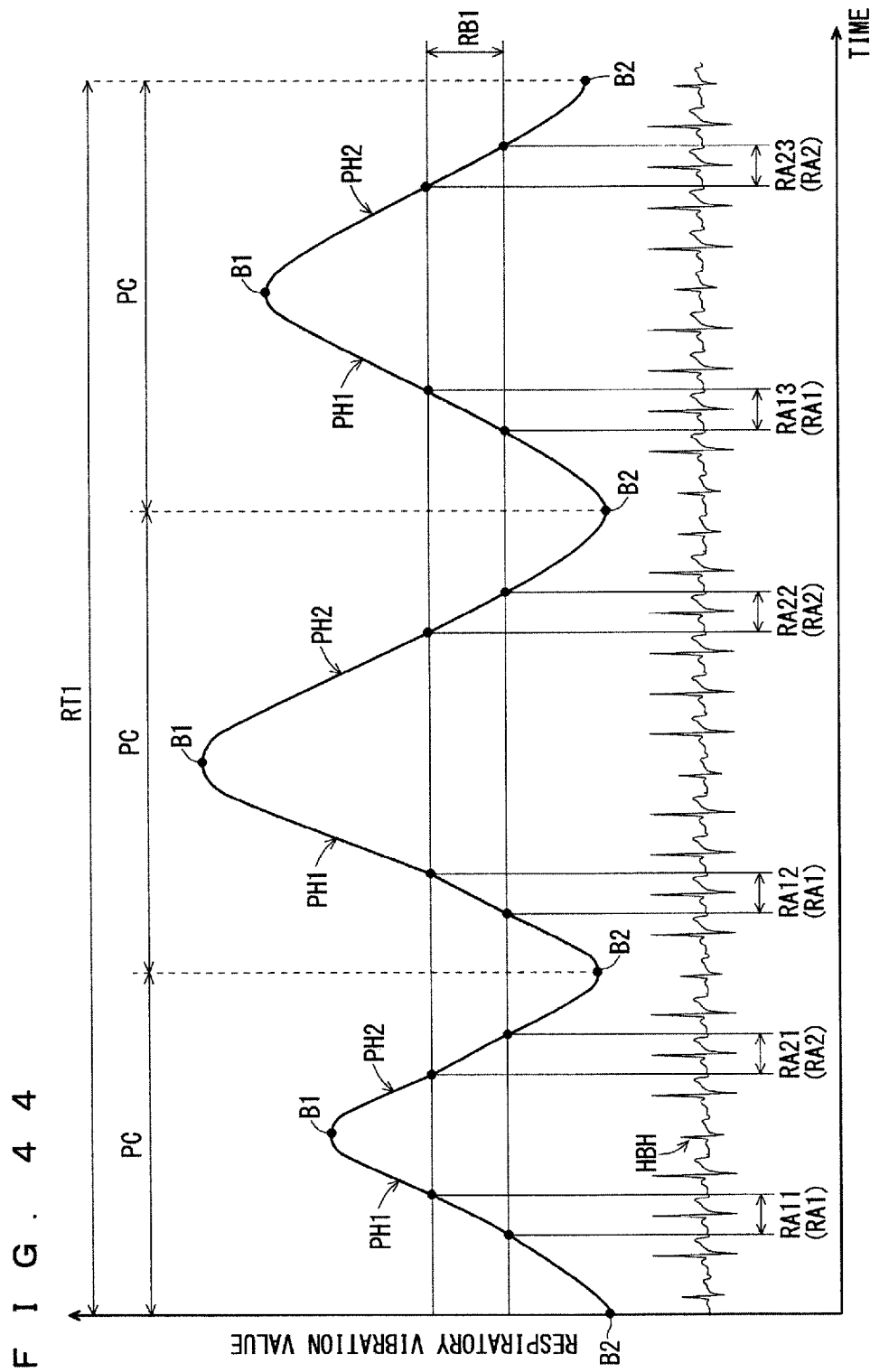
FIG. 44 is a diagram explaining an analysis range setting processing.
Figure 45:
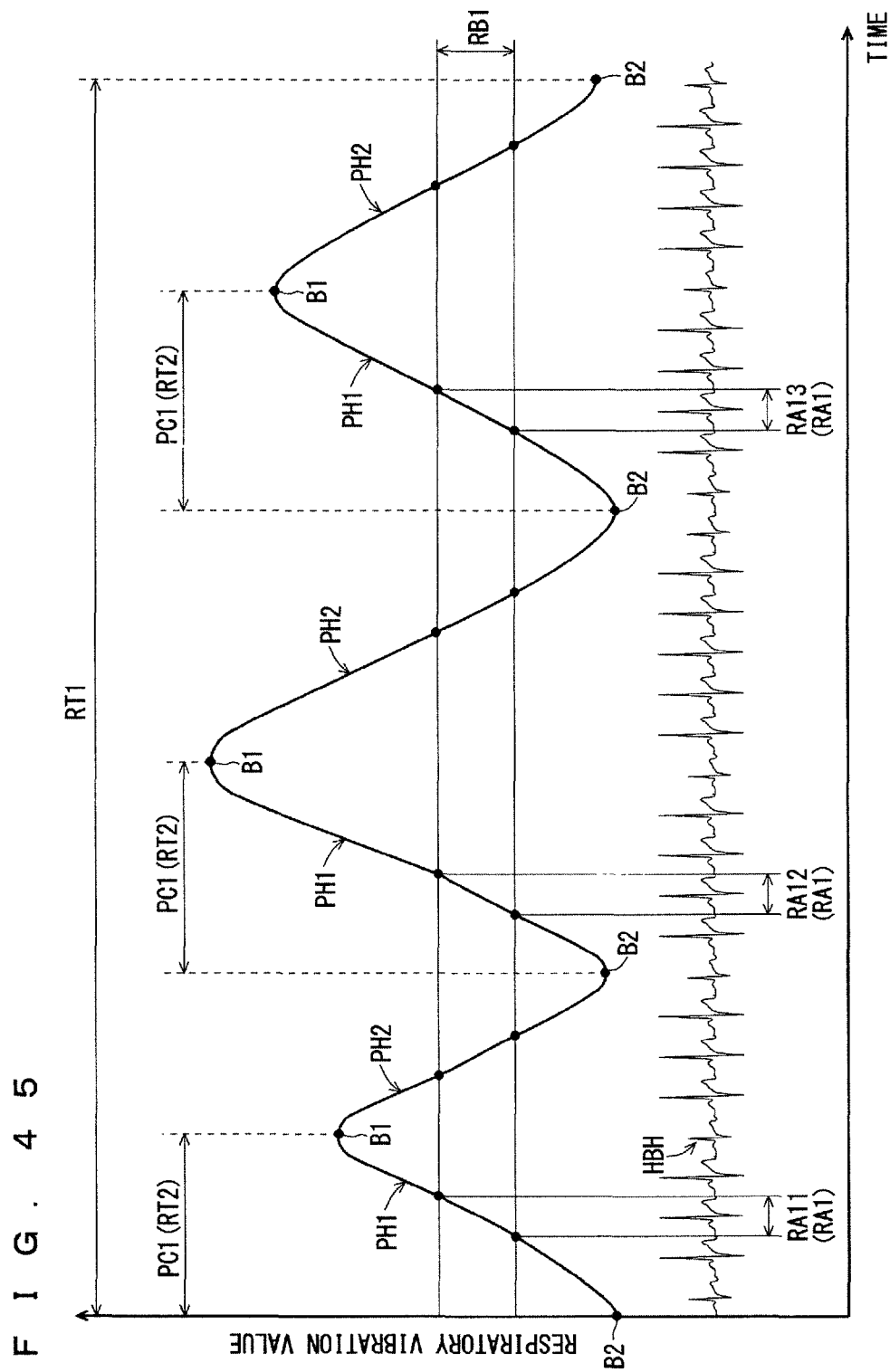
FIG. 45 is another diagram explaining the analysis range setting processing.
Figure 46:
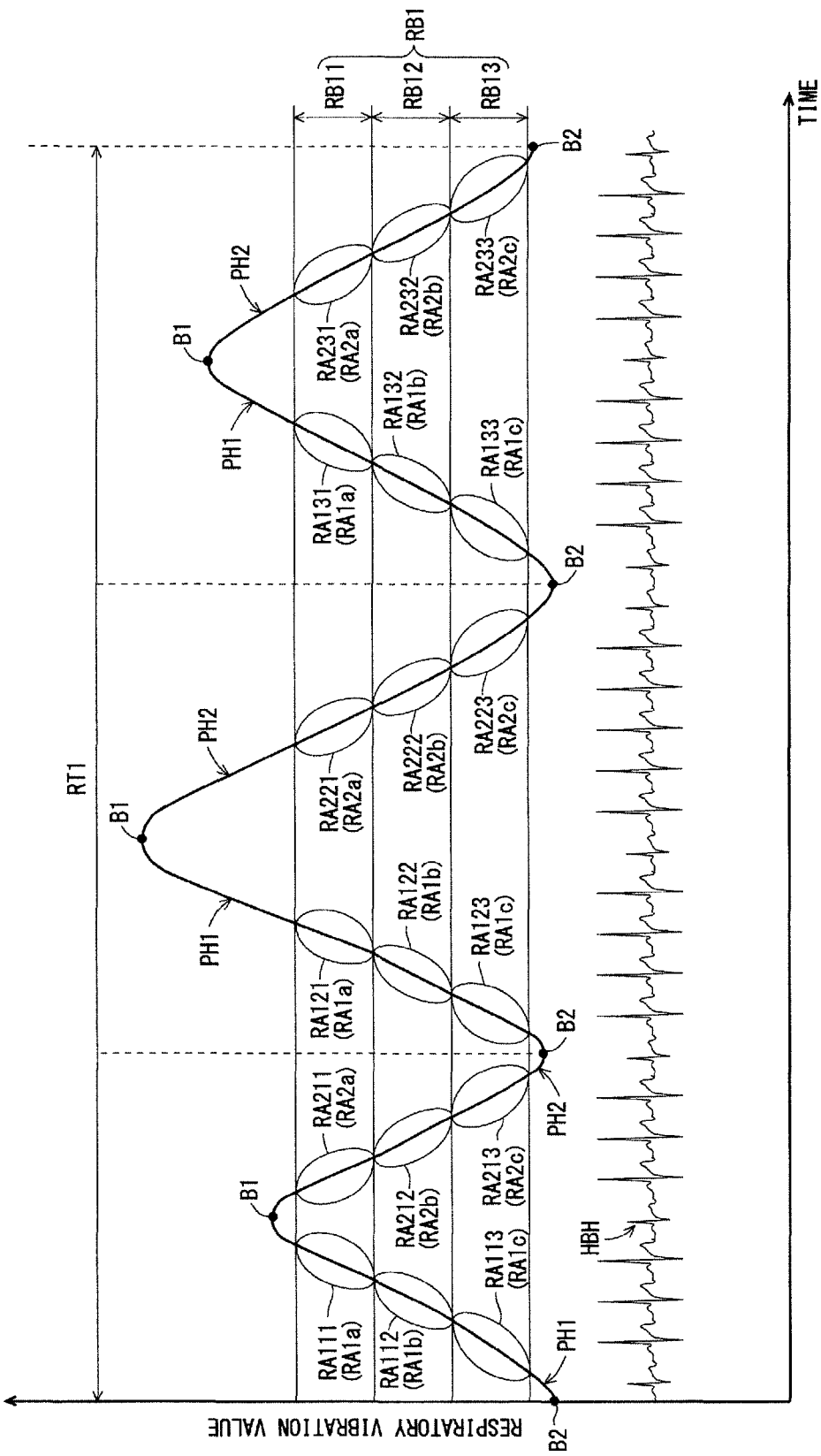
FIG. 46 is still another diagram explaining the analysis range setting processing.

FIG. 44 to FIG. 46 are diagrams explaining the analysis range setting processing, where the horizontal axis represents a time at which a moving image is captured, and the vertical axis represents a respiratory vibration value. Although description will be given of a representative case where an amplitude value range RB1 in FIG. 44 to FIG. 46 is set as the first range of (a1) above, an amplitude value range RB1 may be set by a method of automatically setting it on the basis of a maximum value B1 and a minimum value B2 of respiratory vibration values in the respiratory period PC of (a2) above. In the employment of the method of (a2) above, the amplitude value range RB1 is preferably set almost midway between the maximum value B1 and the minimum value B2.

The blood-flow-analysis range RA shown in FIG. 44 is set to satisfy the amplitude value range RB1 for the amplitude direction AP of respiratory vibration values and satisfy, as an analysis target period RT1, three respiratory periods PC having the respiratory vibration values obtained in the respiratory information acquiring processing for the photographing time direction. As a result, for the blood-flow-analysis range RA, the analysis ranges for inspiration phase RA1 in the inspiration phase PH1 are set as RA11, RA12, and RA13 in the order of photographing time, and the analysis ranges for expiration phase RA2 in the expiration phase PH2 are set as RA21, RA22, and RA23 in the order of photographing time.

In contrast, the blood-flow-analysis range RA shown in FIG. 45 is set as an amplitude value range RB1 for the amplitude direction AP of respiratory vibration values as in FIG. 44; only a half period PC1 corresponding to the inspiration phase PH1 (see FIG. 36) of the analysis target period RT1 similar to that of FIG. 44 is set as the phase-specific analysis target period RT2 for the photographing time direction. As a result, for the blood-flow-analysis range RA, only RA11, RA12, and RA13 are set as the analysis range for inspiration phase RA1 in the order of photographing time.

Although the case where the phase-specific analysis target period RT2 is the inspiration phase PH1 is assumed in FIG. 45, the same holds true for the expiration phase PH2. In other words, the case of the expiration phase PH2 differs from the case of the inspiration phase PH1 (FIG. 45) in that only the half period PC2 corresponding to the expiration phase PH2 (see FIG. 36) is set as the phase-specific analysis target period RT2, so that for the blood-flow-analysis range RA, only RA21, RA22, and RA23 are set as the analysis range for expiration phase RA2 in the order of photographing time.

If the user requests a blood-flow-analysis value only in the inspiration phase PH1 or a blood-flow-analysis value only in the inspiration phase PH2 as described above, an overall range is once determined in the analysis target period RT1, which is set on a period basis, and then, a phase-specific analysis target period RT2 corresponding to any one of the phases can be selected. As a result, the time required for calculation in a blood-flow-analysis value calculating processing described below is halved because the overall period is changed to a half period, reducing a calculation time.

As shown in FIG. 46, the amplitude value range RB1 in the amplitude direction AP of the respiratory vibration values can be set while being divided into RB11, RB12, and RB13 in the descending order of amplitude value of the respiratory vibration value. As in FIG. 44, three periods are set as an analysis target period RT1 for the photographing time direction, so that 18 ranges are set in total as the blood-flow-analysis range RA: the analysis range for inspiration phase RA1 is set as RA113, RA112, RA111, RA123, RA122, RA121, RA133, RA132, and RA131 in the order of photographing time, and the analysis range for expiration phase RA2 is set as RA211, RA212, RA213, RA221, RA222, RA223, RA231, RA232, and RA233 in the order of photographing time.

<7-3-1-5-2. Analysis Range Judging Unit 445>

The analysis range judging unit 445 judges whether the blood-flow-analysis range RA (analysis range for inspiration phase RA1 and/or analysis range for expiration phase RA2), which has been set in the analysis range setting processing, includes at least one (see part (a) of FIG. 47 described below) cardiac period HBC (see FIG. 38 and FIG. 39). If the analysis range judging unit 445 judges that at least one cardiac period HBC is included, the analysis range setting unit 440 formally determines it as a blood-flow-analysis range RA. In contrast, if judging that at least one cardiac period HBC is not included, the analysis range judging unit 445 prompts the analysis range setting processing to extend the blood-flow-analysis range RA in the "photographing time direction" and/or the positive direction and/or the negative direction of the "amplitude direction AP of the respiratory vibration values" to reset the blood-flow-analysis range RA. The analysis range judging unit 445 performs judgment as described above for the reset blood-flow-analysis range RA. The analysis range judging unit 445 repeatedly performs this loop until it finally judges that at least one cardiac period HBC is included. Then, the analysis range setting unit 440 formally determines the final result as the blood-flow-analysis range RA.

<7-3-1-6. Blood-Flow-Analysis Value Calculating Unit 450>

The blood-flow-analysis value calculating unit 450 performs a blood flow analysis on the frame image MI in the blood-flow-analysis range RA set by the analysis range setting unit 440 to perform the blood-flow-analysis value calculating processing of acquiring a blood-flow-analysis value in at least one of the inspiration phase PH1 state and the expiration phase PH2 state.

The blood-flow-analysis value calculating processing refers to a processing of independently performing a blood flow analysis in the analysis range for inspiration phase RA1 and the analysis range for expiration phase RA2 to individually acquire a blood-flow-analysis value. The blood flow analysis herein basically refers to a processing achieved by obtaining a difference between a plurality of frame images MI included in a moving image, in which a processing of removing noise is performed as required. For example, the blood flow analysis method described in Japanese Patent Application Laid-Open No. 2012-110399 is adoptable.

If a blood-flow-analysis range RA is set for at least two respiratory periods PC, the blood-flow-analysis value calculating processing includes a processing of obtaining at least two per-period blood-flow-analysis values SM in at least two respiratory periods PC to finally obtain a blood-flow-analysis value SMR using the at least two per-period blood-flow-analysis values SM (see FIG. 48 and FIG. 49 described below).

If a plurality of "the same amplitude ranges" described above are present, then, the blood-flow-analysis value calculating unit 450 receives an instruction to perform the processing, described below, in the analysis range setting processing of the analysis range setting unit 440, and accordingly, performs the processing in accordance with the contents of the instruction.

In other words, this processing includes, for a plurality of per-period blood-flow-analysis values SM calculated in a plurality of the same amplitude ranges, any one of (e1) a processing of calculating an in-range average value indicating an averaged value as a blood-flow-analysis value SMR, (e2) a processing of calculating an in-range maximum value indicating a maximum value as a blood-flow-analysis value SMR, and (e3) a processing of calculating an in-range minimum value showing a minimum value as a blood-flow-analysis value SMR, and (f) a processing of generating an image (final image) RG using any one of an in-range average value, an in-range maximum value, and an in-range minimum value.

Finally, the blood-flow-analysis value calculating unit 450 outputs the blood-flow-analysis value SMR or the final image RG to be used in image diagnosis to the storage unit 32 or the display unit 34 (see FIG. 38 and FIG. 39).

<7-3-1-6-1. Case where a Plurality of Same Amplitude Ranges are Present in Each Phase>

With the example of the blood-flow-analysis range RA set in FIG. 44 as the case where a plurality of the same amplitude ranges are present in a plurality of inspiration phases PH1 and a plurality of expiration phases PH2, a method of calculating a per-period blood-flow-analysis value SM and a blood-flow-analysis value SMR and the final image RG will be described below.

<7-3-1-6-1-1. Per-Period Blood-Flow-Analysis Value SM>

FIG. 47 to FIG. 49 are diagrams explaining the blood-flow-analysis value calculating processing. Part (a) of FIG. 47 is a diagram schematically explaining the relationship between a frame image MI and a cardiac period HBC in each blood-flow-analysis range RA, where the horizontal axis represents a photographing time, and the vertical axis represents the width of the heart for the first cardiac period acquiring processing and represents an electrical signal detected by the electrocardiograph 4 for the second cardiac period acquiring processing. Part (b) of FIG. 47 shows a difference image DG generated from a total of difference values between frame images MI in each blood-flow-analysis range RA of part (a) of FIG. 47 (that is, corresponding to a per-period blood-flow-analysis value SM).

Each blood-flow-analysis range RA herein shows any one representative range of the analysis ranges for inspiration phase RA11 to RA13 and the analysis ranges for expiration phase RA21 to RA23 shown in FIG. 44. The example of part (a) of FIG. 47 assumes seven frame images MI in the blood-flow-analysis range RA and six time differences Δt1 to Δt6, which is merely an example. In practice, the blood-flow-analysis range RA can be set in accordance with the frame rate of photographing of a moving image.

As shown in part (a) of FIG. 47, each blood-flow-analysis range RA, set by the analysis range setting unit 440 through judgment of the analysis range judging unit 445, is set to include at least one cardiac period HBC. Thus, differences between frame images MI in each blood-flow-analysis range RA are obtained in the order of photographing time, and difference values d1 to d6 respectively corresponding to the time differences Δt1 to Δt6 are obtained, thereby obtaining difference values for one period HBC of heartbeat. A per-period blood-flow-analysis value SM is obtained as a total of the difference values d1 to d6, and accordingly, one difference image DG is obtained as shown in part (b) of FIG. 47.

In other words, the difference values d1 to d6 individually correspond to a blood flow in the lung field. For example, a blood flow is concentrated near the heart at peak heartbeat (refer to a point Rp in FIG. 43), and thus, near the heart (for example, see a region dr in part (b) of FIG. 47), a density value difference increases and a difference value increases in the frame image. Contrastingly, a blood flow is concentrated in the region located far from the heart at a time distant from the peak heartbeat (for example, see a point Up in FIG. 43), and thus, in the region located far from the heart (for example, a region du in part (b) of FIG. 47), a density value difference increases and a difference value increases in the frame image.

As described above, a difference value (density value difference), which is a large value, moves in a frame image (changes spatially) with photographing time between frame images (temporal change). Then, differences between frame images MI corresponding to one cardiac period HBC are obtained and a total of difference values is obtained, to thereby obtain a per-period blood-flow-analysis value SM. Then, one difference image DG is generated on the basis of the per-period blood-flow-analysis value SM, enabling examination of the whole picture in which a blood flow circulates in the entire lung field region. Thus, if the test subject M is not a healthy person, the movement of a blood flow in the lung field can be also understood, for example, a region in which a blood flow does not circulate in the lung field region is found.

<7-3-1-6-1-2. Blood-Flow-Analysis Value SMR and Final Image RG>

Then, with reference to FIG. 44, FIG. 48, and FIG. 49, description will be given of a processing of performing a blood flow analysis independently in the analysis range for inspiration phase RA1 and the analysis range for expiration phase RA2 to finally obtain a blood-flow-analysis value SMR using a plurality of per-period blood-flow-analysis values SM.

The blood-flow-analysis value calculating processing is performed independently in the analysis range for inspiration phase RA1 (RA11 to RA13) and the analysis range for expiration phase RA2 (RA21 to RA23) shown in FIG. 44. In other words, in the example of FIG. 44, the three same amplitude ranges described above are present in each of three inspiration phases PH1 and three expiration phases PH2.

First, as in the method of calculating a per-period blood-flow-analysis value SM, the blood-flow-analysis value calculating processing calculates, in the analysis ranges for inspiration phase RA11, RA12, and RA13 (see FIG. 44), per-period blood-flow-analysis values SM11, SM12, and SM13 (see FIG. 48), respectively. In parallel with this, in the analysis ranges for expiration phase RA21, RA22, and RA23 (see FIG. 44), the corresponding per-period blood-flow-analysis values SM21, SM22, and SM23 are calculated individually (see FIG. 49).

Difference images DG11 to DG13 and DG21 to DG23 shown in FIG. 48 and FIG. 49 are generated on the basis of the per-period blood-flow-analysis values SM11 to SM13 and SM21 to SM23, respectively, which are merely illustrated for the sake of description. In practice, they need not to be generated as images, and it is important to obtain per-period blood-flow-analysis values SM11 to SM13 and SM21 to SM23.

Then, the blood-flow-analysis value calculating processing performs any one of the processings (e1) to (e3) on the per-period blood-flow-analysis values SM11 to SM13 in the analysis range for inspiration phase RA1. In other words, in the adoption of the processing (e1) as shown in FIG. 48, a process of calculating, as a blood-flow-analysis value SMR1, an in-range average value indicating a value obtained by averaging the per-period blood-flow-analysis values SM11 to SM13 is performed. In adoption of the processing (e2), a processing of calculating, as a blood-flow-analysis value SMR1, an in-range maximum value indicating a maximum value among the per-period blood-flow-analysis values SM11 to SM13 is performed. Further, in the adoption of the processing (e3), a processing of calculating, as a blood-flow-analysis value SMR1, an in-range minimum value indicating a minimum value among the per-period blood-flow-analysis values SM11 to SM13 is performed.

In parallel with this, also in the analysis range for expiration phase RA2, the blood-flow-analysis value calculating processing performs any of the processings (e1) to (e3) individually. In other words, as shown in FIG. 49, in the adoption of the processing (e1), a processing of calculating, as a blood-flow-analysis value SMR2, an in-range average value indicating a value obtained by averaging the per-period blood-flow-analysis values SM21 to SM23 is performed. In the adoption of the processing (e2), a processing of calculating, as a blood-flow-analysis value SMR2, an in-range maximum value indicating a maximum value among the per-period blood-flow-analysis values SM21 to SM23 is performed. Further, in the adoption of the processing (e3), a processing of calculating, as a blood-flow-analysis value SMR2, an in-range minimum value indicating a minimum value among the per-period blood-flow-analysis values SM21 to SM23 is performed.

One example of the method of determining an in-range maximum value and an in-range minimum value in (e2) and (e3) is a method of determining those values on the basis of a pixel value (density value) in a diagnosis region that a user wants to perform image diagnosis.

The blood-flow-analysis value calculating processing individually performs a blood flow analysis in each of the analysis range for inspiration phase RA1 and the analysis range for expiration phase RA2, thereby individually obtaining blood-flow-analysis values SMR1 and SMR2.

Finally, in the analysis range for inspiration phase RA1 the blood-flow-analysis value calculating processing (f) finally generates a final image RG1 using the blood-flow-analysis value SMR1, which is any one of an in-range average value, an in-range maximum value, and an in-range minimum value. In parallel with this, also in the analysis range for expiration phase RA2, the blood-flow-analysis value calculating processing (f) finally generates a final image RG2 using the blood-flow-analysis value SMR2, which is any one of an in-range average value, an in-range maximum value, and an in-range minimum value.

Then, the blood-flow-analysis value calculating unit 450 outputs the blood-flow-analysis values SMR1 and SMR2 or two final image RG1 and RG2 to be used in image diagnosis to the storage unit 32 or the display unit 34.

<7-3-1-6-2. Case where a Plurality of Same Amplitude Ranges are Present in Each Phase>

Description has been given of the blood-flow-analysis value SMR in the case where one type of the same amplitude range is present in each of a plurality of inspiration phases PH1 and a plurality of expiration phases PH2 (see FIG. 44). Hereinafter, the blood-flow-analysis value SMR in the case where a plurality of different types of the same amplitude ranges are present in each of a plurality of inspiration phases PH1 and a plurality of expiration phases PH2 will be described with reference to FIG. 46.

<7-3-16-2-1. Per-Period Blood-Flow-Analysis Value SM>

First, a method of calculating a per-period blood-flow-analysis value SM will be described. As shown in FIG. 46, three types of the same amplitude ranges are present in three inspiration phases PH1 and three expiration phases PH2. Specifically, an analysis range for inspiration phase RA1$a$ (RA111 to RA131), an analysis range for inspiration phase RA1$b$ (RA112 to RA132), and an analysis range for inspiration phase RA1$c$ (RA113 to RA133) are present in three inspiration phases PH1 as three types of the same amplitude ranges. Also, an analysis range for expiration phase RA2$a$ (RA211 to RA231), an analysis range for expiration phase RA2$b$ (RA212 to RA232), and an analysis range for expiation phase RA2$c$ (RA213 to RA233) are present in three expiration phases PH2 as three types of the same amplitude ranges.

The blood-flow-analysis value calculating processing calculates per-period blood-flow-analysis values SM111 to SM131 from the analysis range for inspiration phase RA1$a$ (RA111 to RA133), calculates per-period blood-flow-analysis values SM112 to SM132 from the analysis range for inspiration phase RA1$b$ (RA112 to RA132), and calculates per-period blood-flow-analysis value SM113 to SM133 from the analysis range for inspiration phase RA1$c$ (RA113 to RA133), as in the case of FIG. 44 described above.

In parallel with this, the blood-flow-analysis value calculating processing individually calculates per-period blood-flow-analysis values SM211 to SM231 from the analysis range for expiration phase RA2$a$ (RA211 to RA231), calculates per-period blood-flow-analysis values SM212 to SM232 from the analysis range for expiration phase RA2$b$ (RA212 to RA232), and calculates per-period blood-flow-analysis values SM213 to SM233 from the analysis range for expiration phase RA2$c$ (RA213 to RA233).

<7-3-1-6-2-2. Blood-Flow-Analysis Value SMR and Final Image RG>

Next, the method of calculating a blood-flow-analysis value SMR and the final image RG will be described. As in the case of FIG. 44 described above, the blood-flow-analysis value calculating processing performs any of the processings (e1) to (e3) on the per-period blood-flow-analysis values SM111 to SM131 to calculate a blood-flow-analysis value SMR1$a$, and performs any of the processings (e1) to (e3) on the per-period blood-flow-analysis values SM112 to SM132 and the per-period blood-flow-analysis values SM113 to SM133 to calculate blood-flow-analysis values SMR1$b$ and SMR1$c$.

In parallel with this, the blood-flow-analysis value calculating processing individually performs any of the processings (e1) to (e3) on the per-period blood-flow-analysis values SM211 to SM231 to calculate a blood-flow-analysis value SMR2$a$, and also performs any of the processings (e1) to (e3) on the per-period blood-flow-analysis values SM212 to SM232 and the per-period blood-flow-analysis values SM213 to SM233 to calculate blood-flow-analysis values SMR2$b$ and SMR2$c$.

Finally, in each of the analysis ranges for inspiration phase RA1$a$, RA1$b$, and RA1$c$, the blood-flow-analysis value calculating processing (f) uses any one of an in-range average value, an in-range maximum value, and an in-range minimum value as the blood-flow-analysis values SMR1$a$, SMR1$b$, and SMR1$c$, thereby finally generating final images RG1$a$, RG1$b$, and RG1$c$ using the blood-flow-analysis values SMR1$a$, SMR1$b$, and SMR1$c$. Also, in parallel with this, in each of the analysis ranges for expiration phase RA2$a$, RA2$b$, and RA2$e$, the blood-flow-analysis value calculating processing (f) uses any one of an in-range average value, an in-range maximum value, and an in-range minimum value as the blood-flow-analysis values SMR2$a$, SMR2$b$, and SMR2$c$, thereby finally generating final images RG2$a$, RG2$b$, and RG2$c$ using the blood-flow-analysis values SMR2$a$, SMR2$b$, and SMR2$c$.

Then, the blood-flow-analysis value calculating unit 450 outputs the blood-flow-analysis values SMR1$a$, SMR1$b$, SMR1$c$, SMR2$a$, SMR2$b$, and SMR2$c$, or six images, namely, the final images RG1$a$, RG1$b$, RG1$c$, RG2$a$, RG2$b$, and RG2$c$ to be used in image diagnosis, to the storage unit 32 or the display unit 34.

<7-4. Basic Operation of Image Processing Apparatus 3 (3')>

Figure 50:
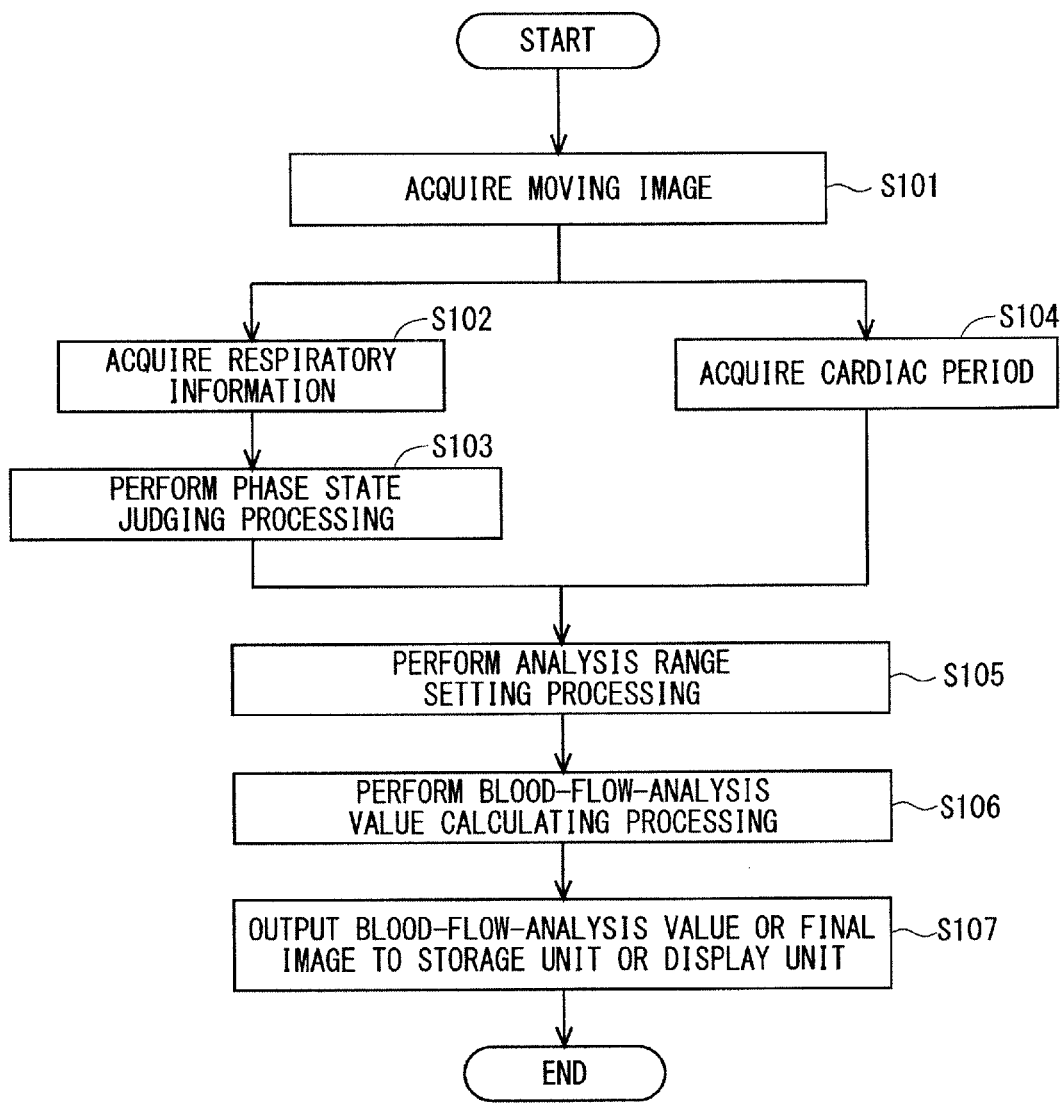
FIG. 50 is a flowchart explaining the basic operation of the image processing apparatus 3 (3') achieved in the sixth embodiment.
Figure 51:
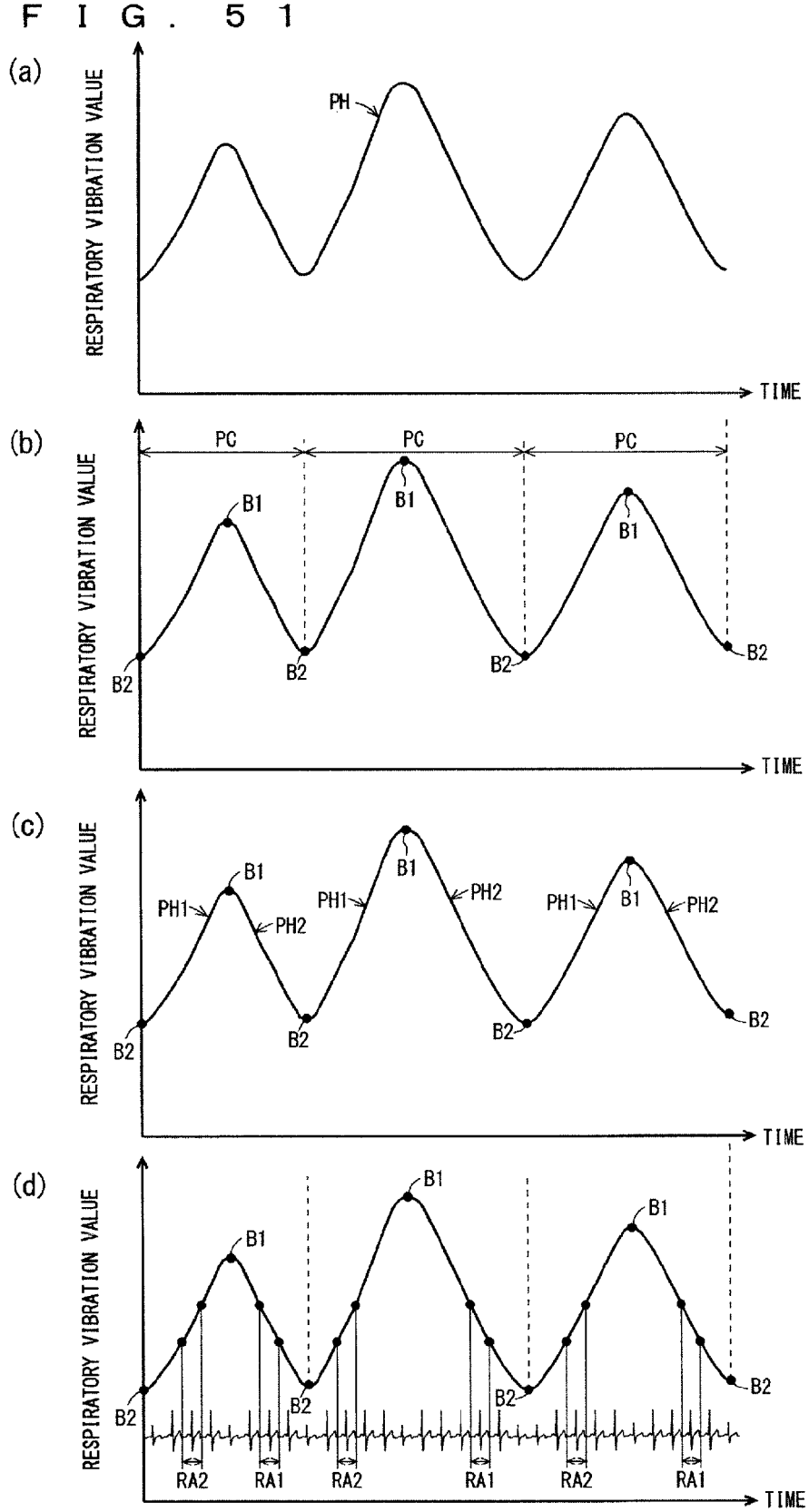
FIG. 51 is a schematic diagram explaining the basic operation of the image processing apparatus 3 (3') achieved in the sixth embodiment.

FIG. 50 is a flowchart explaining the basic operation achieved in the image processing apparatus 3 (3') according to this embodiment. FIG. 51 is a schematic diagram simply showing the flow of the basic operation. The individual functions of the units have been described above (see FIG. 38 and FIG. 39), and thus, only the overall flow will be described here.

As shown in FIG. 50, first, in Step S101, the moving image acquiring unit 410 of the control unit 31E (31E') acquires a moving image (a plurality of frame images MI) captured by the reading control device 14 of the photographing apparatus 1 through the photographing control apparatus 2.

In Step S102, the respiratory information acquiring unit 420 or 420' performs the first or second respiratory information acquiring processing of acquiring respiratory information synchronized at times at which frame images are captured to detect the respiratory phase PH and the respiratory period PC based on respiratory vibration values, and a maximum value B1 and a minimum value B2 of the respiratory vibration values in the respiratory period PC, and the respiratory period PC (see FIG. 5, FIG. 6, FIG. 40, part (a) of FIG. 51, and part (b) of FIG. 51.

In Step S103, the phase state judging unit 430 judge to which of the inspiration phase PH1 state and the expiration phase PH2 state the respiratory vibration values acquired in Step S102 belong, thereby obtaining a phase state judgment result (see part (c) of FIG. 51.

In Step S104, the cardiac period acquiring unit 425 or 425' performs the first or second cardiac period acquiring processing synchronized at a time at which a frame image is captured, detecting a cardiac period HBC (see FIG. 41 to FIG. 43).

Step S104 may be processed in parallel with Step S102 and Step S103 or may be processed before or after Step S102 and Step S103. In other words, it suffices that Step S104 is performed before Step S105.

In Step S105, the analysis range setting unit 440 sets a blood-flow-analysis range RA in at least one of the inspiration phase PH1 state and the expiration phase PH2 state on the basis of the phase state judgment result obtained in Step S104. Here, the blood-flow-analysis range RA is set on the basis of the result on the judgment performed by the analysis range judging unit 445 (see FIG. 44 to FIG. 46, and part (d) of FIG. 51).

In Step S105, the analysis range setting unit 440 instructs the blood-flow-analysis value calculating unit 450 (blood-flow-analysis value calculating processing) to perform any of the processings (e1)) to (e3) for the per-period blood-flow-analysis value SM.

In Step S106, the blood-flow-analysis value calculating unit 450 performs a blood flow analysis independently in the analysis range for inspiration phase RA1 and the analysis range for expiration phase RA2, thereby obtaining a blood-flow-analysis value SMR separately. In a case where a plurality of the same amplitude ranges are present the blood-flow-analysis value calculating processing calculates a per-period blood-flow-analysis value SM and performs any of the processings (e1) to (e3) instructed in Step S105 in a plurality of the same amplitude ranges, thereby calculating a blood-flow-analysis value SMR. Then, the blood-flow-analysis value calculating unit 450 (f) determines any one of the in-range average value, the in-range maximum value, and the in-range minimum value as a blood-flow-analysis value SMR, thereby finally generating one final image RG using the blood-flow-analysis value SMR (see FIG. 47 to FIG. 49).

Finally, in Step S107, the blood-flow-analysis value calculating unit 450 outputs the blood-flow-analysis value SMR or the final image RG obtained in Step S106 to the storage unit 32 or the display unit 34 (see FIG. 38 and FIG. 39), and then, the operational flow is ended.

As described above, the image processing apparatus 3 (3') according to the sixth embodiment sets a blood-flow-analysis range RA in at least one of the inspiration phase PH1 state and the expiration phase PH2 state on the basis of the respiratory information and the phase state judgment result, and performs a blood flow analysis on a frame image MI in a blood-flow-analysis range RA, thereby obtaining a blood-flow-analysis value SMR in the at least one of the states. As a result, an appropriate blood-flow-analysis value SMR desired by a user, which corresponds to at least one of the inspiration phase PH1 state and the expiration phase. PH2 state, that is, which reflects the phase state of respiration, can be obtained. This enables appropriate, efficient image diagnosis of a blood flow.

The analysis range setting processing sets a blood-flow-analysis range RA to include at least one cardiac period HBC. This obtains a blood-flow-analysis value SMR in the state where at least one cardiac period HBC is included. As a result, the movement of a blood flow for the entire one period of heartbeat can be understood (see FIG. 47).

The blood-flow-analysis value calculating processing performs a processing of performing a blood flow analysis independently in each of the analysis range for inspiration phase RA1 and the analysis range for expiration phase RA2 to individually obtain blood-flow-analysis values SMR (SMR1, SMR2). This prevents a decrease in the accuracy of blood flow analysis associated with a difference in the pressure exerted on the blood vessel in the lung field between in the inspiration phase PH1 state and in the expiration phase PH2 state. Thus, image diagnosis of a blood flow corresponding to each of the inspiration phase PH1 state and the expiration phase PH2 state is enabled.

The blood-flow-analysis range RA is set as a range that satisfies the amplitude value range RB1 for the amplitude direction AP of the respiratory vibration values in one or more respiratory periods PC and satisfies any one of the analysis target period RT1 and the phase-specific analysis target period RT2 for the photographing time direction, thereby setting a blood-flow-analysis range RA according to the use by a user. If the user needs a blood-flow-analysis value SMR in any one of the expiration phase PH2 state and the inspiration phase PH1 state, setting in the phase-specific analysis target period RT2 needs only a calculation performed in the blood-flow-analysis value calculating processing in one of the phase states. Therefore, compared with the case where setting is performed in the analysis target period, a calculation time is reduced (see FIG. 44 and FIG. 45).

In the case where the amplitude value range RB1 is set on the basis of (a1) the preset first range, it can be determined automatically without the user's taking into account respiratory vibration values. In the case where the amplitude value range RB1 is set on the basis of (a2) the maximum value B1 and the minimum value B2 of the respiratory vibration values in the respiratory period PC, an appropriate amplitude value range RB1 corresponding to the respiratory vibration value can be set automatically.

The blood-flow-analysis value calculating processing performs a processing of obtaining at least two per-period blood-flow-analysis values SM in at least two respiratory periods PC to finally obtain a blood-flow-analysis value SMR using the at least two per-period blood-flow-analysis values SM. As a result, a final blood-flow-analysis value SMR, which cannot be achieved in blood flow analysis of one period of respiration, can be determined in at least one of the inspiration phase PH1 state and the expiration phase PH2 state by comprehensively taking into account a plurality of per-period blood-flow-analysis values SM. This enables more appropriate, efficient image diagnosis of a blood flow.

A respiratory period PC is calculated on the basis of respiratory vibration values to calculate a maximum value B1 and a minimum value B2 of the respiratory vibration values per respiratory period PC. In typical cases, the maximum value B1 and the minimum value B2 of the respiratory vibration values per respiratory period PC differ per respiratory period PC. Thus, for example, in the case where the maximum value B1 and the minimum value B2 for the amplitude value range are set per respiratory period PC, an individual amplitude value range RB1 can be set per respiratory period PC.

The phase state judging processing judges to which of the inspiration phase PH1 state and the expiration phase PH2 state a respiratory vibration value belongs on the basis of the maximum value BE and the minimum value B2 of the respiratory vibration values in the respiratory period PC. This enables appropriate, easy judgment of the phase state of the respiratory vibration values on the basis of the maximum inspiration phase IM and the maximum expiration phase EM corresponding respectively to the maximum value B1 and the minimum value B2 of the respiratory vibration values in the respiratory period PC (see FIG. 36 and FIG. 40).

Further, the analysis range setting processing performs a processing of instructing the blood-flow-analysis value calculating unit 450 to perform, on a plurality of per-period blood-flow-analysis values SM to be calculated in a plurality of the same amplitude ranges, any one of (e1) a processing of calculating an in-range average value indicating an averaged value as a blood-flow-analysis value SMR, (e2) a processing of calculating an in-range maximum value indicating a maximum value as a blood-flow-analysis value SMR, and (e3) a processing of calculating an in-range minimum value indicating a minimum value as a blood-flow-analysis value SMR, and (f) a processing of generating one image RG using any one of an in-range average value, an in-range maximum value, and an in-range minimum value. In the case where one image RG is generated using an in-range average value, high-frequency noise components included in a per-period blood-flow-analysis value SM can be reduced, thereby generating a smoothed image. The accuracy of blood flow analysis decreases due to an attenuated blood flow in the lung field region near the maximum inspiration phase IM. Therefore, for diagnosis of an image with a blood-flow-analysis value SMR near the maximum inspiration phase IM, one image RG is effectively generated using an in-range maximum value. Further, the image RG generated using an in-range maximum value is compared with an image RG generated using an in-range minimum value to diagnose a difference therebetween per respiratory period PC.

8. Seventh Embodiment

An image processing apparatus 3A (not shown) in the seventh embodiment of the present invention differs from the image processing apparatus 3 (3') according to the sixth embodiment in the respiratory information acquiring processing and the analysis range setting processing described below. The remaining components are similar to those of the image processing apparatus 3 (3'), which holds true for the basic operation (see FIG. 50 and FIG. 51).

<8-1. Respiratory Information Acquiring Processing>

The respiratory information acquiring processing according to the seventh embodiment includes the processing of calculating a maximum value B1 and a minimum value B2 of the respiratory vibration values in a respiratory period PC in the sixth embodiment, and further includes a processing of calculating an overall maximum value MX indicating a maximum respiratory vibration value in an overall time.

<8-2. Analysis Range Setting Processing>

The analysis range setting processing in the seventh embodiment does not adopt, in setting a blood-flow-analysis range RA, (a) an amplitude value range RB1 set on the basis of the amplitude values of respiratory vibration values in the sixth embodiment, for the amplitude direction AP of the respiratory vibration values in at least one respiratory period PC.

In other words, (b) a "diagnostic purpose range RB2" (see FIG. 52 and FIG. 53 below) to be set in accordance with the diagnostic purpose is adopted as the blood-flow-analysis range RA in the seventh embodiment, for the amplitude direction AP of the respiratory vibration values in at least one respiratory period PC. For the photographing time direction, as in the sixth embodiment, the blood-flow-analysis range RA is any one of the ranges (c) and (d).

In other words, the blood-flow-analysis range RA in the seventh embodiment is any of the range that satisfies the "diagnostic purpose range RB2" and the "analysis target period RT1" and the range that satisfies the "diagnostic purpose range RB2" and the "phase-specific analysis target period RT2."

The diagnostic purpose range can be set depending on the diagnostic purpose desired by a user. The diagnostic purpose range is set by the user inputting it through the operation unit 33 of the image processing apparatus 3A as in the sixth embodiment (see FIG. 38 and FIG. 39). Two diagnostic purpose ranges RB2 will be described below.

<8-2-1. Diagnostic Purpose Range RB2 (Almost Midway Between Maximum Value B1 and Minimum Value B2)>

When the user wants to diagnose a blood flow per se inside the lung field, the diagnostic purpose range RB2 is preferably a range set in a range in which respiratory vibration values in the respiratory period PC are larger than the minimum value B2 and smaller than the maximum value B1. In other words, as described in the problems (i) and (ii), with the maximum value B1 (maximum inspiration phase IM) and the minimum value B2 (maximum expiration phase EM) of the respiratory vibration values in the respiratory period PC, the pressure on the blood vessel in the lung field differs from a normal pressure, which is not a favorable condition for a blood flow. Thus, as a range of the best blood flow, for example, the diagnostic purpose range is preferably set almost midway between the maximum value B1 and the minimum value B2.

Figure 52:
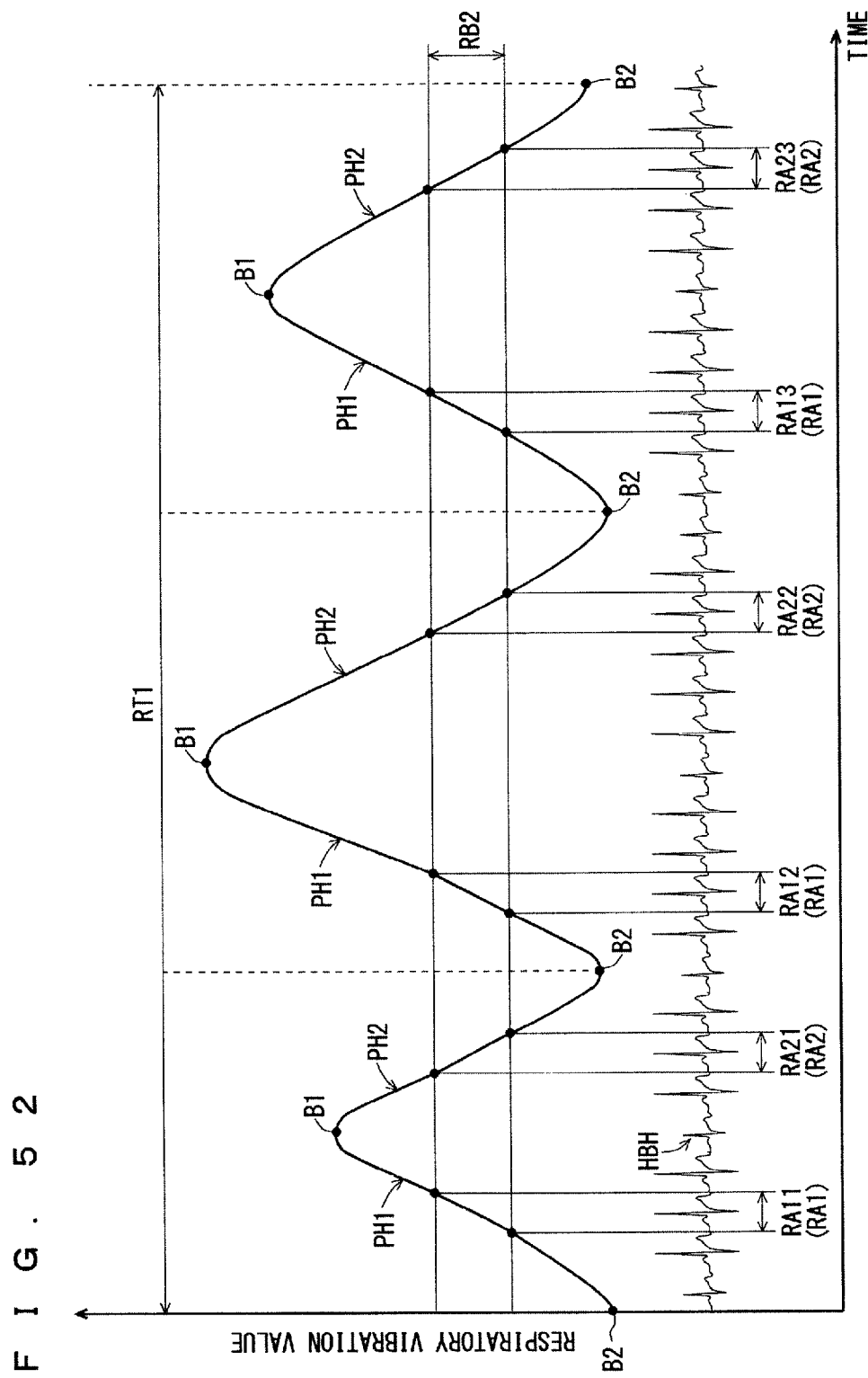
FIG. 52 is a diagram showing an example of a diagnostic purpose range.

FIG. 52 is a diagram explaining the case where a diagnostic purpose range is set almost midway between the maximum value B1 and the minimum value B2. As shown in FIG. 52, the diagnostic purpose range RB2 is set almost midway between the maximum value B1 and the minimum value B2 as the range in which respiratory vibration values in the respiratory period PC are larger than the minimum value B2 and is smaller than the maximum value B1. Analysis ranges for inspiration phase RA1 (RA11, RA12, RA13) and analysis ranges for expiration phase RA2 (RA21, RA22, RA23), which are set on the basis of the diagnostic purpose range RB2, are set as ranges of the best blood flow.

As described above, in the analysis range setting processing according to the seventh embodiment, the diagnostic purpose range RB2 is set as the range in which respiratory vibration values are larger than the minimum value B2 and smaller than the maximum value B1. In other words, in a maximum inspiration phase IM and a maximum expiration phase EM respectively corresponding to the maximum value B1 and the minimum value B2 of the respiratory vibration values, a pressure on the blood vessel in the lung field differs from a normal pressure, resulting in a poor blood flow condition (see the problems (i) and (ii) above). Thus, eliminating the two phase states allows the range of the best blood flow to be set as the blood-flow-analysis range RA, resulting in a stable blood-flow-analysis value SMR.

<8-2-2. Diagnostic Purpose Range RB2 (Region in the Vicinity of Overall Maximum Value MX)>

When the user wants to diagnose the shape of blood vessels in the lung field region, the diagnostic purpose range RB2 is preferably set in a range near the overall maximum value MX. This is because the lung is stretched vertically in the inspiration phase PH1, so that a blood vessel becomes narrow while the blood vessel itself is stretched most in the lung field. Adopting this state as the blood-flow-analysis range RA enables check of the shape of the blood vessels (how blood vessels run throughout) in the lung field.

Specifically, the diagnostic purpose range RB2 is preferably a range that is in the vicinity of the overall maximum value MX and excludes the overall maximum value MX.

FIG. 53 is a diagram explaining the case where the diagnostic purpose range RB2 is a range in the vicinity of the overall maximum value MX. As shown in FIG. 53, the diagnostic purpose range RB2 is set as the range that is in the vicinity of the overall maximum value MX and excludes the overall maximum value MX. Analysis ranges for inspiration phase RA1 (RA12, RA13) and analysis ranges for expiration phase RA2 (RA22, RA23), which are set in the diagnostic purpose range RB2, are determined as the ranges in which the shape of the blood vessels extends most in the lung field region. Here, the overall maximum value MX is preferably eliminated from the blood-flow-analysis range RA because the phenomena (i) and (ii) in which a blood flow is restricted (a blood flow is attenuated) highly likely occur, resulting in a risk that a normal blood-flow-analysis value SMR may not be obtained.

The maximum value B1a shown in FIG. 53 is not included in the range in the vicinity of the overall maximum value MX, and thus, a respiratory period PCa includes no blood-flow-analysis range RA. This is conceivably a situation in which the maximum value B1a in the respiratory period PCa is smaller than the maximum value B1b (overall maximum value MX) and the maximum values B1c in the respiratory periods PCb and PCc, and accordingly, the lung is not inflated completely (is not fully stretched vertically) in the vicinity of the maximum value B1a. Therefore, the maximum value B1a is not suitable for understanding the shape of blood vessels in the lung field region, which causes no problem if the maximum value B1a is eliminated from the blood-flow-analysis range RA.

As described above, in the analysis range setting processing in the seventh embodiment, the diagnostic purpose range RB2 is set in the range in the vicinity of the overall maximum value MX, allowing the blood-flow-analysis range RA to be set near the maximum inspiration phase IM. In other words, near the maximum inspiration phase TM, the blood vessels of the lung field region are stretched most in the lung field. For this reason, the blood-flow-analysis range RA is set near the maximum inspiration phase IM to perform a blood flow analysis, whereby the shape of the blood vessels in the lung field can be understood.

The diagnostic purpose range RB2 is set as the range that is in the vicinity of the overall maximum value MX and excludes the overall maximum value MX, allowing the blood-flow-analysis range RA to be set near the maximum inspiration phase IM in which the blood vessels of the lung field region are stretched most in the lung field. Therefore, the shape of the blood vessels in the lung field can be understood from the obtained blood-flow-analysis value SMR.

Further, a phenomenon in which a blood flow through the blood vessels in the lung field region is restricted and the blood flow is attenuated occurs in the maximum inspiration phase IM corresponding to the overall maximum value MX (see the problems (i) and (ii)). Thus, the shape of the blood vessels in the lung field is hard to understand if a blood flow analysis is performed. Therefore, an appropriate blood-flow-analysis value SMR can be obtained by eliminating the overall maximum value MX from the blood-flow-analysis range RA.

<9. Modifications (Sixth Embodiment and Seventh Embodiment)>

While a second embodiment group (the sixth embodiment and the seventh embodiment) of the present invention has been described above, the present invention is not limited to the second embodiment group and can be modified variously.

While the second embodiment group has described the image processing apparatuses 3, 3', and, 3A in corresponding embodiments to be performed individually, the individual functions of the apparatuses may be combined unless they are inconsistent with each other.

The second embodiment group has described a case where the blood-flow-analysis range RA set in the analysis range setting processing includes a plurality of respiratory periods PC, which is not limited thereto and may be a case where the blood-flow-analysis range RA includes only one respiratory period PC.

The image processing apparatus 3, 3', 3A in the second embodiment group includes the cardiac period acquiring unit 425, 425', which may not include the cardiac period acquiring unit 425, 425' if each blood-flow-analysis range RA is set large enough to include a plurality of cardiac periods HBC. In other words, in the case where the blood-flow-analysis value calculating processing can obtain a per-period blood-flow-analysis value SM by obtaining a difference between frame images MI, the cardiac period acquiring unit 425, 425' may not be provided.

The second embodiment group has described the case where each blood-flow-analysis range RA set in the analysis range setting processing includes only one cardiac period HBC, which is not limited thereto and may include a plurality of cardiac periods HBC.

In the second embodiment group, the analysis range setting unit 440 has the configuration of acquiring respiratory information (respiratory phase PH, respiratory period PC, inspiration phase B1, and expiration phase B2) from the phase state judging unit 430 (see FIG. 38 and FIG. 39). Alternatively, the analysis range setting unit 440 may have the configuration of directly acquiring the respiratory information from the respiratory information acquiring unit 420 (420') if the respiratory information acquiring unit 420 (420') and the analysis range setting unit 440 are communicatively connected.

The subject may be an animal body as well as a human body.

<9-1. Summary of Image Processing Apparatus Described in Second Embodiment Group>

For example, the following seventeenth to twenty-ninth aspects of the image processing apparatus according to the second embodiment group (sixth embodiment and seventh embodiment) described above are conceivable. An image processing apparatus of the seventeenth aspect includes moving image acquiring unit, respiratory information acquiring unit, phase state judging unit, analysis range setting unit, and blood-flow-analysis value calculating unit. The moving image acquiring unit acquires a moving image including a plurality of frame images sequentially capturing, in a time direction, a state in which a blood flow of a target region inside a body of a human or an animal changes. The respiratory information acquiring unit performs a respiratory information acquiring processing of acquiring respiratory information in the body synchronized at times at which the frame images are captured. The phase state judging unit judges to which of an inspiration phase state and an expiration phase state the respiratory information belongs and obtains a phase state judgment result. The analysis range setting unit performs an analysis range setting processing of setting a blood-flow-analysis range in at least one of the inspiration phase state and the expiration phase state on the basis of the respiratory information and the phase state judgment result. The blood-flow-analysis value calculating unit performs a blood-flow-analysis value calculating processing of performing a blood flow analysis on the frame images in the blood-flow-analysis range to obtain a blood-flow-analysis value.

In the eighteenth aspect, the image processing apparatus of the seventeenth aspect further includes cardiac period acquiring unit for performing a cardiac period acquiring processing of acquiring a cardiac period in the body synchronized at the photographing time, wherein the analysis range setting processing includes a processing of setting the blood-flow-analysis range such that the blood-flow-analysis range includes at least one cardiac period.

In the nineteenth aspect, in the image processing apparatus of the seventeenth or eighteenth aspect, the target region is a blood vessel region in a lung field region. The respiratory information acquiring processing includes a processing of regarding respiratory vibration values indicated as physical change values of the lung field region as the respiratory information to obtain the respiratory vibration values for at least one respiratory period. The analysis range setting processing includes a processing of setting the blood-flow-analysis range on the basis of the respiratory vibration values for the at least one respiratory period. The blood-flow-analysis range is an analysis range for inspiration phase and an analysis range for expiration phase respectively corresponding to the inspiration phase state and the expiration phase state. The blood-flow-analysis value calculating processing includes a processing of individually performing the blood flow analysis in the analysis range for inspiration phase and the analysis range for expiration phase to individually obtain the blood-flow-analysis value.

In the twentieth aspect, in the image processing apparatus of the nineteenth aspect, the blood-flow-analysis range includes a range that satisfies, for an amplitude direction of the respiratory vibration values for the at least one respiratory period, one of (a) an amplitude value range set on the basis of amplitude values of the respiratory vibration values, and (b) a diagnostic purpose range set in accordance with a diagnostic purpose, and for a direction of the photographing time, one of (c) an analysis target period being an analysis target of the at least one period with the respiratory vibration values acquired in the respiratory information acquiring processing, and (d) a phase-specific analysis target period corresponding to any of the inspiration phase and the expiration phase of a period being the analysis target period.

In the twenty-first aspect, in the image processing apparatus of the twentieth aspect, the respiratory information acquiring processing further includes a processing of calculating a maximum value and a minimum value of the respiratory vibration values in the respiratory period. The amplitude value range includes any one of (a1) a range set on the basis of a preset first range, and (a2) a range set on the basis of the maximum value and the minimum value in the respiratory period.

In the twenty-second aspect, in the image processing apparatus of the twentieth aspect, the respiratory information acquiring processing further includes a processing of calculating a maximum value and a minimum value of the respiratory vibration values in the respiratory period. The diagnostic purpose range includes a range set in a range in which the respiratory vibration values are greater than the minimum value and are smaller than the maximum value.

In the twenty-third aspect, in the image processing apparatus of any one of the seventeenth to twenty-second aspects, the respiratory information acquiring processing includes a processing of regarding respiratory vibration values indicated as physical change values of a lung field region of the body as the respiratory information to acquire the respiratory vibration values for a plurality of respiratory periods. The analysis target range setting unit includes a processing of setting, as an analysis target, at least two respiratory periods of the plurality of respiratory periods. The blood-flow-analysis value calculating processing includes a processing of obtaining the at least two per-period blood-flow-analysis values in the at least two respiratory periods to finally obtain the blood-flow-analysis value using the at least two per-period blood-flow-analysis values.

In the twenty-fourth aspect, in the image processing apparatus of the twenty-third aspect, the respiratory information acquiring processing further includes a processing of calculating the respiratory period on the basis of the respiratory vibration values, and a processing of calculating a maximum value and a minimum value of the respiratory vibration values per respiratory period.

In the twenty-fifth aspect, in the image processing apparatus of any one of the twenty-first to twenty-fourth aspects, the phase state judging processing includes a processing of judging to which of the inspiration phase state and the expiration phase state the respiratory vibration values belong on the basis of the maximum value and the minimum value of the respiratory vibration values in the respiratory period.

In the twenty-sixth aspect, in the image processing apparatus of the twentieth aspect, the respiratory information acquiring processing further includes a processing of calculating an overall maximum value indicating a maximum value of the respiratory vibration values in an overall time. The diagnostic purpose range includes a range set in a range in the vicinity of the overall maximum value.

In the twenty-seventh aspect, in the image processing apparatus of the twenty-sixth aspect, the diagnostic purpose range includes a range that is in the vicinity of the overall maximum value and excludes the overall maximum value.

In the twenty-eighth aspect, in the image processing apparatus of the twenty-third aspect, in a case where a plurality of the inspiration phases or a plurality of the expiration phases have a plurality of the same amplitude ranges in which ranges of the respiratory vibration values among a plurality of the blood-flow-analysis ranges that have been set are the same, the analysis range setting processing includes a processing of instructing the blood-flow-analysis value calculating unit to perform, on the plurality of per-period blood-flow-analysis values calculated in the plurality of the same amplitude ranges, any one of (e1) a processing of calculating an in-range average value indicating an averaged value as the blood-flow-analysis value, (e2) a processing of calculating an in-range maximum value indicating a maximum value as the blood-flow-analysis value, and (e3) a processing of calculating an in-range minimum value indicating a minimum value as the blood-flow-analysis value, and (f) a processing of generating an image using any one of the in-range average value, the in-range maximum value, and the in-range minimum value.

The twenty-ninth aspect relates to a computer-readable non-transitory storage medium storing a program, which is executed by a computer included in an image processing apparatus according to any one of the seventeenth to the twenty-eighth aspects.

According to the image processing apparatus of the seventeenth aspect, a blood-flow-analysis range in at least one of the inspiration phase state and the expiration phase state is set on the basis of respiratory information and a phase state judgment result, and a blood flow analysis is performed on frame images in the blood-flow-analysis range, thereby obtaining a blood-flow-analysis value in the at least one state. Thus, a blood-flow-analysis value that corresponds to at least one of the inspiration phase state and the expiration phase state desired by a user, that is, that reflects the phase state of respiration, can be obtained. This enables appropriate, efficient image diagnosis of a blood flow.

According to the image processing apparatus of the eighteenth aspect, the analysis range setting processing sets a blood-flow-analysis range such that the blood-flow-analysis range includes at least one cardiac period. Therefore, a blood-flow-analysis value can be obtained with at least one cardiac period included. The movement of a blood flow for one cardiac period can be accordingly understood.

According to the image processing apparatus of the nineteenth aspect, the blood-flow-analysis value calculating processing performs a processing of individually performing a blood flow analysis in the analysis range for inspiration phase and the analysis range for expiration phase to individually obtain a blood-flow-analysis value. This prevents a decrease in the accuracy of blood flow analysis associated with different pressures on the blood vessels in the lung field between in the inspiration phase state and in the expiration phase state. This enables image diagnosis of a blood flow individually corresponding to the inspiration phase state and the expiration phase state.

According to the image processing apparatus of the twentieth aspect, the blood-flow-analysis range includes a range that satisfies, for an amplitude direction of respiratory vibration values of one or more respiratory periods, one of the amplitude value range and the diagnostic purpose range and satisfies, for a direction of the photographing time, one of the analysis target period and the phase-specific analysis target period. This allows setting of a blood-flow-analysis range according to the use by a user. In the case where the user needs a blood-flow-analysis value in only any one of the expiration phase state and the inspiration phase state, setting is performed in a phase-specific analysis target period. This requires a calculation performed in the blood-flow-analysis value calculating processing for only one of the phase states, reducing a calculation time compared with the case where setting is performed in an analysis target period.

According to the image processing apparatus of the twenty-first aspect, in the case where an amplitude value range is set on the basis of (a1) a preset first range, determination can be made automatically without the user's taking into account respiratory vibration values. In the case where setting is performed on the basis of (a2) a maximum value and a minimum value of the respiratory vibration values in the respiratory period, an appropriate amplitude value range corresponding to the respiratory vibration value can be set automatically.

According to the image processing apparatus of the twenty-second aspect, a diagnostic purpose range is set in a range in which respiratory vibration values are larger than a minimum value and are smaller than a maximum value. In other words, a maximum inspiration phase and a maximum expiration phase respectively corresponding to the maximum value and the minimum value of the respiratory vibration values have abnormal pressure on the blood vessel in the lung field, which is not a favorable condition for a blood flow. Thus, eliminating the two phase states enables the range of the best blood flow to be set as a blood-flow-analysis range, obtaining a stable blood-flow-analysis value.

According to the image processing apparatus of the twenty-third aspect, the blood-flow-analysis value calculating processing performs a processing of obtaining at least two per-period blood-flow-analysis values in at least two respiratory periods to finally obtain a blood-flow-analysis value using the at least two per-period blood-flow-analysis values. Thus, a plurality of per-period blood-flow-analysis values can be taken into account to determine a final blood-flow-analysis value in at least one of the inspiration phase state and the expiration phase state, which cannot be performed in the blood flow analysis for one respiration period. This enables more appropriate, efficient image diagnosis of a blood flow.

According to the image processing apparatus of the twenty-fourth aspect, a respiratory period is calculated on the basis of respiratory vibration values, and a maximum value and a minimum value of the respiratory vibration values are calculated per respiratory period. The maximum value and the minimum value of the respiratory vibration values per respiratory period typically differ from one respiratory period to another. Thus, for example, in the case where a maximum value and a minimum value are set in an amplitude value range per respiratory period, an amplitude value range can be set individually per respiratory period.

According to the image processing apparatus of the twenty-fifth aspect, the phase state judging processing judges to which of the inspiration phase state and the expiration phase state the respiratory vibration values belong on the basis of the maximum value and the minimum value of the respiratory vibration values in the respiratory period. Therefore, the phase state of the respiratory vibration values can be judged appropriately and easily on the basis of a maximum inspiration phase and a maximum expiration phase respectively corresponding to the maximum value and the minimum value of the respiratory vibration values in the respiratory period.

According to the image processing apparatus of the twenty-sixth aspect, a diagnostic purpose range is set in a range in the vicinity of an overall maximum value, which allows a blood-flow-analysis range to be set near the maximum inspiration phase. In other words, the blood vessels of the lung field region stretch most in the lung field near the maximum inspiration phase. Thus, a blood-flow-analysis range is set near the maximum inspiration phase, and then, a blood flow analysis is performed, thereby understanding the shape of blood vessels in the lung field.

According to the image processing apparatus of the twenty-seventh aspect, the diagnostic purpose range includes a range that is in the vicinity of the overall maximum value and excludes the maximum value. Thus, a blood-flow-analysis range can be set near the maximum inspiration phase in which the blood vessels of the lung field region stretch most in the lung field, so that the shape of the blood vessels in the lung field can be understood from the obtained blood-flow-analysis value.

Also, in the maximum inspiration phase corresponding to the overall maximum value, a phenomenon occurs in which a blood flow through the blood vessels of the lung field region is restricted and the blood flow is attenuated. Thus, the shape of the blood vessels in the lung field is hard to understand if a blood flow analysis is performed. Therefore, the overall maximum value is eliminated from the blood-flow-analysis range, thereby obtaining an appropriate blood-flow-analysis value.

According to the image processing apparatus of the twenty-eighth aspect, the analysis range setting processing performs a processing of instructing the blood-flow-analysis value calculating unit to perform, on a plurality of per-period blood-flow-analysis values calculated in a plurality of the same amplitude ranges, any one of (e1) a processing of calculating an in-range average value indicating an averaged value as a blood-flow-analysis value, (e2) a processing of calculating an in-range maximum value indicating a maximum value as a blood-flow-analysis value, and (e3) a processing of calculating an in-range minimum value indicating a minimum value as a blood-flow-analysis value, and (f) a processing of generating an image using any one of the in-range average value, the in-range maximum value, and the in-range minimum value. In generation of an image using an in-range average value, high-frequency noise components included in a per-period blood-flow-analysis value can be reduced, generating a smoothed image. Near the maximum inspiration phase, the accuracy of blood flow analysis decreases due to an attenuated blood flow in the lung field region. For this reason, to diagnose an image having a blood-flow-analysis value near the maximum inspiration phase, one image is effectively generated using an in-range maximum value. Further, a difference, which occurs in the comparison between an image generated using an in-range maximum value and an image generated using an in-range minimum value, can be diagnosed per respiratory period.

According to the twenty-ninth aspect, similar effects to those of the seventeenth to the twenty-eighth aspects can be achieved.

Although a blood flow analysis is performed on the basis of an image acquired using radiation such as X-rays in the embodiments of the first embodiment group and the second embodiment group, the present invention is not limited to the case involving X-rays. Alternatively, the present invention may use any technology as long as an image of the interior of the body can be obtained. In one example, the present invention is also applicable to a technology of achieving an image of the interior of the body using, for example, MRI to perform a blood flow analysis.

The invention claimed is:

1. An image processing apparatus that performs a blood flow analysis, comprising:
    moving image acquiring unit for acquiring a moving image including a plurality of frame images sequentially capturing, in a time direction, a state in which a blood flow of a target region inside a body of a human or an animal changes;
    respiratory information acquiring unit for performing a respiratory information acquiring processing of acquiring respiratory information in said body synchronized at times at which said frame images are captured;
    blood-flow-restricted time determining unit for performing a blood-flow-restricted time determining processing of determining, on the basis of said respiratory information, a blood-flow-restricted time indicating a time at which the blood flow of said target region is assumed to be restricted due to respiration; and
    blood flow analysis correcting unit for performing a blood-flow-analysis content correcting processing of excluding said frame image captured at said blood-flow-restricted time from targets for blood flow analysis or decreasing the blood-flow-analysis importance of said frame image compared with another time period.

2. The image processing apparatus according to claim 1, wherein
    said respiratory information acquiring processing includes a processing of acquiring, as said respiratory information, respiratory vibration values indicated as physical change values of a lung field region of said body, and
    said blood-flow-restricted time determining processing includes a processing of determining, as said blood-flow-restricted time, a time at which said respiratory vibration value becomes a maximum value.

3. The image processing apparatus according to claim 1, wherein
    said respiratory information acquiring processing includes a processing of acquiring, as said respiratory information, respiratory vibration values indicated as physical change values of a lung field region of said body,
    a respiratory period is recognizable from said respiratory vibration values, and
    said blood-flow-restricted time determining processing includes a processing of determining, per said respiratory period, a time at which said respiratory vibration value becomes a maximum value as said blood-flow-restricted time.

4. The image processing apparatus according to claim 1, wherein
    said respiratory information acquiring processing includes a processing of acquiring, as said respiratory information, relative respiration values indicating relative values that enable judgment about to which of an inspiration phase and an expiration phase of said body said respiratory vibration values belong,
    a respiratory period is recognizable from said relative respiration values, and
    said blood-flow-restricted time determining processing includes a processing of determining, per said respiratory period, a time at which said relative respiration value changes from said inspiration phase to said expiration phase as said blood-flow-restricted time.

5. The image processing apparatus according to claim 2, wherein said blood-flow-restricted time determining unit includes a blood-flow-restricted time extending unit that extends said blood-flow-restricted time to provide a time width relative to said blood-flow-restricted time.

6. The image processing apparatus according to claim 2, wherein
    said blood-flow-restricted time determining unit includes a blood-flow-restricted time extending unit that extends said blood-flow-restricted time to provide a time width relative to said blood-flow-restricted time, and
    said blood-flow-restricted time extending unit includes an amplitude-direction extending unit that performs an amplitude-direction extending processing of setting said time width at a time at which said respiratory vibration value is not less than a first threshold, said first threshold being a value smaller by a first value than a value that is the maximum value of said respiratory vibration values.

7. The image processing apparatus according to claim 6, wherein said first value includes any one of
    (b1) a value calculated on the basis of a difference value between the maximum value and a minimum value of said respiratory vibration values, and
    (b2) a predetermined constant value.

8. The image processing apparatus according to claim 3, wherein
    said blood-flow-restricted time determining unit includes a blood-flow-restricted time extending unit that extends said blood-flow-restricted time to provide a time width relative to said blood-flow-restricted time, and
    said blood-flow-restricted time extending unit includes an amplitude-direction extending unit that performs an amplitude-direction extending processing of setting said time width at a time at which said respiratory vibration value is not less than a second threshold, said second threshold being a value smaller by a second value than the maximum value of said respiratory vibration values for each respiratory period.

9. The image processing apparatus according to claim 8, wherein said second value includes any one of
(c1) a value set per said respiratory period and calculated on the basis of a difference value between the maximum value and a minimum value of said respiratory vibration values for each respiratory period, and
(c2) a predetermined constant value.

10. The image processing apparatus according to claim 1, wherein
said respiratory information acquiring processing includes a processing of acquiring, as said respiratory information, respiratory vibration values indicated as physical change values of a lung field region of said body, and
said blood-flow-restricted time determining processing includes a processing of determining, as said blood-flow-restricted time, a time at which said respiratory vibration value is not less than a predetermined reference value.

11. The image processing apparatus according to claim 3, wherein
said blood-flow-restricted time determining unit includes a blood-flow-restricted time extending unit that extends said blood-flow-restricted time to provide a time width relative to said blood-flow-restricted time, and
said time width includes any one of
(d1) a combined time width of a first time width determined on the basis of a time required for the inspiration phase and a second time width determined on the basis of a time required for the expiration phase, per said respiratory period,
(d2) a time width determined, per said respiratory period, on the basis of a time required for one period, and
(d3) a predetermined time width.

12. The image processing apparatus according to claim 2, further comprising blood-flow-restricted time limiting unit for limiting said blood-flow-restricted time determining processing to satisfy any one of
(e1) a condition that a total time of times required for analysis used in said blood flow analysis at times other than said blood-flow-restricted time in an overall time is not less than a first reference time, and
(e2) a condition that times required for analysis used in said blood flow analysis at times other than said blood-flow-restricted time per said respiratory period is not less than a second reference time.

13. The image processing apparatus according to claim 1, further comprising blood-flow-cycle detecting unit for detecting a blood flow cycle of said target region,
wherein said blood flow analysis correcting unit includes a blood flow cycle unitizing unit that adjusts said blood-flow-restricted time such that a blood flow analysis is performed on the blood-flow-restricted time determined in said blood-flow-restricted time determining processing in units of said blood flow cycle.

14. The image processing apparatus according to claim 1, wherein
said blood-flow-analysis content correcting processing includes any one of, for analysis data being a target for said blood flow analysis in said moving image,
a preprocessing to be performed before a blood flow analyzing processing of obtaining a blood-flow-analysis value is performed, and
a postprocessing to be performed after said blood flow analyzing processing is performed,
said preprocessing includes, for data at said blood-flow-restricted time of said analysis data, any one of
(a1) a processing of prohibiting said blood flow analyzing processing, and
(a2) a processing of decreasing importance to cause said blood flow analyzing processing to be performed, and
said postprocessing includes, for data at said blood-flow-restricted time of said blood-flow-analysis value, any one of
(a3) a processing of treating the data not as said blood-flow-analysis value, and
(a4) a processing of decreasing the importance of said blood-flow-analysis value.

15. The image processing apparatus according to claim 1, wherein said target region includes a blood vessel region in the lung field region.

16. A computer-readable non-transitory storage medium storing a program, which is executed by a computer included in an image processing apparatus according to claim 1.

17. An image processing apparatus, comprising:
moving image acquiring unit for acquiring a moving image including a plurality of frame images sequentially capturing, in a time direction, a state in which a blood flow of a target region inside a body of a human or an animal changes;
respiratory information acquiring unit for performing a respiratory information acquiring processing of acquiring respiratory information in said body synchronized at photographing times when said frame images are captured;
phase state judging unit for judging to which of an inspiration phase state and an expiration phase state said respiratory information belongs and obtaining a phase state judgment result;
analysis range setting unit for performing an analysis range setting processing of setting a blood-flow-analysis range in at least one of said inspiration phase state and said expiration phase state on the basis of said respiratory information and said phase state judgment result; and
blood-flow-analysis value calculating unit for performing a blood-flow-analysis value calculating processing of performing a blood flow analysis on said frame images in said blood-flow-analysis range to obtain a blood-flow-analysis value in said at least one of the states.

18. The image processing apparatus according to claim 17, farther comprising cardiac period acquiring unit for performing a cardiac period acquiring processing of acquiring a cardiac period in said body synchronized at said photographing time,
wherein said analysis range setting processing includes a processing of setting said blood-flow-analysis range such that said blood-flow-analysis range includes at least one said cardiac period.

19. The image processing apparatus according to claim 17, wherein
said target region comprises a blood vessel region in a lung field region,
said respiratory information acquiring processing includes a processing of regarding respiratory vibration values indicated as physical change values of said lung field region as said respiratory information to obtain said respiratory vibration values for at least one respiratory period, said analysis range setting processing includes a processing of setting said blood-flow-analysis range on the basis of said respiratory vibration values for said at least one respiratory period, said blood-flow-analysis range comprises an analysis range for inspiration phase and an analysis range for expiration phase respectively corresponding to said inspiration phase state and said expiration phase state, and said blood-flow-analysis value calculating processing includes a processing of individually performing said blood flow analysis in said analysis range for inspiration phase and said analysis range for expiration phase to individually obtain said blood-flow-analysis value.

20. The image processing apparatus according to claim 19, wherein said blood-flow-analysis range includes a range that satisfies for an amplitude direction of said respiratory vibration values for said at least one respiratory period, one of
  (a) an amplitude value range set on the basis of amplitude values of said respiratory vibration values, and
  (b) a diagnostic purpose range set in accordance with a diagnostic purpose, for a direction of said photographing time, one of
  (c) an analysis target period being an analysis target of said at least one period with said respiratory vibration values acquired in said respiratory information acquiring processing, and
  (d) a phase-specific analysis target period corresponding to any of said inspiration phase and said expiration phase of a period being said analysis target period.

21. The image processing apparatus according to claim 20, wherein said respiratory information acquiring processing further includes a processing of calculating a maximum value and a minimum value of said respiratory vibration values in said respiratory period, and said amplitude value range includes any one of
  (a1) a range set on the basis of a preset first range, and
  (a2) a range set on the basis of said maximum value and said minimum value in said respiratory period.

22. The image processing apparatus according to claim 20, wherein said respiratory information acquiring processing further includes a processing of calculating a maximum value and a minimum value of said respiratory vibration values in said respiratory period, and said diagnostic purpose range includes a range set in a in which said respiratory vibration values are greater than said minimum value and are smaller than said maximum value.

23. The image processing apparatus according to claim 17, wherein said respiratory information acquiring processing includes a processing of regarding respiratory vibration values indicated as physical change values of a lung field region of said body as said respiratory information to acquire said respiratory vibration values for a plurality of respiratory periods, said analysis target range setting processing includes a processing of setting, as an analysis target, at least two respiratory periods of said plurality of respiratory periods, and said blood-flow-analysis value calculating processing includes a processing of obtaining at least two per-period blood-flow-analysis values in said at least two respiratory periods to finally obtain said blood-flow-analysis value using said at least two per-period blood-flow-analysis values.

24. The image processing apparatus according to claim 23, wherein said respiratory information acquiring processing further includes a processing of calculating said respiratory period on the basis of said respiratory vibration values, and a processing of calculating a maximum value and a minimum value of said respiratory vibration values per said respiratory period.

25. The image processing apparatus according to claim 21, wherein said phase state judging processing includes a processing of judging to which of said inspiration phase state and said expiration phase state said respiratory vibration values belong on the basis of the maximum value and the minimum value of said respiratory vibration values in said respiratory period.

26. The image processing apparatus according to claim 20, wherein said respiratory information acquiring processing further includes a processing of calculating an overall maximum value indicating a maximum value of said respiratory vibration values in an overall time, and said diagnostic purpose range includes a range set in a range in the vicinity of said overall maximum value.

27. The image processing apparatus according to claim 26, wherein said diagnostic purpose range includes a range that is in the vicinity of said overall maximum value and excludes said overall maximum value.

28. The image processing apparatus according to claim 23, wherein in a case where a plurality of said inspiration phases or a plurality of said expiration phases have a plurality of the same amplitude ranges in which ranges of said respiratory vibration values among a plurality of said blood-flow-analysis ranges that have been set are the same, said analysis range setting processing includes a processing of instructing said blood-flow-analysis value calculating unit to perform, on said plurality of per-period blood-flow-analysis values calculated in said plurality of the same amplitude ranges, any one of
  (e1) a processing of calculating an in-range average value indicating an averaged value as said blood-flow-analysis value,
  (e2) a processing of calculating an in-range maximum value indicating a maximum value as said blood-flow-analysis value, and
  (e3) a processing of calculating an in-range minimum value indicating a minimum value as said blood-flow-analysis value, and (f) a processing of generating an image using any one of said in-range average value, said in-range maximum value, and said in-range minimum value.

29. A computer-readable non-transitory storage medium storing a program, which is executed by a computer included in an image processing apparatus according to claim 17.

* * * * *